US 011179537B2

United States Patent
Bornholdt et al.

(10) Patent No.: US 11,179,537 B2
(45) Date of Patent: Nov. 23, 2021

(54) MASK SYSTEM HEADGEAR

(71) Applicant: Fisher & Paykel Healthcare Limited, Auckland (NZ)

(72) Inventors: Melissa Catherine Bornholdt, Auckland (NZ); Max Leon Betteridge, Auckland (NZ); Gregory James Olsen, Auckland (NZ); Mark Arvind McLaren, Auckland (NZ); Bernard Tsz Lun Ip, Auckland (NZ); Simon Mittermeier, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 16/950,796

(22) Filed: Nov. 17, 2020

(65) Prior Publication Data

US 2021/0060279 A1 Mar. 4, 2021

Related U.S. Application Data

(62) Division of application No. 15/555,350, filed as application No. PCT/IB2016/051212 on Mar. 3, 2016.

(Continued)

(51) Int. Cl.
*A61M 16/06* (2006.01)
*A61M 16/00* (2006.01)
(Continued)

(52) U.S. Cl.
CPC .... *A61M 16/0683* (2013.01); *A61M 16/0633* (2014.02); *A61M 16/024* (2017.08);
(Continued)

(58) Field of Classification Search
CPC .............. A61M 16/06; A61M 16/0633; A61M 16/0638; A61M 16/0644; A61M 16/065;
(Continued)

(56) References Cited

U.S. PATENT DOCUMENTS

| 5,921,239 A | 7/1999 | McCall et al. |
| 6,269,814 B1 | 8/2001 | Blaszczykiewicz et al. |

(Continued)

FOREIGN PATENT DOCUMENTS

| AU | 2014202233 A1 | 5/2014 |
| CN | 101450239 A | 6/2009 |

(Continued)

OTHER PUBLICATIONS

Combined Search and Examination Report for United Kingdom Patent Application No. GB2019664.8, dated Jan. 19, 2021 in 5 pages.

(Continued)

*Primary Examiner* — Joseph D. Boecker
(74) *Attorney, Agent, or Firm* — Knobbe, Martens, Olson & Bear, LLP

(57) ABSTRACT

A respiratory mask system includes a headgear that, in use, secures the respiratory mask system to a patient's head. The headgear includes a pair of forehead straps that are coupled together by a forehead coupler to form a closed loop. The forehead coupler is removably connected to a frame of the respiratory mask such that the forehead straps remain in a closed loop. The pair of forehead straps can also be coupled together by positioning a male strap portion within an aperture of a female strap portion. The male strap portion has a free end that is configured to be received into the aperture. The male strap portion includes a plurality of notches that engage the aperture of the female strap portion and provide incremental adjustment. The free ends of the male and (Continued)

female strap portions have fasteners configured to engage the surface of the other strap portion.

54 Claims, 42 Drawing Sheets

Related U.S. Application Data

(60) Provisional application No. 62/128,434, filed on Mar. 4, 2015, provisional application No. 62/187,010, filed on Jun. 30, 2015, provisional application No. 62/268,341, filed on Dec. 16, 2015.

(51) Int. Cl.
*A61M 16/08* (2006.01)
*A61M 16/16* (2006.01)

(52) U.S. Cl.
CPC ......... *A61M 16/06* (2013.01); *A61M 16/0816* (2013.01); *A61M 16/16* (2013.01); *A61M 2205/3334* (2013.01); *A61M 2205/3368* (2013.01); *A61M 2205/581* (2013.01)

(58) Field of Classification Search
CPC .......... A61M 16/0655; A61M 16/0683; A62B 18/084
See application file for complete search history.

(56) References Cited

U.S. PATENT DOCUMENTS

| | | | |
|---|---|---|---|
| 6,595,214 B1* | 7/2003 | Hecker | A61M 16/06 128/206.21 |
| 2003/0075180 A1* | 4/2003 | Raje | A61M 16/06 128/206.24 |
| 2004/0182398 A1 | 9/2004 | Sprinkle et al. | |
| 2006/0076019 A1* | 4/2006 | Ho | A61M 16/0638 128/206.24 |
| 2007/0163600 A1 | 7/2007 | Hoffman | |
| 2007/0209663 A1 | 9/2007 | Marque et al. | |
| 2008/0178875 A1 | 7/2008 | Henry | |
| 2008/0223373 A1 | 9/2008 | Chang | |
| 2009/0044808 A1 | 2/2009 | Guney et al. | |
| 2010/0006101 A1 | 1/2010 | McAuley. et al. | |
| 2012/0103340 A1* | 5/2012 | Chu | A61M 16/0655 128/206.21 |
| 2012/0138061 A1* | 6/2012 | Dravitzki | A61M 16/0633 128/205.25 |
| 2012/0199132 A1* | 8/2012 | Ho | A61M 16/0633 128/206.24 |
| 2012/0222680 A1 | 9/2012 | Eves et al. | |
| 2012/0234326 A1 | 9/2012 | Mazzone et al. | |
| 2012/0285452 A1 | 11/2012 | Amirav et al. | |
| 2013/0186404 A1 | 7/2013 | Chien | |
| 2013/0319419 A1* | 12/2013 | Lee | A61M 16/0655 128/206.21 |
| 2014/0174446 A1 | 6/2014 | Prentice et al. | |
| 2014/0224255 A1* | 8/2014 | McCaslin | A61M 16/0633 128/205.25 |
| 2018/0036505 A1* | 2/2018 | Bornholdt | A61M 16/0605 |

FOREIGN PATENT DOCUMENTS

| | | |
|---|---|---|
| CN | 101951984 A | 1/2011 |
| EP | 2281596 A1 | 2/2011 |
| EP | 2668971 A1 | 12/2013 |
| EP | 2818194 A1 | 12/2014 |
| EP | 2954920 A1 | 12/2015 |
| JP | 2011-512967 | 4/2011 |
| JP | 2014-517735 | 7/2014 |
| WO | WO 02/47749 A1 | 6/2002 |
| WO | WO 2004/021960 A2 | 3/2004 |
| WO | WO 2009/026627 A1 | 3/2009 |
| WO | WO 2009/108995 A1 | 9/2009 |
| WO | WO 2010/135785 A1 | 12/2010 |
| WO | WO 2011/060479 A1 | 5/2011 |
| WO | WO 2012/045127 | 4/2012 |
| WO | WO 2012/140514 | 10/2012 |
| WO | WO 2013/006899 | 1/2013 |
| WO | WO 2013/064950 | 5/2013 |
| WO | WO 2013/066195 A1 | 5/2013 |
| WO | WO 2014/062070 A1 | 4/2014 |
| WO | WO 2014/129913 A1 | 8/2014 |
| WO | WO 2015/057087 A1 | 4/2015 |
| WO | WO 2016/009393 A1 | 1/2016 |
| WO | WO 2016/032343 A1 | 3/2016 |
| WO | WO 2016/033857 A1 | 3/2016 |
| WO | WO 2016/139623 | 9/2016 |

OTHER PUBLICATIONS

International Search Report and Written Opinion, PCT/NZ2015/050119, dated Nov. 20, 2015 in 16 pages.
Japanese Office Action, Patent Application No. 2017-511715, dated Jul. 1, 2019, in 4 pages.
Office Action; Japanese Application No. 2017-546199; 9 pages total (including English translation).
Examination Report for Australian Application No. 2016227361; dated Oct. 8, 2019; 6 pages.
Chinese Office Action dated Jul. 26, 2019; CN Application No. 201680025933.3; 17 pages total (including translation).
Examination Report under section 18(3); Application No. GB1713194.7, dated Feb. 26, 2020; 2 pages.
European Search Report for European Patent Application No. 20166100.6, dated Sep. 10, 2020 in 4 pages.
Japanese Decision of Refusal in Japanese App. No. JP 2017-511715 dated May 28, 2020 (4 pgs).
European Search Opinion for European Application No. 16758540.5, dated Sep. 27, 2018 in 7 pages.
International Search Report for International Application No. PCT/IB2016/051212, dated Jun. 8, 2016 in 10 pages.
International Preliminary Report on Patentability for International Application No. PCT/IB2016/051212, dated Sep. 5, 2017 in 15 pages.
Decision to grant a European patent Application No. 16758540.5, dated Apr. 9, 2020 in 2 pages.
Search Report for United Kingdom Patent Application No. GB1713194.7, dated Oct. 22, 2020.
Examination Report for United Kingdom Patent Application No. GB1702508.1, dated Nov. 6, 2020.
Combined Search and Examination Report for United Kingdom Patent Application No. GB2015110.6, dated Nov. 5, 2020 in 4 pages.

\* cited by examiner

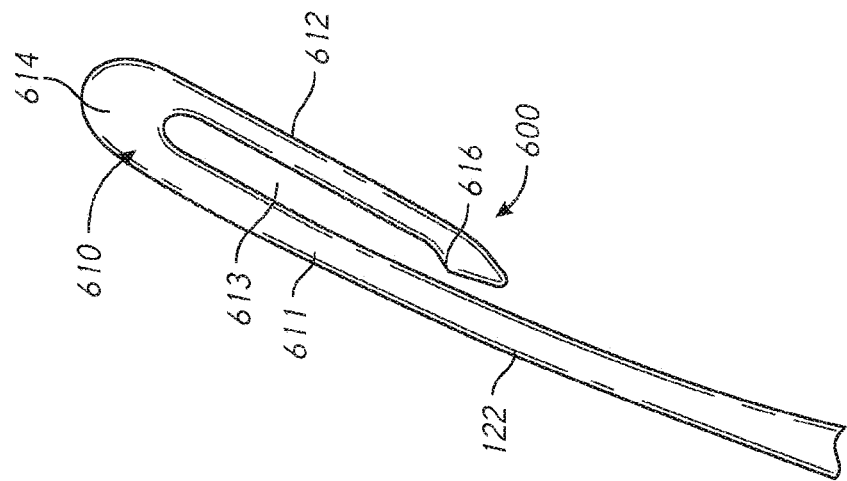
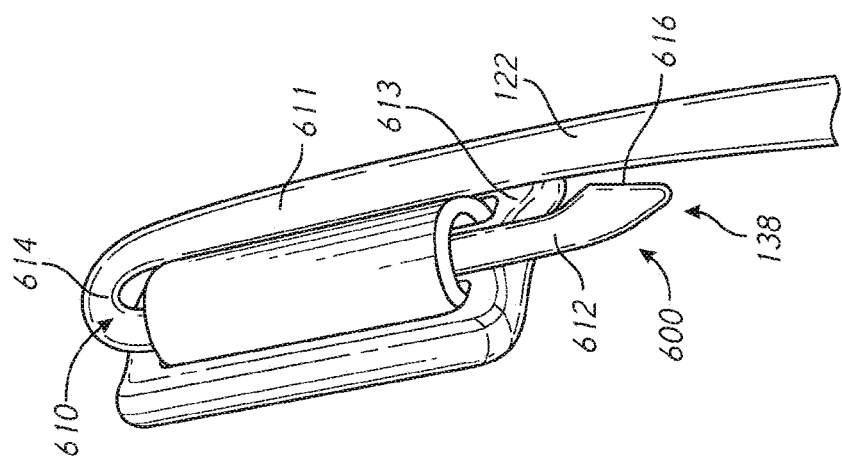
FIG. 13B
FIG. 13A

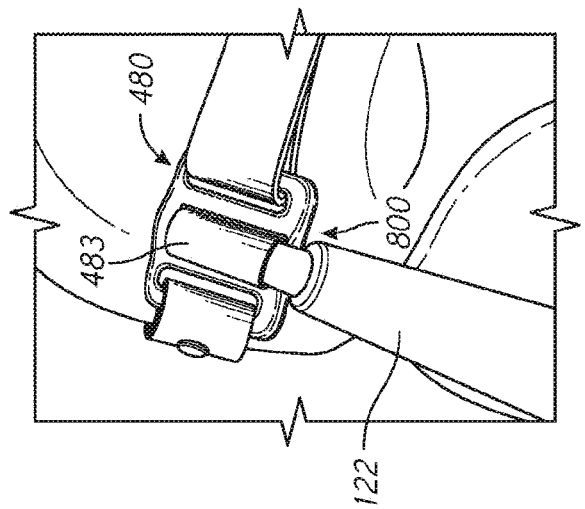
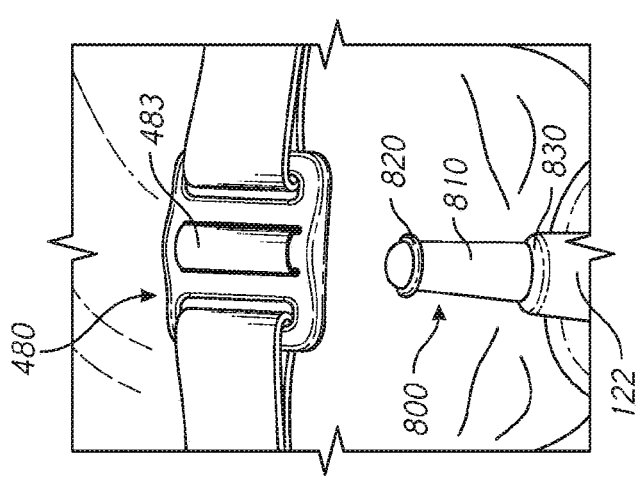

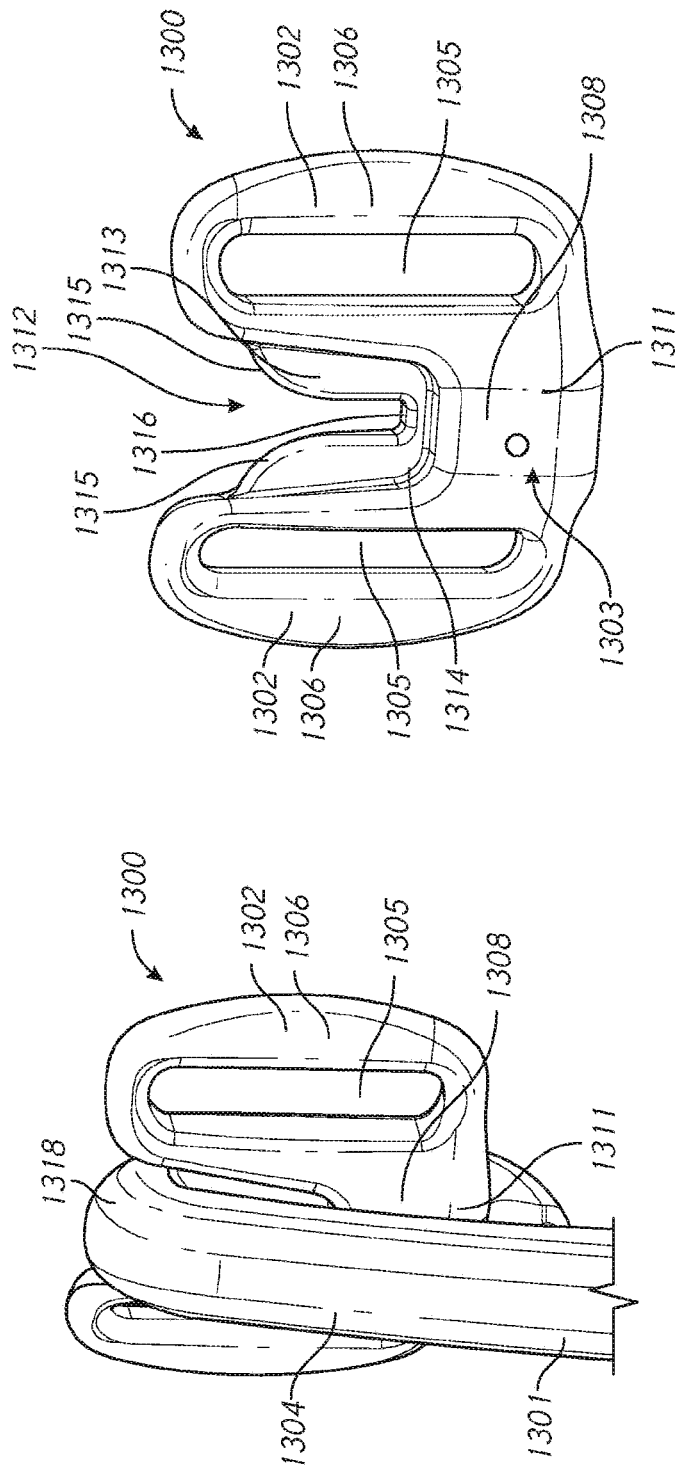

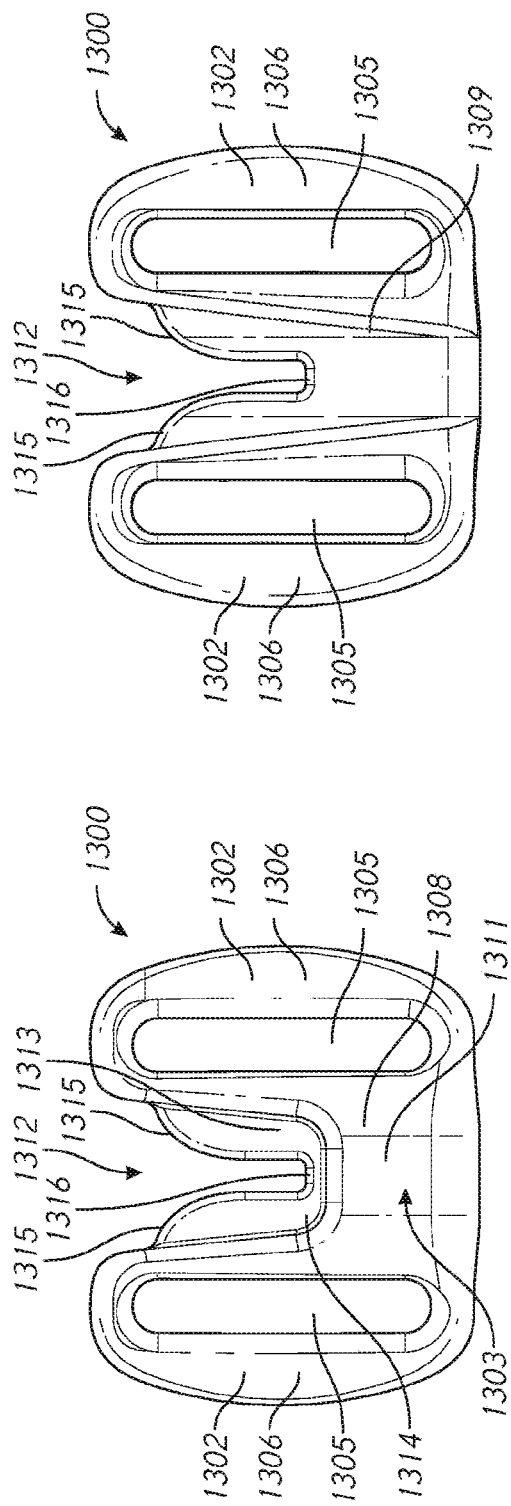
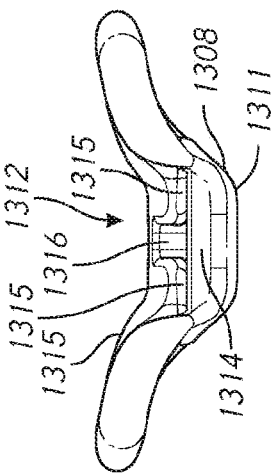
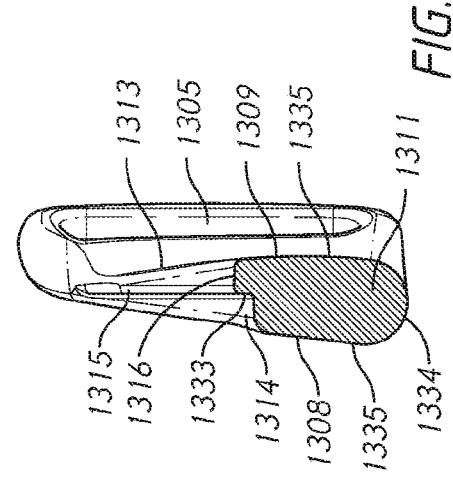
FIG. 20D
FIG. 20F
FIG. 20C
FIG. 20E

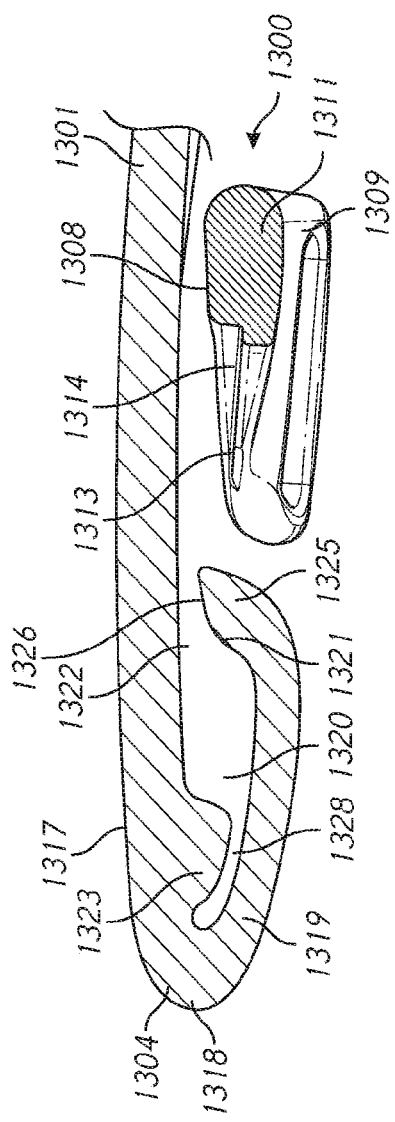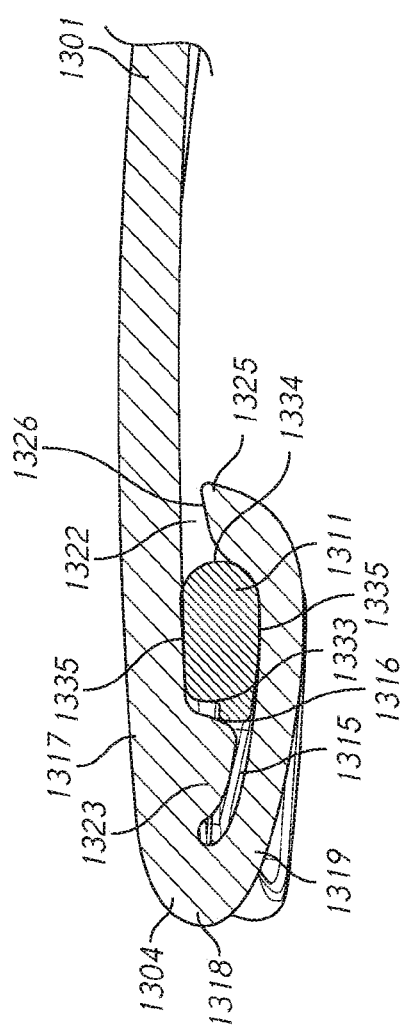
FIG. 20I
FIG. 20J

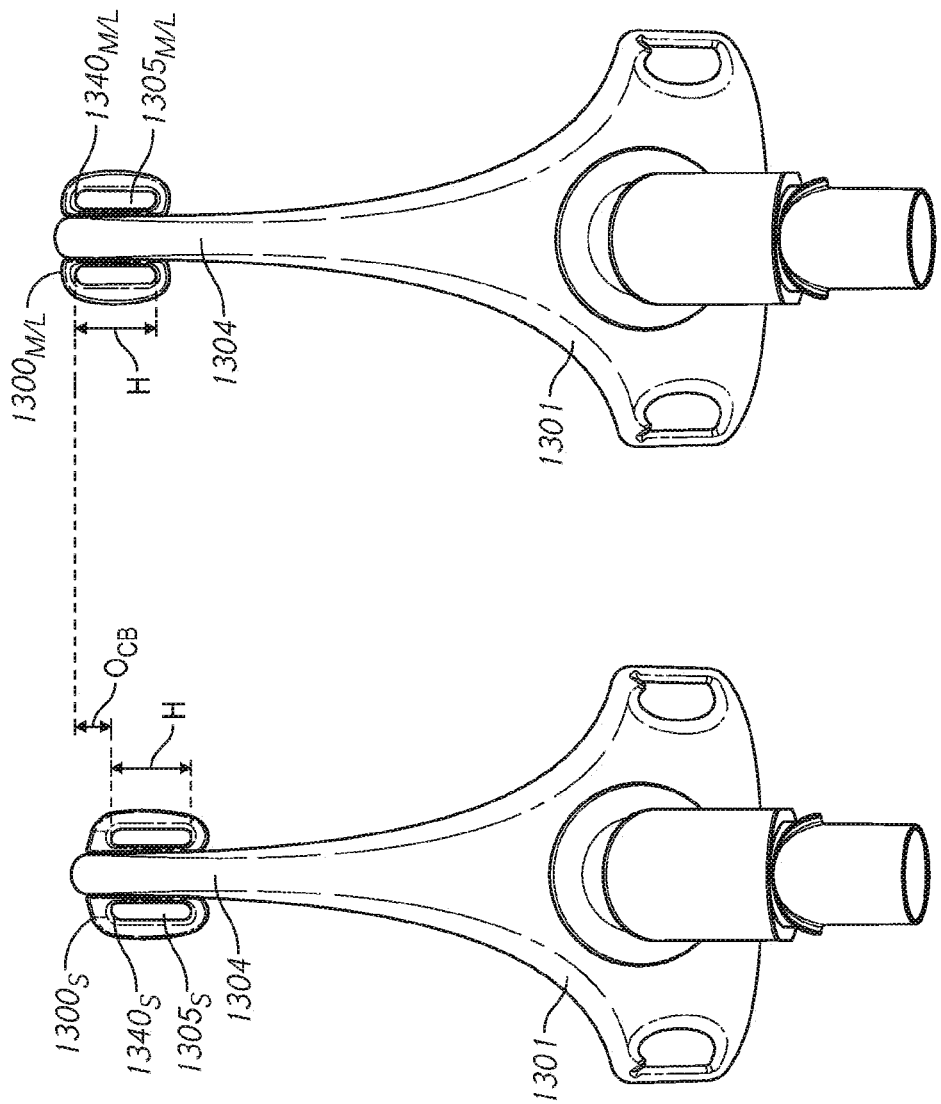

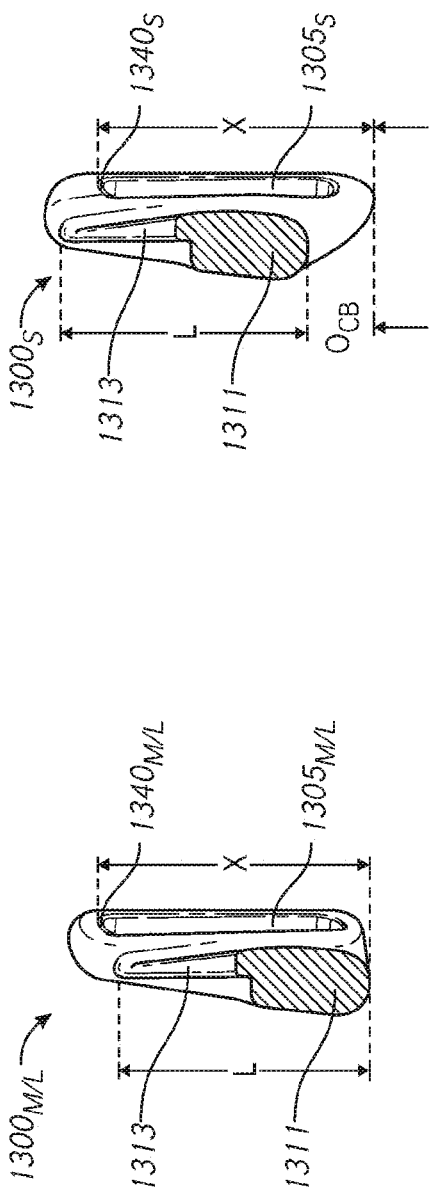

MASK SYSTEM HEADGEAR

INCORPORATION BY REFERENCE TO PRIORITY APPLICATIONS

This application is related to and claims priority from U.S. Provisional Patent Application No. 62/128,434, U.S. Provisional Patent Application No. 62/187,010 and U.S. Provisional Patent Application No. 62/268,341, the entireties of which are hereby incorporated by reference herein and made a part of the present disclosure.

BACKGROUND

Technical Field

The present disclosure generally relates to masks for use in providing respiratory therapies such as, but not limited to, constant positive airway pressure (CPAP) and non-invasive ventilation (NIV). More particularly, the present disclosure relates to a headgear connection assembly configured to provide an improved reliability and ease of use for full face, nasal, nasal pillows, cannulas, and other masks or interfaces.

Description of the Related Art

Respiratory masks are used to provide therapies for the treatment of a variety of respiratory conditions including but not limited to CPAP and NIV. The present disclosure will be described in relation to CPAP therapy, however it is to be understood that it may be equally applicable to other therapies.

CPAP therapy is used in the treatment of obstructive sleep apnea (OSA), a condition in which the back of the throat relaxes so much while sleeping that it narrows or entirely blocks the airway. With the constriction or closure of the airway, breathing can stop or become very shallow for a few seconds or longer. CPAP splints open the airway by providing a constant flow of pressurized air to the airway via an interface such as a mask. For the therapy to be effective, a substantially leak free seal ideally should be maintained between the mask and a user's face. In order to achieve this, a headgear system can be used to secure the mask to a user's face. It is commonly known in the art for there to be a headgear connection assembly between a headgear and a mask. The headgear is adapted to engage with a mask such that a sealing cushion is held in position against the patient's face. The headgear often includes a number of headgear straps including an adjustable crown strap for adjusting the size of the headgear to match a range of patient head sizes. The crown strap can include two strap portions that are joined together by a buckle at a centrally located point on the top of a patients head.

Some problems exist with prior headgear connection assemblies. For example, the buckle can be bulky and/or hard on a patient's head. Also, the adjustment can be difficult and ambiguous because there are no markers to indicate how much adjustment has been made to the length of the crown strap. These problems may lead to the mask and headgear system lacking ease of use, reliability and/or comfort, which in turn may result in poor user compliance. Trial and error may be required to refit the headgear and mask every time it is disconnected and reconnected for cleaning. This can be time consuming and inconvenient for patients. Previous designs can also result in uneven adjustment of each of the strap portions that may cause the headgear to sit lopsided on a patient's head, which may result in leaks and compromise the efficacy of the therapy.

There is a continuous need in the art for headgear that is comfortable, fits a wide range of patient's, and is easily adjusted and assembled. It is known in the art for the headgear straps of such headgears to be individually assembled to the frame of the respiratory mask. Headgears assembled in this way can be fiddly and time consuming to fit, size, adjust and assemble, which may influence a patient's compliance with their therapy.

It is an objective of the invention to at least partially address one or more of these problems. Alternatively, it is an object of the inventions to at least provide a useful choice to the public.

BRIEF SUMMARY

An object of the present disclosure is to provide a respiratory mask system which will at least provide the public with a useful choice.

In accordance with certain features, aspects and advantages of at least one of the configurations disclosed herein, a respiratory mask system is provided. The respiratory mask system comprises a frame, a sealing cushion provided to the frame, for sealingly engaging with a patient's face, a headgear to retain the respiratory mask on a patient's head, and a forehead coupler. The forehead coupler comprises a pair of strap connectors, a frame connector, and a flexible linking member, wherein the strap connectors are spaced apart and connected by the flexible linking member, which extends there between.

In some configurations, the headgear comprises at least two forehead straps for connecting to the strap connectors of the forehead coupler.

In some configurations, the forehead straps and forehead coupler connect together to form an adjustable closed loop about a patient's head.

In some configurations, the frame comprises a forehead support and the forehead support comprises a coupler connection.

In some configurations, the coupler connection comprises an aperture for receiving the frame connector.

In some configurations, the frame connector is removably coupled to the coupler connection.

In some configurations, the forehead coupler is removably attached to the frame such that the closed loop remains intact.

In some configurations, the flexible linking member provides independent movement of each strap connector.

In some configurations, the flexible linking member conforms to the shape of the patient's forehead in use.

In some configurations, the frame connector comprises a tongue and the coupler connection comprises a fork, such that a tongue and fork joint is formed between the frame and forehead coupler.

In some configurations, the forehead coupler comprises a T-shaped profile. The T-shaped profile comprises a stem, being formed by the frame connector, and a pair of laterally extending arms, being formed by the strap connectors.

In accordance with certain features, aspects and advantages of another one of the configurations disclosed herein, a respiratory mask system is provided. The respiratory mask system comprises a frame, a sealing cushion, a headgear and a forehead coupler. The frame comprises a forehead support. The sealing cushion is provided to the frame, and is configured to sealingly engage with a patient's face. The headgear has at least two forehead straps and is configured to retain the respiratory mask system on a patient's head. The forehead coupler connects the forehead straps in a closed loop such that the in-use length of the straps is adjustable, and couples the headgear to the forehead support such that the strap connectors can flex in more than one direction relative to the frame.

In accordance with certain features, aspects and advantages of yet another one of the configurations disclosed herein, a connector system for connecting a headgear to a respiratory mask is provided. The connector system comprises a frame connected to the respiratory mask, and first and second forehead straps attached to the headgear. The first and second forehead straps are attached to the frame to connect the headgear to the respiratory mask.

In accordance with certain features, aspects and advantages of yet another one of the configurations disclosed herein, a connector system for fastening first and second forehead straps of a headgear to a frame of a respiratory mask is provided. The connector system comprises a slot disposed on the frame, and a forehead strap connector having a strap connecting portion and a frame connector portion. The strap connecting portion is connected to the first and the second forehead straps, and the frame connector portion extends from the strap connecting portion. The frame connector portion is positioned within the slot and the frame is retained between the frame connector portion and the strap connecting portion such that the headgear is attached to the frame. In some configurations, the strap connecting portion is attached to at least one strap connector through which the first and second forehead straps are attached to the forehead strap connector.

In some configurations, the strap connecting portion includes slots that extend through the strap connecting portion, through which the first and second forehead straps are attached to the forehead strap connector.

In some configurations, the strap connecting portion and the frame connector portion of the forehead strap connector are integrally formed from a fabric strip, wherein the frame connector portion is formed by overlapping and fusing or otherwise connecting a portion of the fabric strip onto itself.

In some configurations, an inlet portion of the slot has a width that is narrower than a thickness of the strap connecting portion.

In accordance with certain features, aspects and advantages of still yet another one of the configurations disclosed herein, a connector system for fastening first and second forehead straps of a headgear to a frame of a respiratory mask is provided. The connector system comprises a connection portion disposed on the frame, and a forehead strap connector. The forehead strap connector further comprises slots extending through the forehead strap connector, the first and second forehead straps being attached to the forehead strap connector via the slots, and a fabric loop, the fabric loop being attached to the forehead strap connector between the slots and extending outward from the forehead strap connector. The fabric loop is fastened onto the connection portion such that the headgear is attached to the frame.

In some configurations, the forehead strap connector has a center column that defines portions of each slot, wherein the fabric loop is a closed loop and the center column is positioned within the fabric loop.

In some configurations, the fabric loop is fastened to one side of the forehead strap connector, extends through the forehead strap connector, and extends outward from an opposite side of the forehead strap connector.

In some configurations, the forehead strap connector is configured to be separable into a first portion and a second portion, the first portion including a first slot and having an end of the fabric loop attached to the first portion, the second portion including a second slot and having an end of the fabric loop attached to the second portion, wherein the first portion is configured to be removably fastened to the second portion, and wherein the fabric loop is a closed loop when the first portion is fastened to the second portion, and an open loop when the first portion is unfastened from the second portion.

In some configurations, a protrusion extends outward from the first portion and a hole is recessed into the second portion, wherein the protrusion is positioned into the hole to fasten the first portion and the second portion.

In some configurations, the connection portion is an elongate post.

In some configurations, the connection portion is a gap, and the fabric loop is positioned within the gap to fasten the headgear to the frame.

In accordance with certain features, aspects and advantages of another one of the configurations disclosed herein, a connector system for fastening first and second forehead straps of a headgear to a frame of a respiratory mask is provided. The connector system comprises a connection portion disposed on the frame, and a forehead strap connector. The forehead strap connector further comprises a first fabric layer joined with a second fabric layer, the first and second fabric layers being bonded to each other at their ends, a connection cavity positioned between the first and second fabric layers, and slots positioned on and extending through the ends of the first and second fabric layers. The first and second forehead straps are attached to the forehead strap connector via the slots and the forehead strap connector is positioned onto the connection portion such that the headgear is attached to the frame.

In some configurations, the forehead strap connector further comprises over-moulded slot liners formed around a perimeter of the slot straps and extending through the first and second fabric layers, wherein the over-moulded slot liners bond the first and second fabric layers at their ends.

In some configurations, the flexibility of the first and second fabric layers vary between planes.

In some configurations, the first and second fabric layers are more flexible in a direction that is substantially perpendicular to the thickness of the fabric than in a direction that is parallel to the thickness.

In some configurations, the connection portion is a gap, and the fabric loop is positioned within the gap to fasten the headgear to the frame.

In accordance with certain features, aspects and advantages of another one of the configurations disclosed herein, a connector system for fastening first and second forehead straps of a headgear to a frame of a respiratory mask is provided. The connector system comprises a connection portion disposed on the frame, and a forehead strap connector. The forehead strap connector further comprises a first fabric layer joined with a second fabric layer, the first and second fabric layers being bonded to each other at their ends, a connection cavity positioned between the first and second fabric layers, and slots positioned on and extending through the ends of the first and second fabric layers. The first and second forehead straps are attached to the forehead strap connector via the slots and the forehead strap connector is positioned onto the connection portion such that the headgear is attached to the frame.

In some configurations, the forehead strap connector further comprises over-moulded slot liners formed around a perimeter of the slot straps and extending through the first and second fabric layers, wherein the over-moulded slot liners bond the first and second fabric layers at their ends.

In some configurations, the flexibility of the first and second fabric layers vary between planes.

In some configurations, the first and second fabric layers are more flexible in a direction that is substantially perpendicular to the thickness of the fabric than in a direction that is parallel to the thickness.

In accordance with certain features, aspects and advantages of yet another one of the configurations disclosed herein, a connector system for fastening a forehead band of a headgear to a frame of a respiratory mask is provided. The connector system comprises slots disposed on the frame, and a fastener disposed on the forehead band. The forehead band extends through the slots and the forehead band is overlapped and fastened onto itself to fasten the headgear to the frame.

In some configurations, the fastener is a hook and loop fastener.

In accordance with certain features, aspects and advantages of yet another one of the configurations disclosed herein, connector system for removably connecting first and second forehead straps of a headgear to a frame is provided. The connector system comprises a hook connector portion disposed on the frame and a strap connector portion connected to the first and second forehead straps. The hook connector portion further includes a shank connected to the frame, a bend connected to the shank, a return arm connected to the bend, and a throat portion positioned between the shank and the return arm. The strap connector portion has an attachment portion configured to be removably inserted into the throat portion. The attachment portion is sandwiched between the shank and the return arm such that the strap connector portion is removably attached to the hook connection portion.

In some configurations, the hook connector portion includes a rib extending into the throat portion from the shank toward the return arm. The strap connector portion includes a rib slot positioned on the attachment portion. The rib is positioned within the rib slot when the strap connector portion is attached to the hook connection portion and contact between the rib and the rib slot obstructs rotation of the strap connector relative to the frame.

In some configurations, the rib contacts the bend and the return arm.

In some configurations, the rib is separated from the bend and the return arm.

In some configurations, the attachment portion includes a blocking portion positioned on one side of the attachment portion. The blocking portion contacts the return arm and obstructs the strap connector portion from being inserted into the throat portion when the blocking portion faces the return arm.

In some configurations, an end portion of the return arm extends towards the shank to define a throat opening between the return arm and the shank. A width of the throat opening between the return arm and the shank is narrower than a width of the throat between the return arm and the shank.

In some configurations, a thickness of a first end of the attachment portion is less than the width of the throat opening, and a thickness of a second end of the attachment portion is greater than double the width of the throat opening.

In some configurations, the strap connector includes slots through which the straps are connected.

In accordance with certain features, aspects and advantages of yet another one of the configurations disclosed herein, a connector system for connecting first and second forehead straps of a headgear to a frame is provided. The connector system includes a female coupling portion disposed on the universal frame and having a receiving portion, and a male coupling portion. The male coupling portion includes slots through which the first and second forehead straps are attached, and an attachment portion positioned between the slots. The attachment portion of the male coupling portion is positioned within the receiving portion of the female coupling portion to connect the first and second forehead straps to the frame.

In some configurations, the frame is a universal frame configured to fit a plurality of respiratory mask sizes.

In some configurations, a position of the attachment portion with respect to the slots varies between a smaller-sized respiratory mask and a larger-sized respiratory mask.

In some configurations, comparatively, the position of the attachment portion with respect to the slots for the smaller-sized respiratory mask is positioned vertically higher than the attachment portion with respect to the slots for the larger-sized respiratory mask such that the slots for the smaller-sized respiratory mask are positioned lower with respect to the universal frame than the slots for the larger-sized respiratory mask.

In accordance with certain features, aspects and advantages of yet another one of the configurations disclosed herein, a method of using a universal frame for different respiratory mask sizes is provided. The universal frame is removably attachable to a connector element. The connector element is attached to first and second forehead straps of a headgear and has an attachment portion that attaches to the universal frame. The method includes providing different connector elements for the different respiratory mask sizes, and varying the position of the attachment portion on the different connector elements according to respiratory mask size.

In some configurations, varying the position of the attachment portion on the different connector elements according to respiratory mask size includes positioning the attachment portion of a smaller-sized respiratory mask vertically higher with respect to the universal frame than the attachment portion of a larger-sized respiratory mask such that the first and second forehead straps for the smaller-sized respiratory mask are positioned lower with respect to the universal frame than the first and second forehead straps for the larger-sized respiratory mask.

In some configurations, the connector element has slots through which the first and second forehead straps are attached.

In accordance with certain features, aspects and advantages of yet another one of the configurations disclosed herein, connector system for removably fastening a headgear to a frame of a respiratory mask that allows forehead straps of the headgear to be connected and disconnected from the frame without unfastening the top straps is provided. The connector system comprises a fastener portion disposed on the frame, and a forehead strap connector connected to the forehead straps. The forehead strap connector further comprises a fastener engaging portion disposed on the forehead strap connector and configured to selectively engage the fastener portion to connect and disconnect the top straps to the frame.

In some configurations, the fastener portion includes an elongate post and the fastener engaging portion comprises a flexible loop, wherein the flexible loop is removably fitted over the post to connect and disconnect the top straps to the frame.

In some configurations, the fastener portion includes a hook portion and the fastener engaging portion comprises a crossbar, wherein the crossbar is removably fitted within the hook portion to connect and disconnect the top straps to the frame.

In some configurations, the fastener portion includes a slot and the fastener engaging portion comprises a neck portion extending from the forehead strap connector and a head portion positioned on a free end of the neck portion, wherein the neck portion is removably positioned within the slot to connect and disconnect the top straps to the frame.

In accordance with certain features, aspects and advantages of yet another one of the configurations disclosed herein, a method for removably fastening a headgear to a frame of a respiratory mask that allows forehead straps of the headgear to be connected and disconnected from the frame without unfastening the forehead straps is provided. The method comprises providing a forehead strap connector that is removably fastenable to the frame, attaching the forehead straps to the forehead strap connector, fastening the forehead strap connector to the frame to connect the forehead straps to the frame, and unfastening the forehead strap connector from the frame to disconnect the forehead straps from the frame.

In accordance with certain features, aspects and advantages of yet another one of the configurations disclosed herein, a top strap connection assembly for providing incremental length adjustment to a top strap of a headgear is provided. The top strap connection assembly includes a female strap portion attached to the headgear and a male strap portion attached to the headgear. The female strap portion includes an aperture extending through the female strap portion, and a first fastener portion positioned on an inner surface of the female strap between the aperture and an end of the female strap portion. The male strap portion includes a plurality of notches positioned along the length of the male strap portion on outer edges of the male strap portion, and a second fastener portion positioned on an inner surface of the male strap portion between the plurality of notches and an end of the male strap portion. The male strap is positioned within the aperture such that the plurality of notches engages the aperture. The first fastener portion is fastened to an outer surface of the male strap portion and the second fastener portion is fastened to an outer surface of the female strap portion.

In some configurations, the first and second fasteners portions are hook portions of a hook and loop type fastener.

In some configurations, the first and second fastener portions include a three-dimensional projection that protrudes from the inner surfaces of the female and male strap portions.

In some configurations, the aperture extends through a portion of the first fastener portion.

In some configurations, a width of the female strap portion is approximately equal to a width of the male strap portion.

In some configurations, the aperture has a straight side and a curved side.

In some configurations, a length of a perimeter of the curved side is substantially equal to the width of the male strap portion.

In some configurations, the plurality of notches on the outer edges of the male strap portion are arranged in aligned pairs and the male strap portion includes a width between each aligned pair of notches, and wherein the width between each aligned pair of notches is substantially equal to a length of the straight side of the aperture.

In some configurations, the aperture has a height extending along the length of the male strap portion and the height of the aperture is less than the length of the straight side of the aperture.

In some configurations, the width of the male strap portion is approximately between 1.5 and 2.5 times greater than a length of the straight side of the aperture.

In some configurations, the aperture has a semicircular shape and includes a straight side extending perpendicular to a longitudinal axis of the female strap portion.

In accordance with certain features, aspects and advantages of yet another one of the configurations disclosed herein, there is provided a headgear assembly for a respiratory mask, the headgear including a male strap portion and a female strap portion. The free end portion of the female strap portion includes an aperture through which the free end portion of the male strap portion passes and the male strap portion engages the aperture to allow incremental adjustment of the overall strap length. In some embodiments, the male strap portion comprises a plurality of notches that engage the aperture of the female strap portion.

In some embodiments, the headgear assembly comprises a top strap having a male strap portion and a female strap portion. The female strap portion comprises a first free end having an aperture extending therethrough. In some embodiments the aperture extends through a length of the first free end of the strap, including extending through the inner surface and the outer surface. The female strap portion also comprises a first fastener portion supported by the inner surface of the female strap at the free end. The male strap portion comprises a second free end and a plurality of notches adjacent the second free end. The notches are configured to engage the aperture and limit movement of the male strap portion within the aperture when the male strap portion is flattened. The male strap portion can also comprise a second fastener supported by the inner surface of the male strap portion at its free end.

In some preferred embodiments, the headgear assembly comprises first and second fasteners that are hook portions of a hook and loop type fastener. In some preferred embodiments, each of the first and second free ends includes a three dimensional projection.

In some preferred embodiments, the headgear assembly includes a female strap portion having an aperture with one straight side and one curved side. In some preferred embodiments, the aperture extends through a portion of the first fastener portion.

Further aspects of the presently disclosed subject matter, which should be considered in all its novel aspects, will become apparent to those skilled in the art upon reading of the following description which provides at least one example of a practical application of the invention.

BRIEF DESCRIPTION OF THE DRAWINGS

FIG. 13A is a side view of a coupler connection assembled to the forehead coupler of FIGS. 9A, 9B and 9C.

FIG. 13B is a side view of the coupler connection of FIG. 13A.

FIG. 15A is a front view of a coupler connection disconnected from the forehead coupler of FIGS. 9A, 9B and 9C.

FIG. 15B is a perspective view of the coupler connection of FIG. 15A connected to the forehead coupler of FIGS. 9A, 9B and 9C.

FIG. 20A is a perspective view of a forehead coupler assembled to a coupler connection.

FIG. 20B is a perspective view of the forehead coupler of FIG. 20A.

FIG. 20C is a front view of the forehead coupler of FIG. 20A.

FIG. 20D is a rear view of the forehead coupler of FIG. 20A.

FIG. 20E is a cross-sectional view of the forehead coupler of FIG. 20A.

FIG. 20F is a top-down view of the forehead coupler of FIG. 20A.

FIG. 20I is a cross-sectional side view of the frame and the forehead coupler of FIGS. 20A to 20H.

FIG. 20J is a cross-sectional side view of the forehead coupler inserted into the frame of FIGS. 20A to 20H.

FIG. 21A is a front view of a universal frame connected to a size small forehead coupler.

FIG. 21B is a front view of the universal frame connected to a size medium/large forehead coupler.

FIG. 24A is a side view of the size medium forehead coupler of FIG. 21B.

FIG. 24B is a side view of the size small forehead coupler of FIG. 21A.

FIG. 25A is a side cross-sectional view of the size medium forehead coupler of FIG. 21B.

FIG. 25B is a side cross-sectional view of the size small forehead coupler of FIG. 21A.

DETAILED DESCRIPTION

The respiratory mask system of the preferred and alternative forms described herein provides improvements in the delivery of CPAP therapy. In particular a respiratory mask system, is described which may provide improved ease of use in relation to the fitment, sizing adjustment and assembly of the respiratory mask, when compared with the prior art. It will be appreciated that the respiratory mask as described can be used in respiratory care generally or with a ventilator but will be described for illustration with reference to use in a humidified CPAP system. It will also be appreciated that the preferred and alternative forms described can be applied to any form of respiratory mask including, but not limited to, full face masks sealing around the patient's nose and mouth, and nasal masks sealing around the patient's nose.

Figure 1:
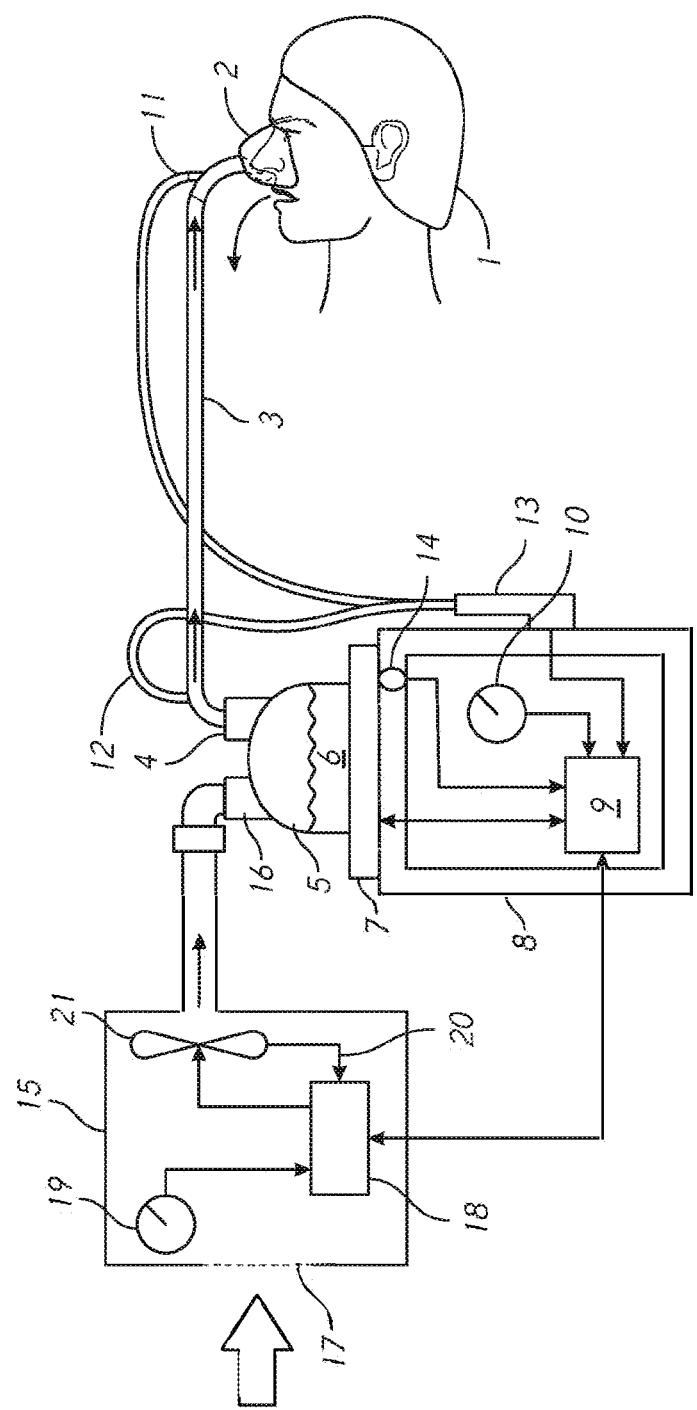
FIG. 1 is a block diagram of a system for providing heated humidified gases to a user, such as a continuous positive airway pressure system as might be used in conjunction with the respiratory mask of the present disclosure.

With reference to FIG. 1 a humidified Continuous Positive Airway Pressure (CPAP) system is shown in which a patient 1 is receiving humidified and pressurised breathable gases through a respiratory mask 2 connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy.

Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 5 is preferably formed from a plastics material and may have a highly heat conductive base (for example an aluminum base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as a user input interface or dial 10 through which a user of the device may, for example, set a predetermined required value (pre-set value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energize heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply or blower 15 which enters the chamber through inlet 16. Exhaled gases from the patient's mouth are passed directly to ambient surroundings in FIG. 1.

Blower 15 is provided with a variable pressure regulator or with a variable speed fan 21 which draws air or other gases through blower inlet 17. The speed of variable speed fan 21 is controlled by electronic controller 18 (or alternatively the function of controller 18 could be carried out by controller 9). The controller may control the fan speed or regulated pressure according to any useful criteria. For example the controller may respond to inputs from controller 9 and a user set predetermined required value (pre-set value) of pressure or fan speed via dial 19.

Figure 2:
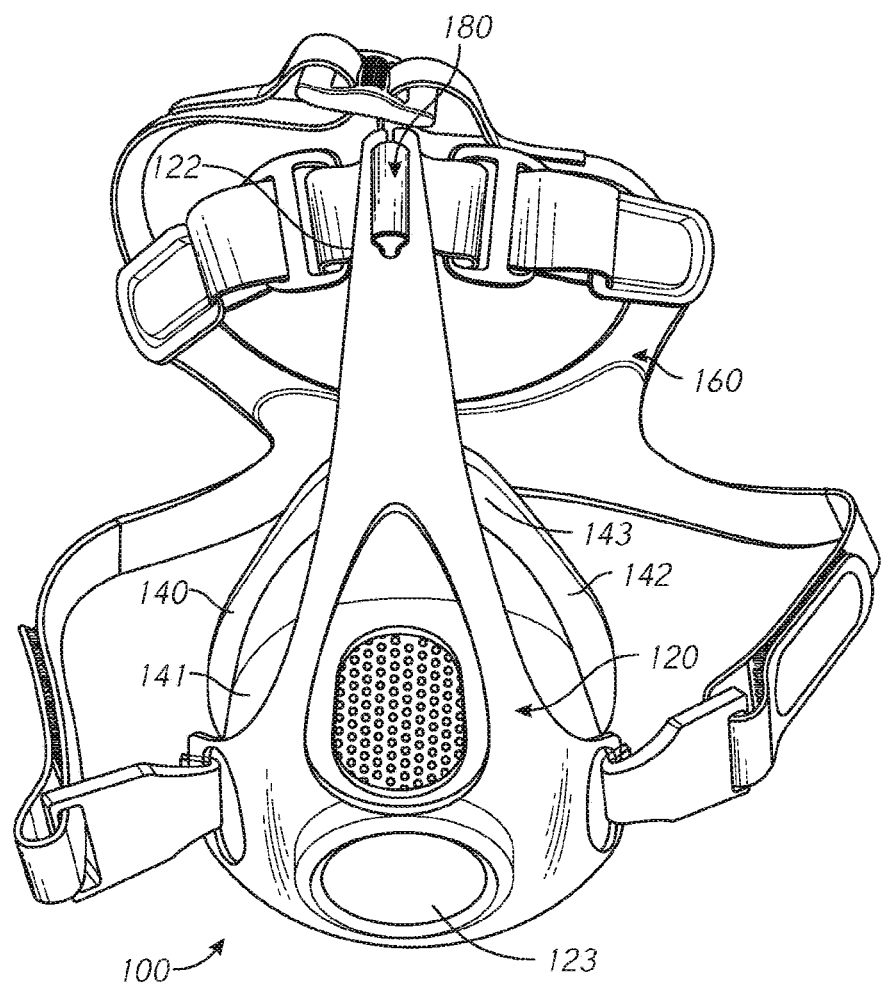
FIG. 2 is a front perspective view of a respiratory mask system that is arranged and configured in accordance with certain features, aspects and advantages of the present disclosure.

FIG. 2 shows a non-limiting exemplary embodiment of the respiratory mask system 100 of the present disclosure, configured to provide a supply of pressurized breathable gases to a patient's airway. The respiratory mask system 100 comprises a frame 120, sealing cushion 140, headgear 160 and a forehead coupler 180.

Figure 3:
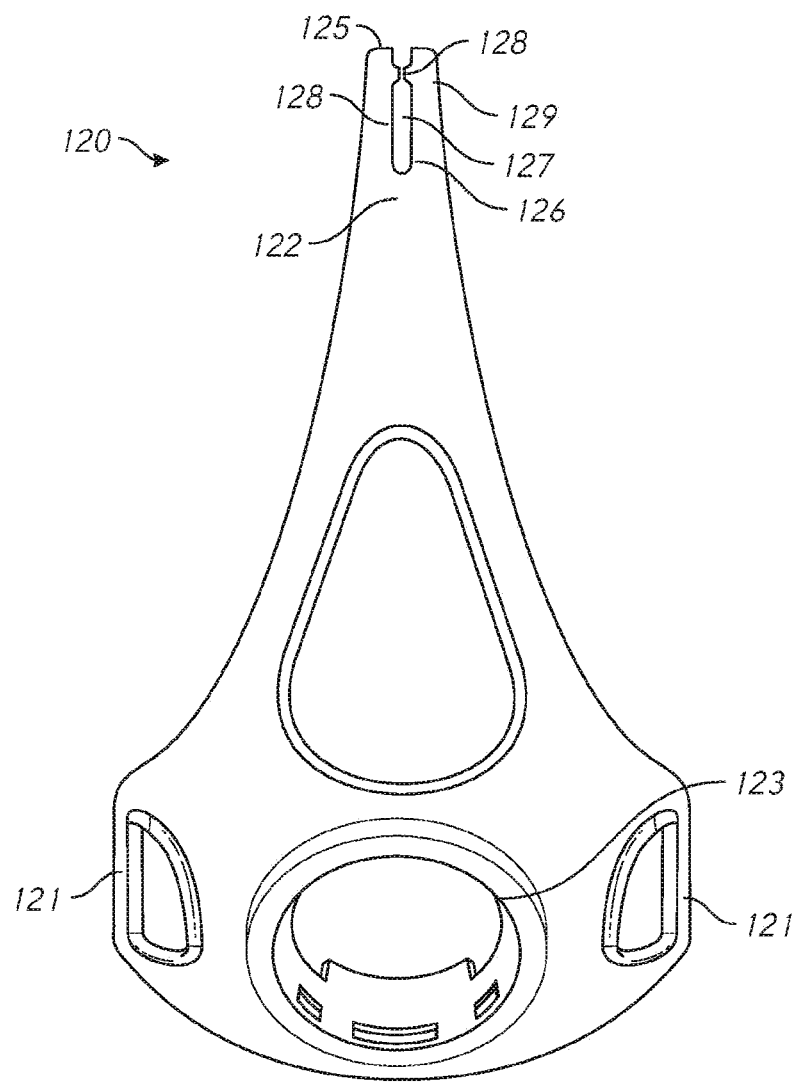
FIG. 3 is a front view of the frame of FIG. 2.

As shown in FIG. 3 the frame 120 comprises a substantially triangular component having two headgear connections 121 (forming the lower points of the triangle) and a forehead support 122 (forming the upper point of the triangle). The frame 120 further comprises a central gas inlet 123 through which a supply of pressurized breathable gases can be delivered to the patient's airways, and a sealing cushion connection 124 (not shown). The frame 120 is configured to act as an interfacing component and connect the sealing cushion 140, headgear 160 and forehead coupler 180 together.

The forehead support 122 comprises an elongate member that in use extends upwardly, away from the headgear connections, towards the patient's forehead and terminates at a distal end 125. A coupler connection 126 is located at the distal end. The coupler connection 126 comprises an aperture 127 in the form of an elongate slot, wherein the side of the aperture that is closest to the distal end has an opening 128 extending from it, such that the aperture is not fully enclosed. The aperture 127 and opening 128 form a fork, having two prongs 129, in the forehead support 122. The opening 128 is configured to provide a narrow path through which the forehead coupler 180 can be connected to the coupler connection 126.

The sealing cushion 140 comprises an integrally formed seal housing 141 and flexible cushion 142, as shown in FIG. 2. The seal housing 141 is configured to provide a substantially rigid breathing chamber about the patient's nose and/or mouth and attach to the sealing cushion connection 124 of the frame 120. The flexible cushion 142 is configured to engage a patient's face such that a substantially airtight seal is formed about the patient's nose, mouth or nose and mouth. The flexible cushion 142 can be made from silicone, thermoplastic elastomer or any other appropriate material capable of at least partially conforming to the facial geometry of the patient. The flexible cushion 142 comprises a rolling bridge 143 located proximal to the patient's nasal bridge, in use. The rolling bridge 143 is configured to allow an upper portion of the flexible cushion to roll during hinging movement of the upper portion relative to a lower portion of the flexible cushion, as described in US2014/0096774A1, which is hereby incorporated by reference herein in its entirety.

Figure 4:
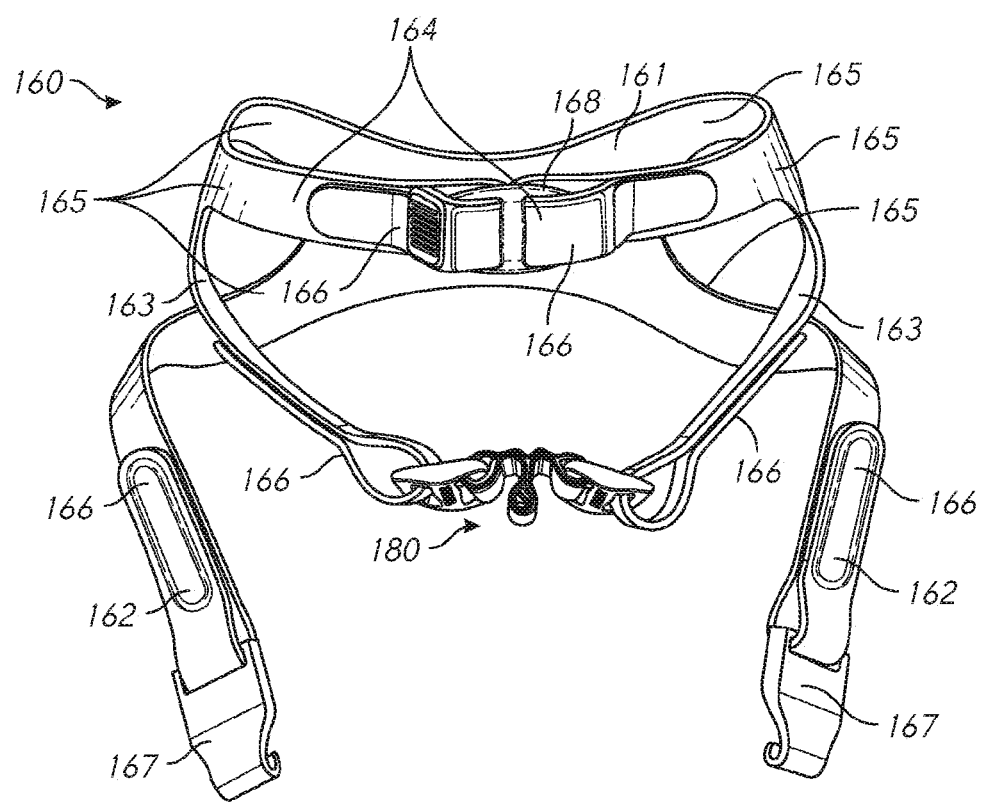
FIG. 4 is a perspective view of the headgear and forehead coupler, of FIG. 2, assembled together.

The headgear 160 is configured to extend around and retains the respiratory mask system 100 on the patient's head, in use. As shown in FIG. 4 the headgear comprises a rear portion 161, two side straps 162, two forehead straps 163 and two top straps 164. In alternative embodiments there may be more or less side, forehead or top straps 162, 163, or 164. The side, forehead and top straps 162, 163 and 164 all have a fixed end 165 and a free end 166. The side straps 162 and forehead straps 163 extend laterally from the fixed ends 165 that connect to the rear portion 161, and the top straps 164 extend at an angle from the forehead straps 163. The side straps 162 connect to the headgear connections 121 of the frame 120 via a clip 167 and the forehead straps 163 connect to the forehead coupler 180. The top straps 164 are configured to pass over the top of a patient's head, in use, and are connected together via a buckle 168. The size of the headgear can be adjusted by folding the side, forehead or top straps 162, 163, or 164 back on themselves and securing the free ends 166 in place by means such as, but not limited to, hook and loop fastener, clips or clasps. This allows the in-use length of each of the side, forehead or top strap 162, 163, or 164 to be adjusted. As used herein the term "in-use length" shall mean the length of any of the side, forehead and/or top straps 162, 163, and/or 164 between the fixed end 165 and the point at which they connect with another component such as the buckle 168, clip 167 or forehead coupler 180. In alternative embodiments there may be a single fixed length top strap. The headgear can be made of a layered fabric such as Breath-o-Prene™ or any other appropriate material, and may be elastic and/or inelastic.

The forehead coupler 180 is configured to removably couple the forehead straps 163 and frame 120 together. When coupled together, the forehead straps 163 and forehead coupler 180 form a closed loop that is configured to extend around the patient's head and across their forehead, wherein the forehead coupler 180 is positioned near the center of the patient's forehead. The forehead coupler 180 is configured such that when it is removed from the frame 120 the closed loop remains intact. That is, the forehead coupler 180 allows a user to connect or disconnect the top strap from the forehead support of the frame 120 in a single action while still maintaining the loop tightness setting/connection of the top strap. This is beneficial as it allows the patient to remove the respiratory mask system 100 without altering the fit of the forehead straps, which improves ease of use and may lead to improved compliance with their therapy.

Figure 5A:
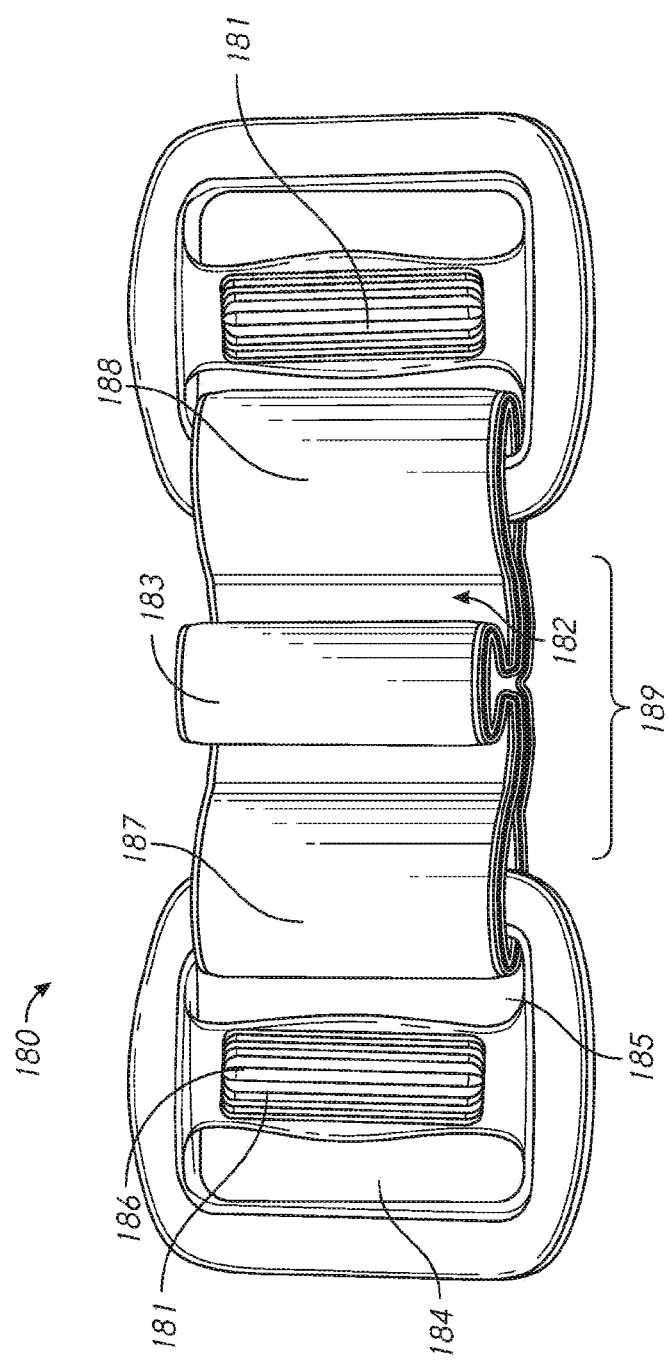
FIG. 5A is a front view of the forehead coupler of FIG. 2.
Figure 5B:
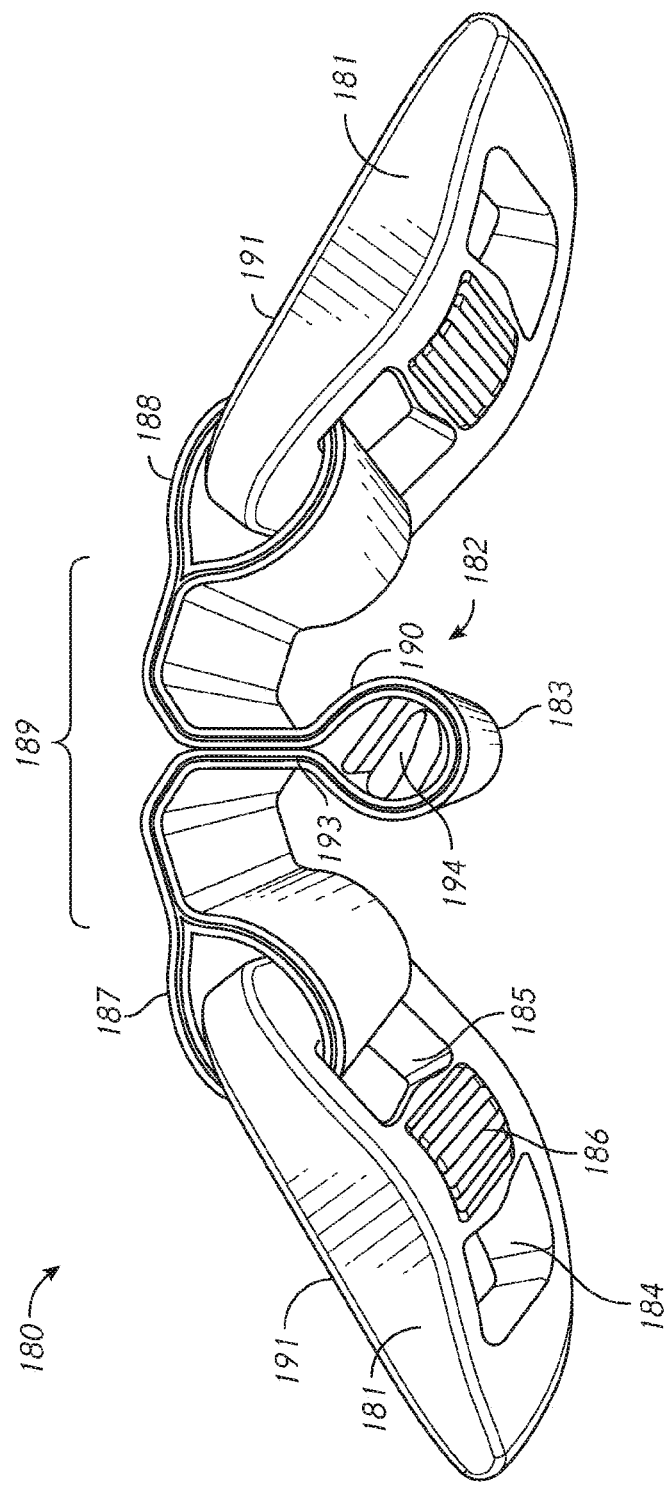
FIG. 5B is a top view of the forehead coupler of FIG. 2.

As shown in FIGS. 5A and 5B the forehead coupler 180 comprises a pair of strap connectors 181, a flexible linking member 182 and a frame connector 183. The strap connectors 181 comprise a substantially rigid plastic component having first and second strap slots 184 and 185 symmetrically separated by a central post 186. The strap slots are substantially rectangular in shape and are configured to receive a strap. The first strap slot 184 is configured to receive one of the forehead straps 163 and the second strap slot 185 is configured to receive one end of the flexible linking member 182. The size of the closed loop can be adjusted, to match the head circumference of the patient, by adjusting the in-use length of the forehead straps 163, as described above.

The flexible linking member 182 comprises a fabric strap having a first end 187, second end 188 and central portion 189. The first and second ends 187 and 188 pass through the second strap slots 185 of the strap connectors 181, and fold back over to be permanently secured to the central portion 189. The permanent securement can be achieved by means such as, but not limited to, sewing, adhesive or welding. The central portion 189 comprises the frame connector 183 as an integrally formed component which is configured to be removably coupled to the coupler connection 126 and allow the strap connectors 181 to flex independently of one another and the frame connector 183 in more than one direction. The fabric that the flexible linking member 182 is made of is substantially inelastic, such that the size of the closed loop and headgear 160 does not alter unintentionally during use. The flexibility of the fabric allows the flexible linking member 182 and thus the forehead coupler 180 to twist and bend in order to conform to the shape of the patient's forehead and provide a soft or cushioned interface between the frame 120 and the patient. This may be advantageous in improving the fit of the respiratory mask system 100 and the patient's comfort. In alternative embodiments the flexible linking member 182 may be made from a plastic film or strap that is flexible and substantially inelastic.

The forehead coupler 180 is configured to have a T-shaped profile as shown in FIG. 5B. The T-shaped profile comprises a stem 190 and a pair of arms 191. The stem 190 is formed by the frame connector 183 and the arms 191 are formed by the strap connectors which extend laterally from the stem 190.

The frame connector 183 is integrally formed in the central portion 189 of the flexible linking member 182. It is formed by the flexible linking member 182 being folded in half and permanently joined between the folded layers, to form a linking portion 193. The linking portion 193 is configured to pass through the opening of the coupler connection 126, and can be formed by means such as, but not limited to, welding, sewing or adhesives. Preferably the layers of fabric in the linking portion 193 are compressed by the joining means, such that they are thinner and more rigid than the fabric of the flexible linking member 182, to enable the linking portion 193 to pass easily through the opening 128 of the coupler connection 126. The linking portion 193 is offset from the crease of the fold, such that a loop 194 (also referred to as a head portion herein) is formed in the flexible linking member 182. The loop 194 has a diameter that is greater than the width of the aperture 127 in the coupler connection 126 of the frame 120 and may be filled with a material that reduces the compressibility of the loop 194, such that it cannot be pulled through the aperture 127.

Figure 6:
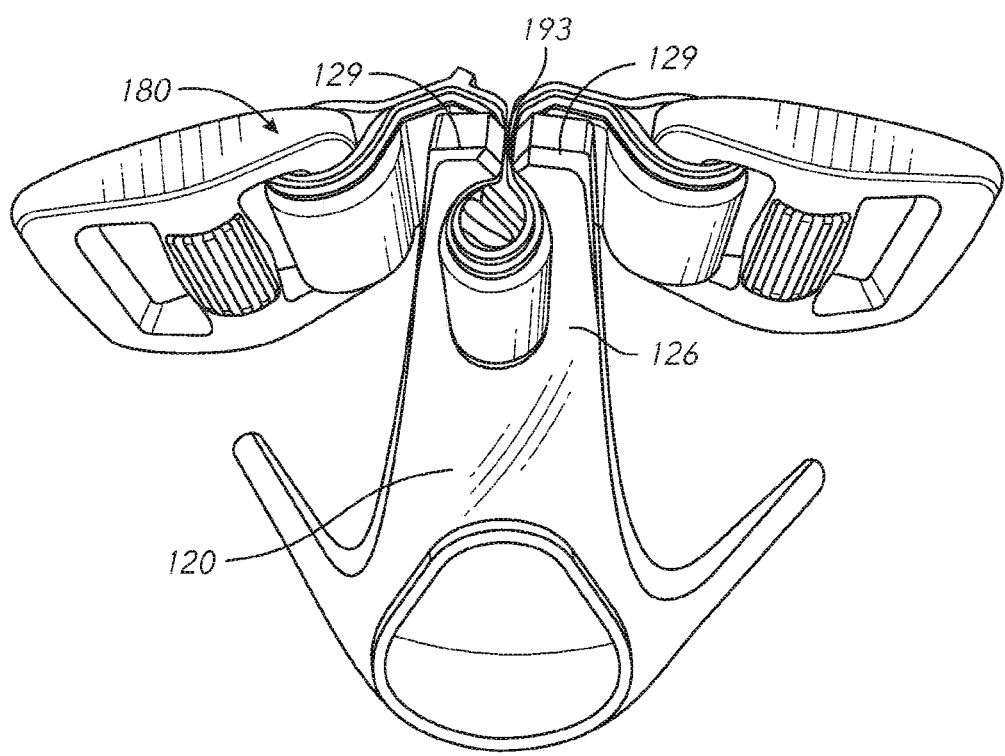
FIG. 6 is a top perspective view of the frame and forehead coupler, of FIG. 2, assembled together.

The linking portion 193 forms a tongue or neck portion which is configured to join with the coupler connection 126 of the frame 120 in a tongue and fork joint, as shown in FIG. 6. The prongs 129 of the coupler connection 126 are configured to deflect when the linking portion 193 passes between them. The width of the opening 128 is narrower than the thickness of the linking portion 193 such that there is a friction force that discourages the forehead coupler 180 from becoming unintentionally detached from the frame 120.

In an alternative embodiment the strap connectors 181 may comprise only a first strap slot 184, through which the forehead straps 163 are connected. The strap connectors 181 can be permanently connected to the first and second ends 187 and 188 of the flexible linking member 182, by means such as, but not limited to, over-moulding, welding, adhesives or sewing.

Figure 7:
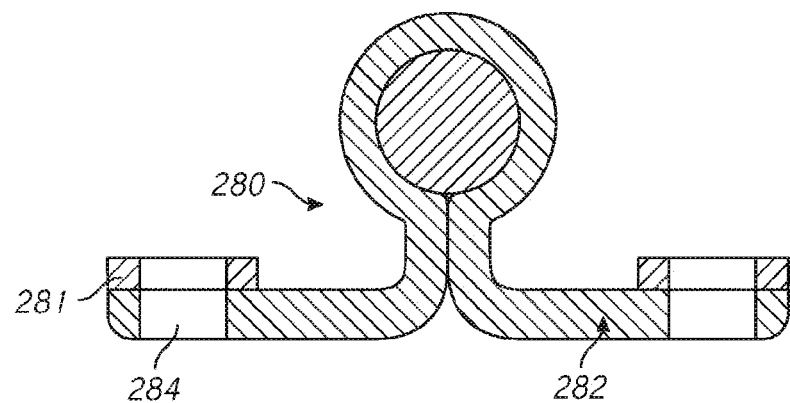
FIG. 7 is a top view of a forehead coupler.

FIG. 7 shows an alternative embodiment of the previously described forehead coupler 180. The embodiment of FIG. 7 comprises a forehead coupler 280 having integrally formed strap connectors 281. The strap connectors 281 comprise a plastic component that is over-moulded or welded to the flexible linking member 282. A strap slot 284, through which the forehead straps 163 pass, extends through both the strap connector 281 and the flexible linking member 282. The strap connectors 281 are configured to provide the flexible linking member 282 with structure around the strap slots 284, such that it is easy to connect and adjust the in-use length of the forehead straps 163. The strap connector 281 minimizes deformation of the strap slot 284 whilst reducing the overall bulk of the forehead coupler 280.

Figure 8:
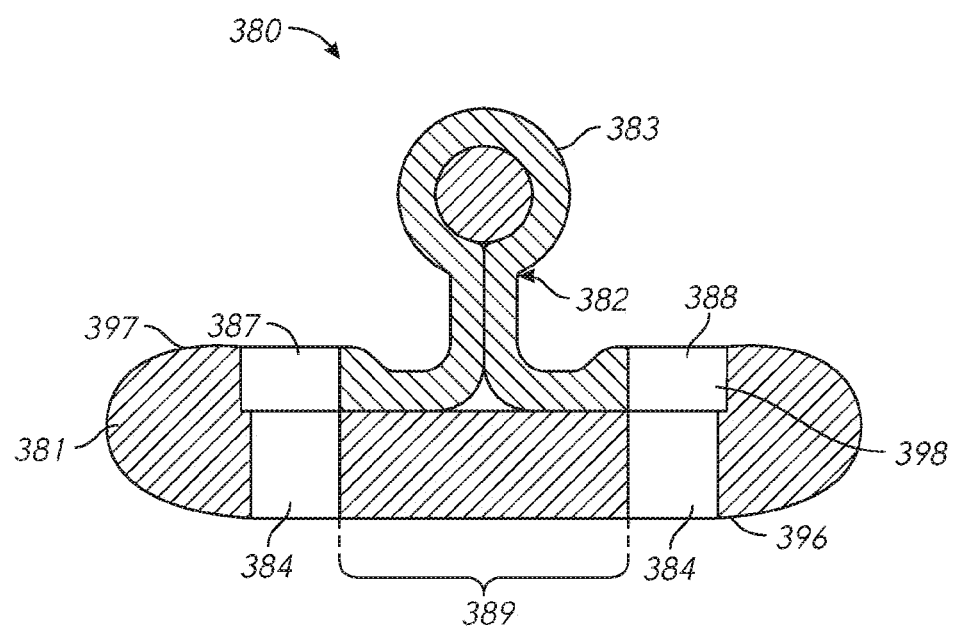
FIG. 8 is a top view of a forehead coupler.

Another non-limiting exemplary embodiment of a forehead coupler 380 is shown in FIG. 8. The forehead coupler 380 comprises a strap connector 381 and a flexible linking member 382, which are permanently joined. The flexible linking member 382 comprises a frame connector 383, first and second ends 387 and 388 and a central portion 389. It is configured to provide a flexible connection between the frame connector 383 and the strap connector 381. The frame connector 383 is substantially the same as described in relation to previous embodiments. The first and second ends 387 and 388 along with the central portion 389 are permanently connected to the strap connector 381 by means such as, but not limited to, over-moulding, welding or adhesives.

The strap connector comprises an elongate component having an inner surface 396 and an outer surface 397, and a strap slot 384 located at each end. The inner surface 396 is configured to sit near or against the patient's forehead in use; correspondingly the outer surface 397 is configured to be distal to the patient's forehead. The outer surface 397 comprises a recess 398, which is configured to receive the first and second ends 387 and 388 and the central portion 389 of the flexible linking member 382, in a permanent connection as previously described. The strap connector 381 is made from a substantially inelastic plastic, which may or may not be flexible. When assembled in a respiratory mask system 100 the forehead straps 163 are connected together in a closed loop by the forehead coupler 380. In an embodiment wherein the strap connector 381 is made of an inflexible material, the ends of the forehead straps 163 are held in a fixed position relative to each other but are capable of flexing relative to the frame connector 383 and frame 120. The strap slots 384 are configured to extend through both the strap connector 381 and the flexible linking member 382.

Figure 9A:
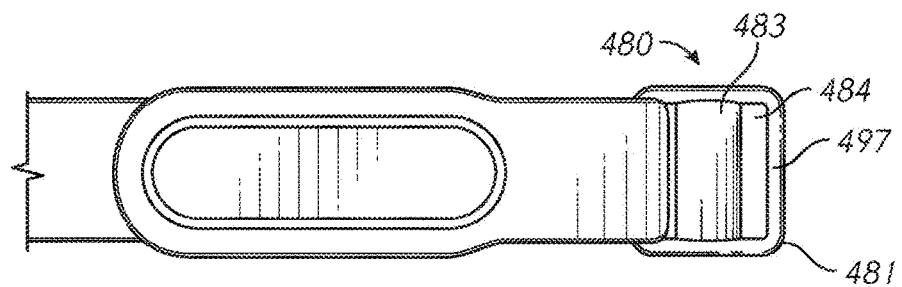
FIG. 9A is a front view of a forehead coupler assembled to a forehead strap.
Figure 9B:
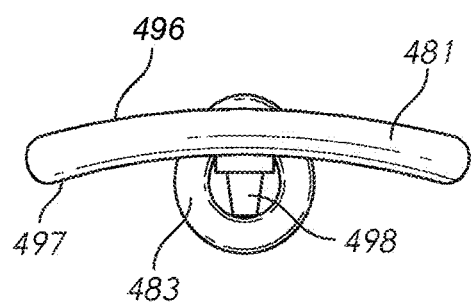
FIG. 9B is a top view of the forehead coupler of FIG. 9A.
Figure 9C:
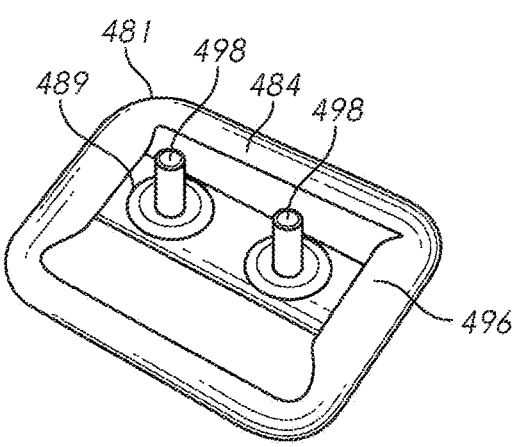
FIG. 9C is a rear perspective view of the strap connector of FIGS. 9A and 9B.

FIGS. 9A, 9B and 9C show a further embodiment of a forehead coupler 480. The forehead coupler 480 comprises a strap connector 481 and a frame connector 483, which are permanently attached to each other. The strap connector 481 comprises a substantially rectangular buckle having a back side 496, front side 497 and a strap slot 484 on each lateral side, wherein the strap slots 484 are separated by a central post 489. The front side 497 is configured to sit away from the patient's forehead in use, whereas the back side 496 is configured to contact or sit nearer the patient's forehead. The strap slots 484 are configured to receive the forehead straps 163 such that the in-use length is adjustable as described in relation to previous embodiments. When viewed end-on along the length of the strap slots 484 the strap connector 481 is curved such that front side 497 is concave. On the back side 496 the central post 489 comprises one or more rivets 498 configured to secure the frame connector 483 to the strap connector 481.

The frame connector 483 comprises a loop made from a fabric strap that is configured to extend around the central post 489, such that there is a gap between the front side 497 of the central post 489 and the inside of the frame connector 483. The ends of the strap are overlapped and secured to the back side 496 of the strap connector 481 by the one or more rivets 498. The ends of the fabric strap may comprise pilot holes (not shown) through which the rivets 498 pass before being deformed to permanently secure the frame connector 483 in place. In some embodiments the rivets 498 may be deformed by a welding process such that they fuse to the material of the frame connector 483. The frame connector 483 is configured to receive and retain a part of the forehead support 122 of the frame 120.

Figure 10A:
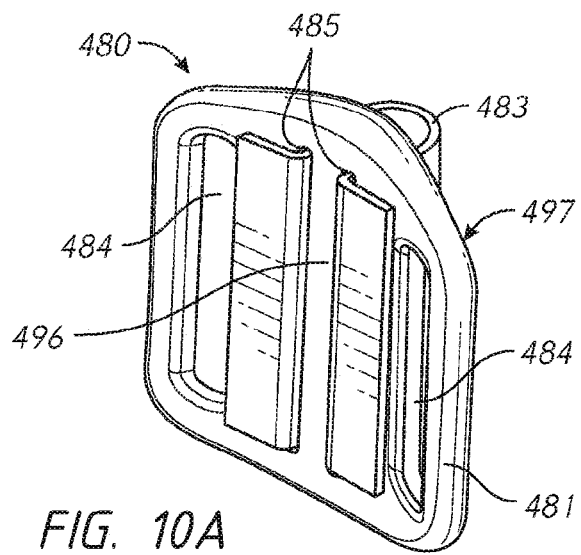
FIG. 10A is a rear perspective view of another embodiment of the forehead coupler of FIGS. 9A and 9B.
Figure 10B:
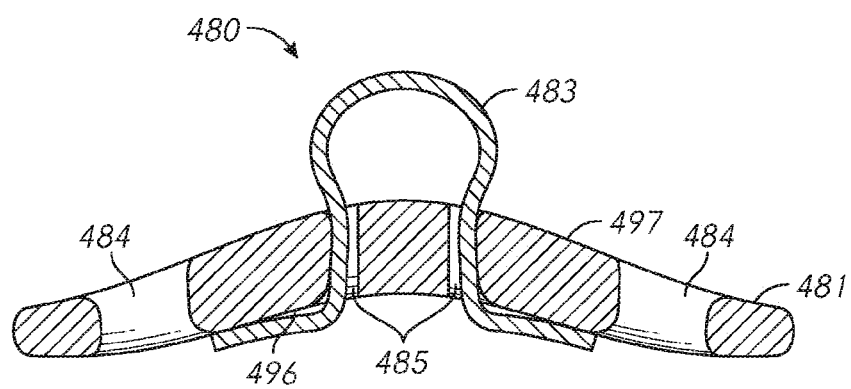
FIG. 10B is a top view of the forehead coupler of FIG. 10A.
Figure 10C:
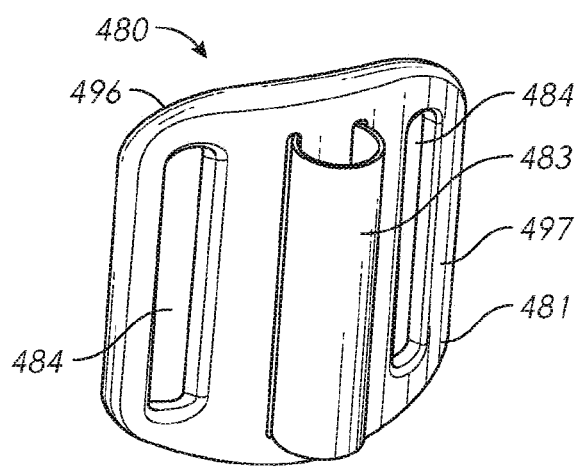
FIG. 10C is a front perspective view of the forehead coupler of FIG. 10A.

FIGS. 10A, 10B and 10C shows another variation of the embodiment of FIGS. 9A, 9B and 9C, wherein the front side 497 of the strap connector 481 is convex and the frame connector 483 is secured to the strap connector 481 by means such as welding or over-moulding. The strap connector 481 comprises first strap slots 484 and second strap slot 485, wherein the frame connector 483 is configured to pass through the second strap slot 485 before being secured to the strap connector 481.

Figure 11A:
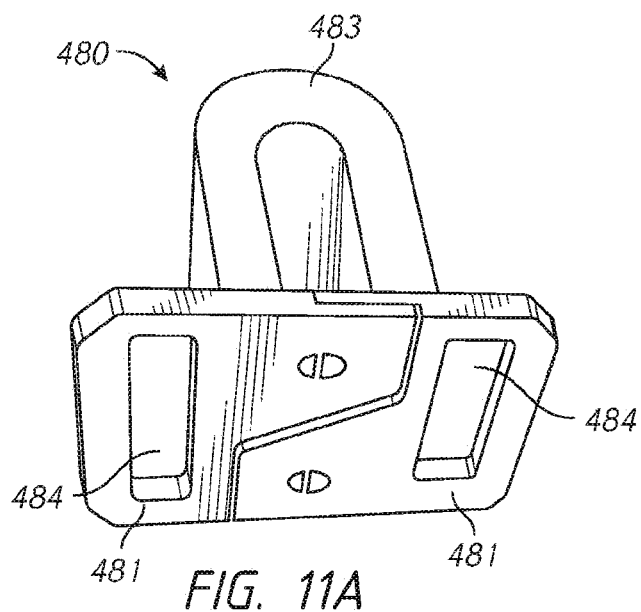
FIG. 11A is a top perspective of another embodiment of the forehead coupler of FIGS. 9A and 9B.
Figure 11B:
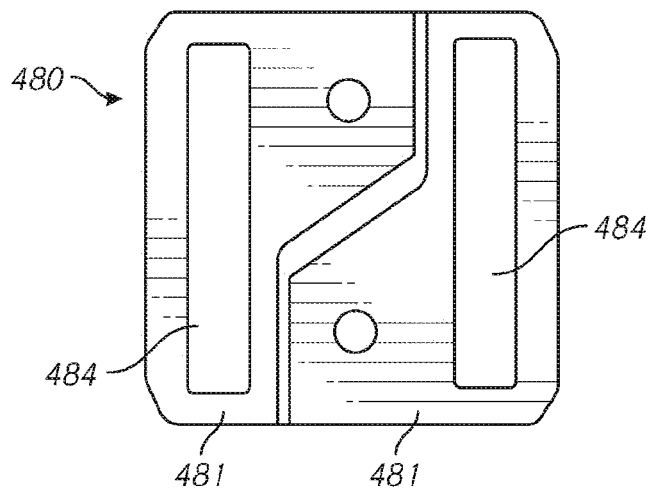
FIG. 11B is a rear view of the forehead coupler of FIG. 11A.
Figure 11C:
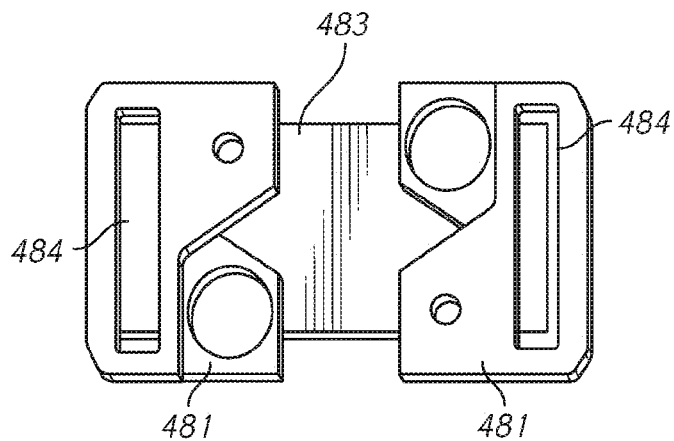
FIG. 11C is a rear view of the forehead coupler of FIGS. 11A and 11B in a disconnected configuration.

FIGS. 11A, 11B and 11C show a further variation of the forehead coupler 480 of FIGS. 9A, 9B and 9C. In this variation the strap connector 481 comprises two halves which are configured to be repeatedly connected and disconnected to each other. Each half of the strap connector 481 comprises an elongate strap slot 484 configured to receive one of the forehead straps 163. The two halves of the strap connector 481 are connected together by a button and hole type snap-fit fastener. It is to be understood that in other embodiments other types of snap-fit fasteners may be used and/or the connection between the two halves may be permanent. The frame connector 483 comprises a strap of fabric having two ends, wherein each of the ends is permanently secured to one half of the strap connector 481. The frame connector 483 forms a loop when the two halves of the strap connector are joined together, such that the loop may receive and/or retain a part of the forehead support 122 of the frame 120.

Figure 12A:
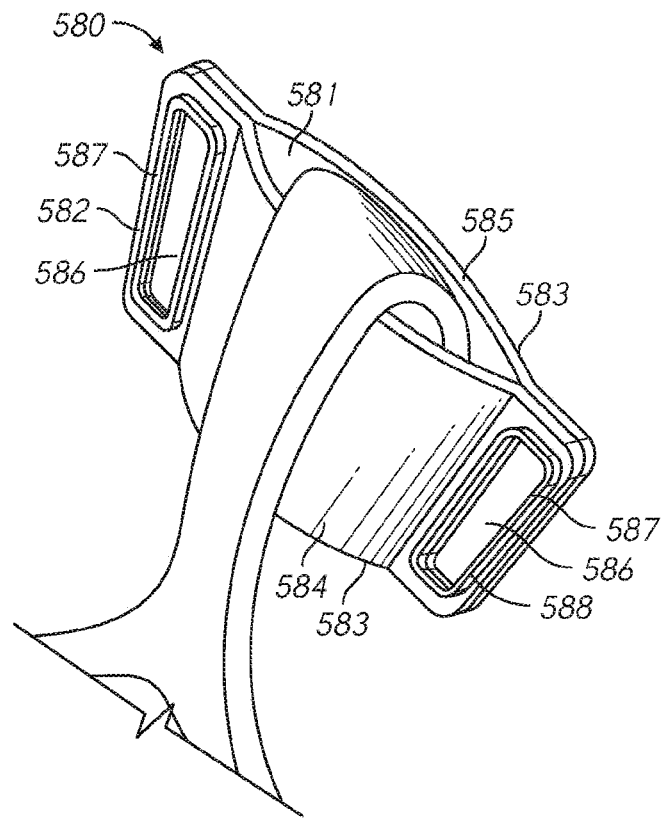
FIG. 12A is a top perspective view of a forehead coupler.
Figure 12B:
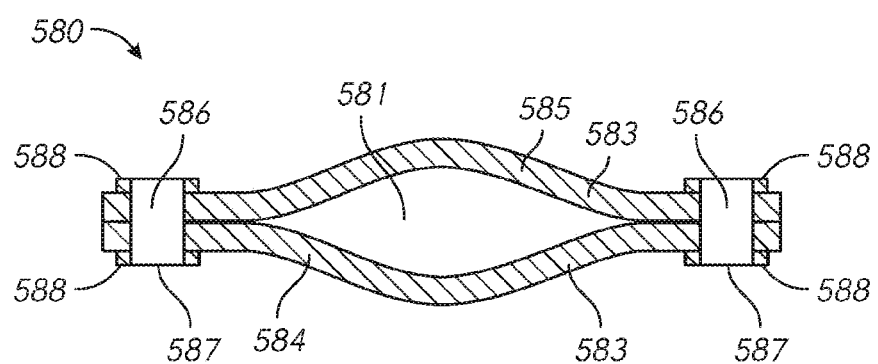
FIG. 12B is a top view of the forehead coupler of FIG. 12A.

The embodiments of FIGS. 7 through 11C have all been numbered corresponding to the forehead coupler 180 of FIGS. 2 to 6, such that like features have had a value of 100 added to their reference numeral. For example in FIG. 5A the strap connector has a reference numeral of 181 and in the embodiment of FIG. 7 the strap connector has a reference numeral of 281. Features with reference numerals that share the last two digits function in substantially the same way when assembled as a part of the respiratory mask system as a whole. FIGS. 12A and 12B have not been numbered strictly in this way. Only the forehead coupler as a complete component has been numbered with reference to the embodiment of FIGS. 2 to 6.

FIGS. 12A and 12B show yet another non-limiting exemplary embodiment of a forehead coupler 580. Forehead coupler 580 comprises a substantially flat and rectangular sleeve 581; having two short edges 582 and two long edges 583. The sleeve 581 is configured to receive and retain a part of the forehead support 122 of the frame 120. The sleeve 581 comprises a front layer 584, back layer 585 and two strap slots 586. The strap slots 586 run parallel to and are proximal to the short edges 582. The front and back layers 584 and 585 are joined together around the perimeter of the strap slots 586, such that the short edges 582 are joined together and the long edges 583 are open. The strap slots 586 extend through both the front and back layers 584 and 585 and are configured to receive the forehead straps 163. The short edges 582 are joined together by an over-moulded slot liner 587, wherein the slot liner 587 comprises a substantially rigid sheath that is configured to reinforce the structure of the strap slots 586. The slot liner 587 forms a lining around the perimeter of the strap slots 586 and extends through the front and back layers 584 and 585 terminating, on both sides, in a lip 588 that extends outwardly from the perimeter of each of the strap slots 586. The slot liner 587 is made of a substantially rigid thermoplastic material such that when it is over-moulded onto the sleeve 581 the material bonds to the material of the front and back layers 584 and 585.

The front and back layers 584 and 585 are made of a fabric having a flexibility that varies between planes. For example the fabric may be more flexible in a direction that is substantially perpendicular to the thickness of the fabric, than in a direction that is parallel to the thickness. This may be beneficial in allowing the forehead coupler 580 to conform to the facial geometry of a patient without bunching up in the connection between the frame 120 and the forehead coupler 580.

The forehead couplers of FIGS. 9A to 12B are secured to the forehead support 122 of the frame 120 with a different coupler connection 126 relative to the embodiment of FIGS. 2 to 8. The embodiments of FIGS. 9A to 12B are configured for use with a coupler connection that comprises a male component that connects to a female component formed by the frame connectors 483 and 583 of the forehead couplers 480 and 580. FIGS. 13A, to 15B show several non-limiting exemplary embodiments of coupler connections 600, 700 and 800 comprising a male component. The embodiments of FIGS. 13A, 13B, 14A and 14B both comprise a hook 610 or 710, wherein at least part of the hook 610, 710 is configured to pass though the frame connector 483 or the sleeve 581. In the embodiment of FIGS. 13A and 13B the hook 610 is substantially similar to a pocket clip that commonly forms part of a ballpoint pen, and comprises an elongate shank 611, a return arm 612 and a throat 613. The shank 611 is formed by the forehead support 122 and is configured to extend around a bend 614 where it transitions into the return arm 612. The shank 611 and the return arm 612 are spaced apart such that a throat 615 is formed between them. The throat 615 comprises a narrow throat opening 616 at the end opposing the bend 614. The return arm 612 comprises an elongate member that is configured to be received and retained by the frame connector 483 or the sleeve 581, such that a portion of the frame connector 483 or sleeve 581 sits within the throat 613. The throat opening 616 is configured to be narrower than the thickness of the fabric of the frame connector 483 or sleeve 581, such that the return arm 612 flexes to allow the frame connector 483 or sleeve 581 to pass through the throat opening 616. The narrowness of the throat opening 616 serves to retain the frame connector 483 or sleeve 581 in place once assembled. In use the return arm 612 is positioned proximal to the patient's forehead and the shank 611 is distal.

Figure 14B:
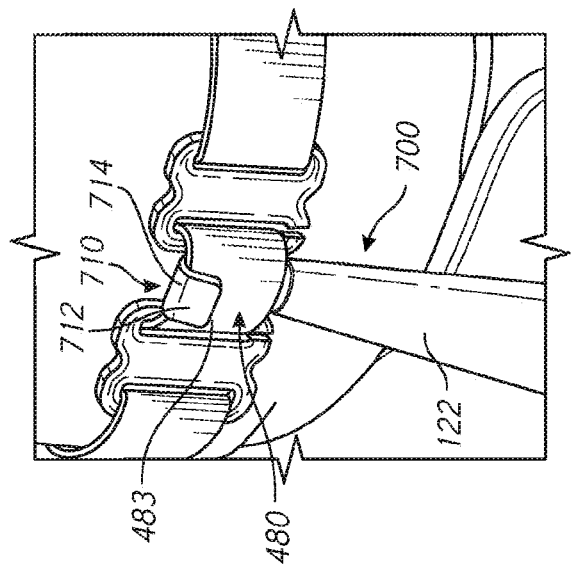
FIG. 14B is a perspective view of the coupler connection of FIG. 14A assembled to a forehead coupler.
Figure 14A:
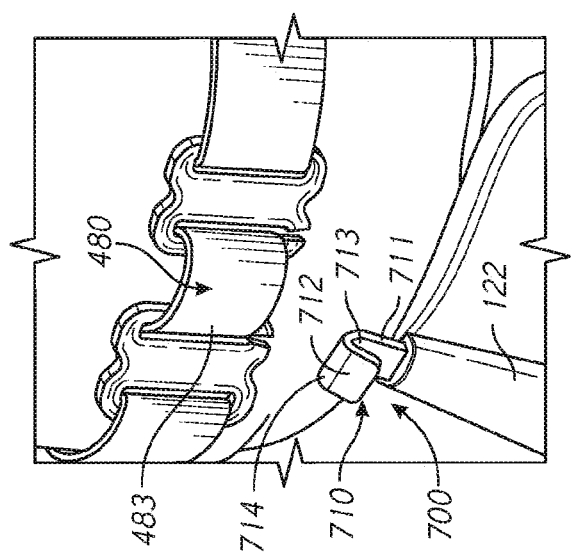
FIG. 14A is a perspective view of a coupler connection disconnected from a forehead coupler.

FIGS. 14A and 14B show another embodiment of the coupler connection 700 which comprises a hook 710 and is similar to the embodiment of FIGS. 13A and 13B. The hook 710 comprises a shank 711 and a return arm 712 being connected together by a bend 714. The shank 711 is formed by the forehead support 122 and is configured to be located proximal to the patient's forehead in use. The return arm 712 is a short extension of a bend 714, and is considerably shorter in this embodiment than in the embodiment of FIGS. 13A and 13B. The entire hook 710 is configured to pass through the forehead connector 483 (or in some embodiments the sleeve 581) such that the shank 711 is positioned within the frame connector 483 (or sleeve 581) and the bend 714 and return arm 712 extend over an edge of the fabric loop that forms the frame connector 483 (or front layer 584 of the sleeve 581). The bend 714 and return arm 712 act as a stop that inhibits or preferably prevents the forehead coupler 483 (or sleeve 581) from slipping off the end of the forehead support 122.

The coupler connection 800 of FIGS. 15A and 15B comprises a post 810 with an end stop 820. The post comprises an extension of the forehead support 122, which terminates in the end stop 820 and is configured to be inserted into the frame connector 483. There is a lip 830 formed where the dimensions of the forehead support stepdown and become smaller to form the post 810. The end stop 820 comprises a bulbous head or raised ridge around the end of the post 810. The lip 830 and end stop 820 are configured to be larger than the frame connector 483, such that the frame connector 483 is retained in place between them.

Figure 16B:
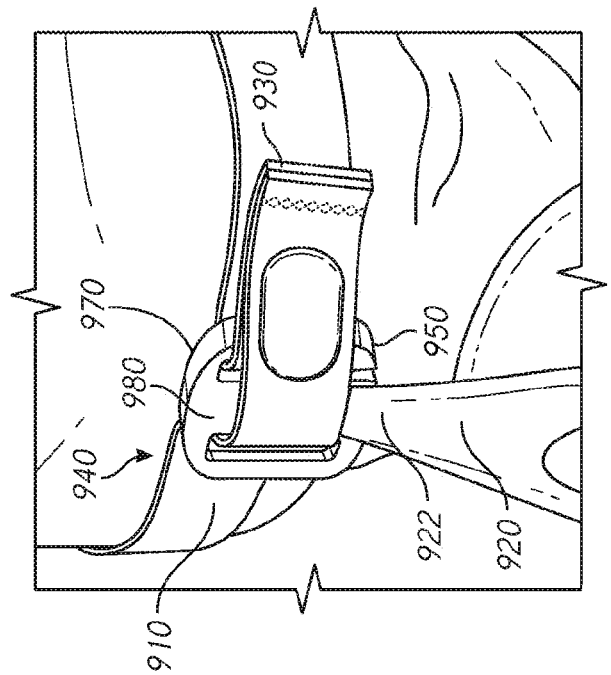
FIG. 16B is a perspective view of the headgear to frame connection of FIG. 16A in a secured configuration.
Figure 16A:
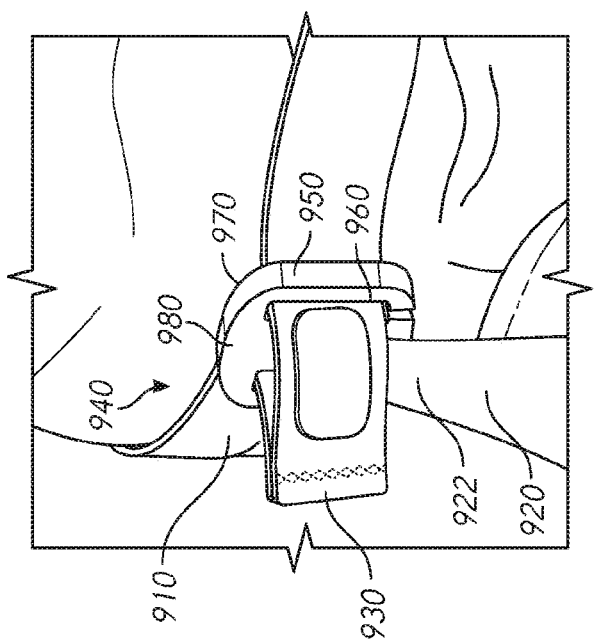
FIG. 16A is a perspective view of a headgear to frame connection in a non-secured configuration.

FIGS. 16A and 16B show a non-limiting exemplary embodiment of a headgear to frame connection for the respiratory mask system 100, wherein a headgear 900 comprises a forehead strap 910 which is removably attached to the frame 920. The forehead strap 910 is configured to extend from a rear portion (not shown) across a patient's forehead, and comprises a pair of straps that are permanently connected at a central joint 930 to form a closed loop. The length of the forehead strap 910 is such that the closed loop will be larger than the patient's forehead circumference. The central joint 930 may be formed by any means known in the industry, such as but not limited to sewing, welding or adhesives. In an alternative embodiment the forehead strap 910 may comprise a single strap that extends from one side of the rear portion to the other, forming a closed loop without a central joint 930.

The frame 920 can be substantially the same as that of the Simplus™ as made by Fisher & Paykel Healthcare Ltd. The frame 920 comprises a coupler connection 940 further comprising a substantially flat extension of a forehead support 922 having a pair of lateral hooks 950 that define a pair of elongate strap slots 960. The strap slots 960 are configured to receive the forehead strap 910, such that the forehead strap 910 passes from a rear side 970 of the coupler connection 940 through the strap slots 960, across a front side 980 of the coupler connection 940 and back through the other strap slot 960. The excess length of the forehead strap 910 can be pulled through the strap slots 960 so that the forehead support 922 is suspended just off a patient's forehead by the thickness of the forehead strap 910. The excess length of the forehead strap 910 is then folded to one side on the front side 980 of the coupler connection 940 and secured in place as shown in FIG. 16B. The excess length of the forehead strap 910 is secured in place by means such as but not limited to a hook and loop fastener.

FIGS. 17A through 17E show various views of a non-limiting exemplary embodiment of a forehead coupler 1000 that is configured to connect the forehead straps 163 of the headgear 160 together in a closed loop and connect the headgear 160 to a frame 1001. The forehead coupler 1000 comprises a substantially rigid buckle that has a butterfly-like shape, wherein the wings are formed by a pair of lateral strap connectors 1002 and the body is formed by a frame connector 1003 that is configured to link the strap connectors 1002 together. The frame connector 1003 is configured to connect to a coupler connection 1004 of a frame 1001 that is substantially similar to the coupler connection 600 of FIGS. 13A and 13B.

The strap connectors 1002 have a somewhat 'D' shaped profile and comprise a strap aperture 1005; configured to receive the forehead straps 163 of the headgear 160, and a strap guide 1006 configured to align the forehead straps 163. The strap apertures 1005 comprise an opening having a profile that is substantially 'D' shaped and offset from the profile of the strap connectors 1002; wherein the straight edge of the 'D' forms an inner edge 1007 of the strap guide 1006 and the curved side defines the boundary between the strap connectors 1002 and the frame connector 1003. The length of the inner edge 1007 is substantially the same as the width of the forehead straps 163, such that the forehead straps 163 can pass through the strap aperture 1005. In some configurations there can be a tight fit between the forehead straps 163 and the strap apertures 1005. In such a configuration the friction between the forehead straps 163 and the strap apertures 1005 causes the forehead straps to be temporarily retained at a set in-use length, when the free ends 166 are unsecured, until a force is applied by a user that overcomes the frictional forces. This means that the in-use length will not change until an intentional force is applied, which can be advantageous during fitting and adjustment of the respiratory mask and headgear.

Figure 17A:
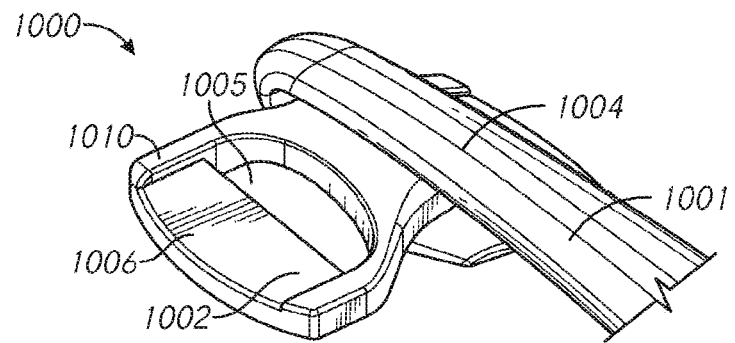
FIG. 17A is a perspective view of a forehead coupler assembled to a coupler connection.
Figure 17B:
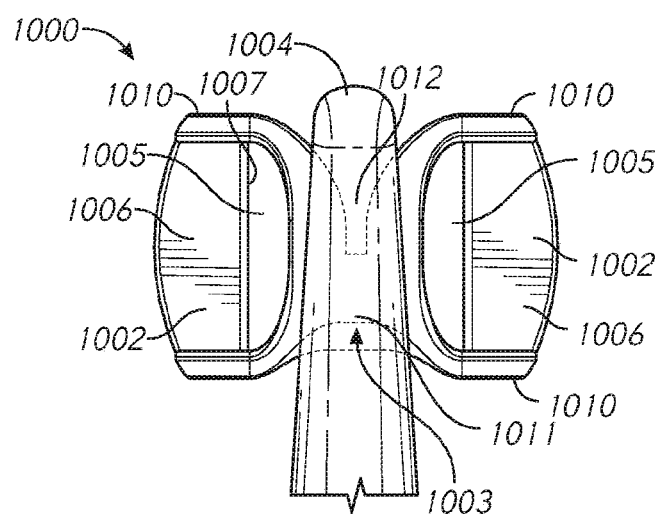
FIG. 17B is a front view of the forehead coupler and coupler connection of FIG. 17A.
Figure 17C:
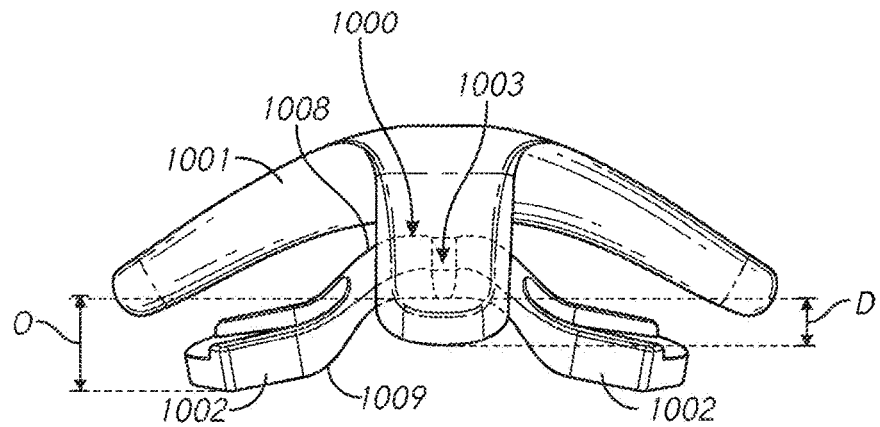
FIG. 17C is a top view of the forehead coupler and coupler connection of FIGS. 17A and 17B.

As shown in FIG. 17C the forehead coupler 1000 has a front side 1008 and a back side 1009, wherein the front side 1008 is configured to face away from the patient's face, in use, and the back side 1009 is configured to face towards the patient's face. The strap guide 1006 comprises a flat, substantially rectangular portion that extends laterally from the inner edge 1007 formed by the strap apertures 1005. On the front side 1008 the strap guide 1006 is recessed such that a lip 1010 is formed along each of the edges of the strap guide 1006 that are perpendicular to the inner edge 1007. The lips 1010 are spaced apart by the length of the inner edge 1007. The lips are configured to locate and align the forehead straps 163 within the boundary of the forehead coupler 1000. The strap connector 1002 is configured such that a forehead strap 163 passes along the back side 1009 of the strap guide 1006, through the strap aperture 1005 and back over the front side 1008 of the strap guide 1006, before being secured in place. The free end 166 of the forehead strap 163 is secured to the forehead strap by means described in relation to previous embodiments.

The frame connector 1003 comprises a crossbar 1011 and a rib slot 1012. With reference to the view shown in FIG. 17B, the crossbar 1011 comprises a solid beam that extends horizontally between the lower halves of the strap connectors 1002. It is configured to be received by the coupler connection 1004 of the frame 1001. The upper halves of the strap connectors 1002 are not connected and form the rib slot 1012. The rib slot 1012 comprises a gap between strap connectors 1002 having walls that are substantially perpendicular to the crossbar 1011 and curve outwardly in an upward direction from the crossbar 1011. The outward curvature of the walls of the rib slot 1012 provides a wide and smooth opening to guide the rib 1023 into the rib slot 1012, which allows the forehead coupler 1000 to be more easily aligned and connected to the coupler connection 1004 of the frame 1001. The rib slot 1012 is configured to engage with a corresponding rib that forms a part of the coupler connection 1004.

Figure 17D:
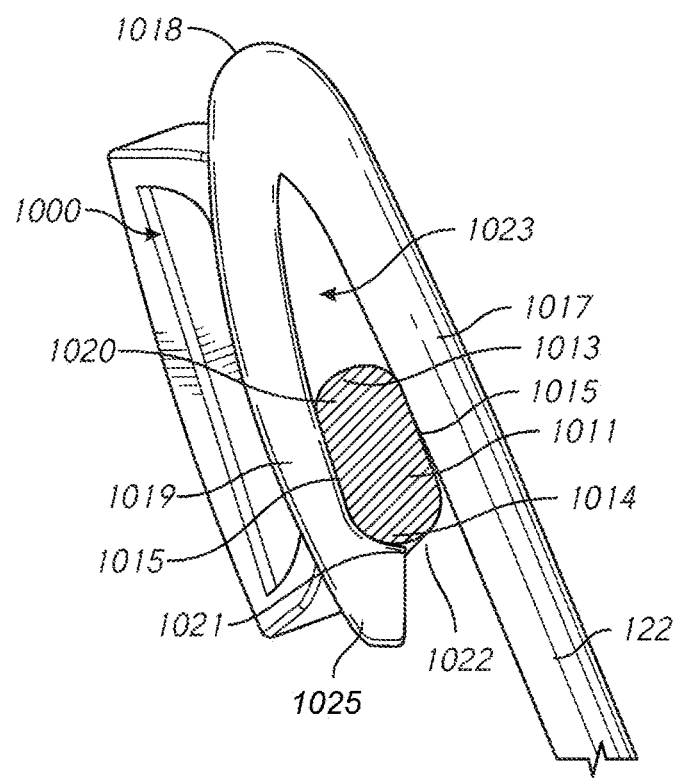
FIG. 17D is a cross-sectional side view of the forehead coupler and coupler connection of FIGS. 17A to 17C.

As shown in FIG. 17D, the crossbar 1011 has a cross-sectional profile comprising a first end 1013 and a second end 1014 being connected by two flat sides 1015, wherein the first and second ends 1013 and 1014 have semicircular profiles. The diameter of the first end 1013 is smaller than the diameter of the second end 1014 such that the crossbar 1011 is asymmetrical from end-to-end and thus an acute angle is formed between the two flat sides 1015. The smaller diameter of the first end 1013 and the angled flat sides 1015 provide a lead in that reduces the force required to engage the frame connector 1003 with the coupler connection 1004. The length of the flat sides 1015 is greater than the diameter of the second end 1014, which reduces rotation (i.e., about the first end and second end) and provides stability in the connection between the frame connector 1003 and the coupler connection 1004.

When viewed from above, as in FIG. 17C, it can be seen that the frame connector 1003 is offset from the strap connectors 1002, by a distance O. This reduces or minimizes the chances of the frame 1001 coming into contact with a patient's forehead during use, as the offset is greater than the depth of the coupler connection D.

Figure 17E:
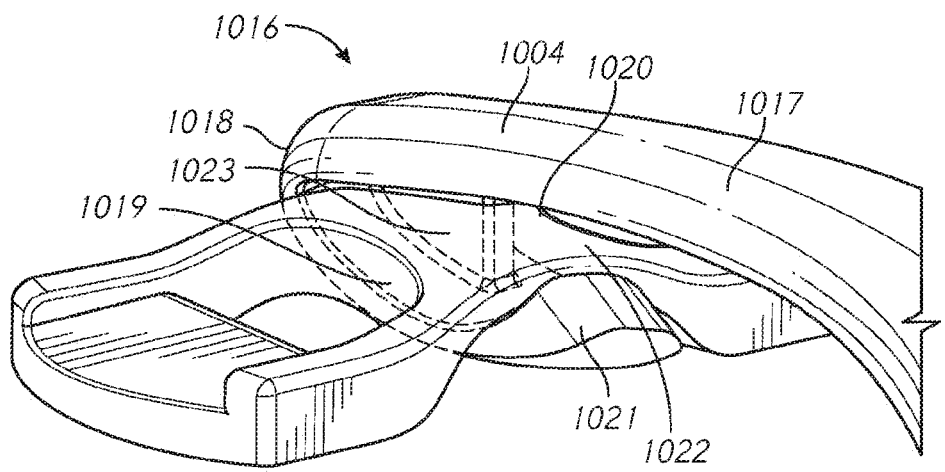
FIG. 17E is a perspective view of the coupler connection of FIGS. 17A to 17D.

The coupler connection 1004 is substantially similar to the coupler connection 600 of FIG. 13A. As shown in FIGS. 17D and 17E, it comprises a hook 1016 having a shank 1017 that extends approximately 180° around a bend 1018 and into a return arm 1019, wherein a throat 1020 is formed between the shank 1017 and the return arm 1019. The return arm 1019 comprises a bump 1021 at the end opposing the bend 1018, wherein the apex of the bump 1021 forms a throat opening 1022 that is narrower than the throat 1020. The apex of the bump 1021 is offset from the end of the return arm 1019 such that the bump 1021 has a lower surface 1025 that is angled towards the shank 1017 in an upwards direction. The lower surface 1025 forms a lead in which improves alignment of the crossbar 1011 with the throat opening 1022 and thus improves the ease with which the forehead coupler 1000 can be assembled to the coupler connection 1004. The outwardly curving walls of the rib slot 1012 also aid in aligning the frame connector 1003 with the throat opening 1022, during assembly of the forehead coupler 1000 and the frame 1001 by avoiding interference between the bend 1018 of the hook 1016 and the strap connectors 1002.

The throat 1020 is configured to receive the crossbar 1011 of the frame connector 1003. The return arm 1019 is configured to flex away from the shank 1017, about the bend 1018, such that the crossbar 1011 may pass through the throat opening 1022, which is narrower than the diameter of both the first and second ends 1013 and 1014 of the crossbar 1011. An interference fit between the crossbar 1011 of the forehead coupler 1000 and the frame 1001 (i.e., the crossbar 1011 and the return arm 1019) reduces slop or free-play in the joint to inhibit or prevent the frame 1001 from moving or rotating relative to the crossbar 1011. Further, the interference fit also provides an audible 'click' noise when the forehead coupler 1000 and the frame 1001 are connected together. The audible 'click' noise provides positive feedback for the user so that they know the forehead coupler 1000 and the frame 1001 are properly connected.

The hook 1016 further comprises a rib 1023, which is an elongate substantially rectangular extrusion that extends between the shank 1017 and the return arm 1019 such that the throat 1020 is filled in at the end that is proximal to the bend 1018. The rib is configured to inhibit or preferably prevent the forehead coupler 1000 from being connected to the coupler connection 1004 in the wrong orientation, and increases the strength of the hook 1016 and reduces the likelihood of the return arm 1019 being broken away from the shank 1017. The rib 1023 also improves the stability of the connection between the forehead coupler 1000 and the coupler connection 1004, by engaging with the rib slot 1012 of the frame connector 1003. In other words, the rib 1023 contacts the sidewalls of the rib slot 1012 which prevent or inhibit rotation of the frame connector 1003 around the rib 1023. The rib 1023 is configured to be substantially the same width as the portion of the rib slot 1012 that is perpendicular to the crossbar 1011 and have a substantially narrower width than the return arm 1019 and bump 1021. This at least substantially inhibits or preferably prevents the crossbar 1011 from being inserted into the throat 1020 in the wrong orientation.

FIGS. 18A through 18G show various views of another non-limiting embodiment of a forehead coupler 1100 that is substantially similar to the forehead coupler 1000. The forehead coupler 1100 is configured to connect the forehead straps 163 of the headgear 160 together in a closed loop and connect the headgear 160 to a frame 1101. The forehead coupler 1100 comprises a substantially rigid buckle that has a butterfly-like shape, wherein the wings are formed by a pair of lateral strap connectors 1102 and the body is formed by a frame connector 1103 that is configured to link the strap connectors 1102 together. The frame connector 1103 is configured to connect to a coupler connection 1104 of a frame 1101 that is substantially similar to the coupler connection 600 of FIGS. 13A and 13B.

Figure 18A:
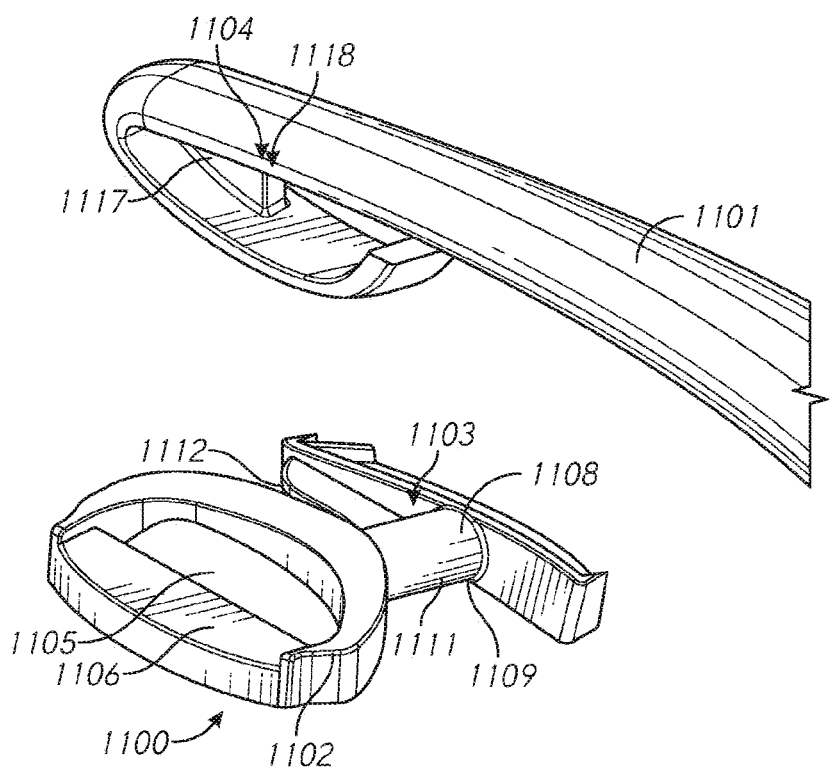
FIG. 18A is an exploded perspective view of a forehead coupler and coupler connection.
Figure 18B:
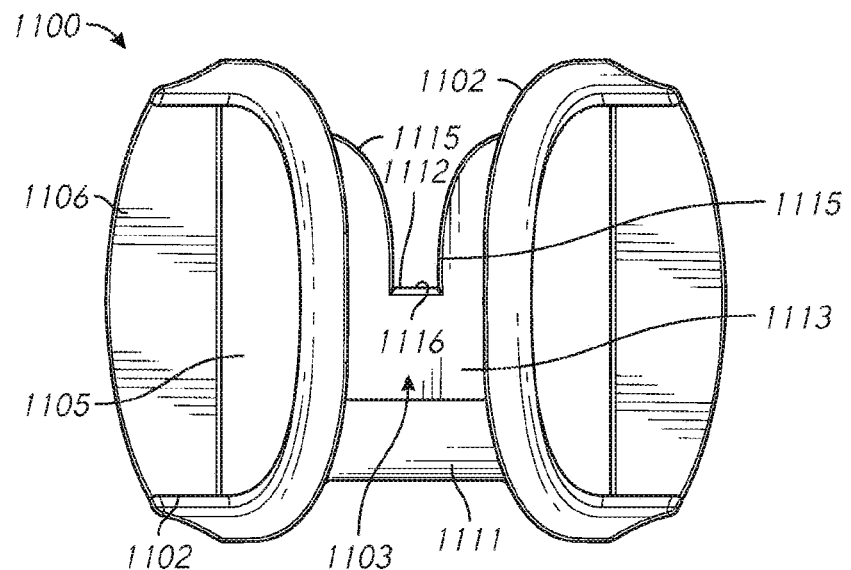
FIG. 18B is a front view of the forehead coupler of FIG. 18A.
Figure 18C:
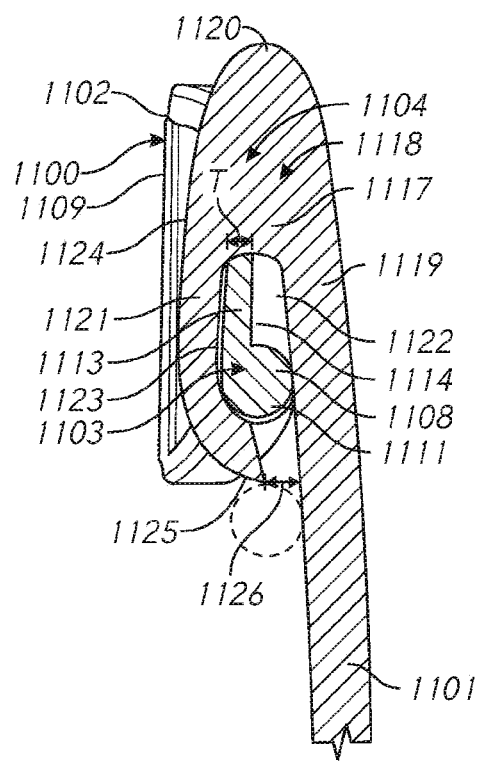
FIG. 18C is a cross-sectional side view of the forehead coupler and coupler connection of FIGS. 18A and 18B, assembled together.

As shown in FIGS. 18A and 18B, the strap connectors 1102 are substantially similar to the strap connectors 1002, and comprise a strap aperture 1105 and a strap guide 1106. The forehead coupler 1100 has a front side 1108 and a back side 1109, wherein the front side 1108 is configured to face away from the patient's face, in use, and the back side 1109 is configured to face towards the patient's face. The frame connector 1103 is similar to frame connector 1003 in that it comprises a crossbar 1111 and a rib slot 1112. In this embodiment, the crossbar 1111 comprises a cylindrical beam that extends between the lower halves of the two strap connectors 1102. The rib slot 1112 is formed within a thin flange 1113 that extends upwardly (as viewed in FIG. 18B) from the crossbar 1111 and extends between the two strap connectors 1102. As shown in FIG. 18c, the flange 1113 extends tangentially from the back side 1109 of the crossbar 1111 and has a thickness T that is less than the radius of the crossbar 1111, thus creating a recess 1114 on the front side 1108 of the frame connector 1103. The rib slot 1112 comprises a cut out in the flange 1113 that is substantially the same shape as rib slot 1012. As based on the view of FIG. 18B, the rib slot 1112 comprises two substantially vertical long edges 1115 separated by a horizontal short edge 1116. The short edge 1116 runs parallel with the crossbar 1111. The two long edges 1115 extend perpendicularly from the ends of the short edge 1116 and curve outwardly in an upwards direction. The outward curvature of the two long edges 1115 provides a wide and smooth opening to guide the rib 1117 into the rib slot 1112, which allows the forehead coupler 1100 to be more easily aligned and connected to the coupler connection 1104 of the frame 1101. The rib slot 1112 is configured to engage with a corresponding rib 1117 that forms a part of the coupler connection 1104. The rib 1117 and rib slot 1112 improve the stability of the connection between the forehead coupler 1100 and the coupler connection 1104. In other words, the rib 1117 contacts the two long edges 1115 of the rib slot 1112. The contact prevents or inhibits rotation of the frame connector 1103 around the rib 1117.

The coupler connection 1104 is substantially similar to the coupler connection 1004 of FIGS. 17A to 17E. It comprises a hook 1118 having a shank 1119 that extends approximately 360° around a bend 1120 and into a return arm 1121, wherein a throat 1122 is formed between the shank 1119 and the return arm 1121. The return arm 1121 comprises an internal surface 1123 and an external surface 1124, wherein the external surface 1124 is convexly curved. The external surface 1124 terminates and meets the internal surface 1123 at point which forms a free end 1125 at the end opposing the bend 1120. A throat opening 1126 is formed between the free end 1125 and the shank 1119, wherein the throat opening 1126 is narrower than the throat 1122. The throat opening 1126 is configured to be narrower than the radius of the crossbar 1111 in order to inhibit or preferably prevent incorrect assembly of the forehead coupler 1100 to the coupler connection 1104, as shown in FIGS. 18D to 18G. The hook 1118 further comprises a rib 1117, which is substantially the same as the rib 1023 of the previous embodiment shown in FIG. 17E.

Figure 18D:
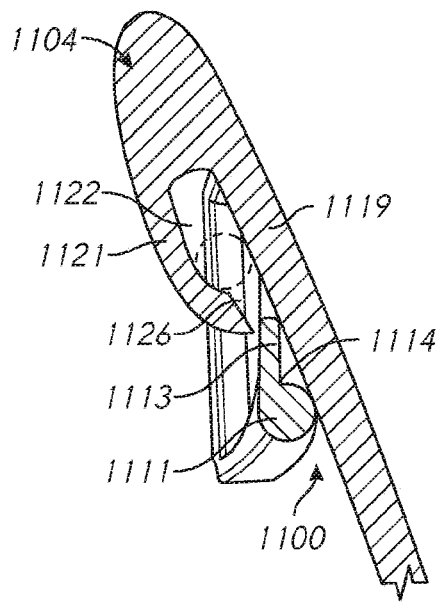
FIG. 18D is cross-sectional side view of the forehead coupler and coupler connection of FIGS. 18A to 18C, wherein the forehead coupler is in the only orientation that allows for a complete and correct assembly between the forehead coupler and the coupler connection.
Figure 18E:
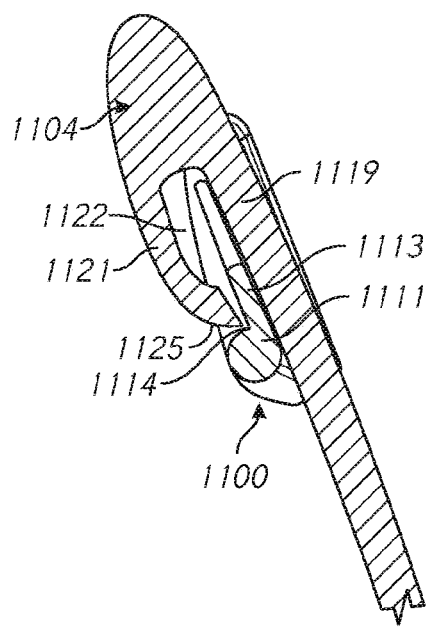
FIG. 18E is cross-sectional side view of the forehead coupler and coupler connection of FIGS. 18A to 18C, wherein the forehead coupler is in an orientation that does not allow assembly between the forehead coupler and the coupler connection.

FIG. 18D shows the only orientation that allows for a complete and correct assembly between the forehead coupler 1100 and the coupler connection 1104. The forehead coupler must be oriented with the flange 1113 above the crossbar 1111 and the recess 1114 proximal to the shank 1119. It can be seen that the flange 1113 enters the throat opening 1126 first and forms a wedge that forces the return arm 1121 to flex away from the shank 1119 such that the crossbar 1111 can pass through the throat opening 1126. FIG. 18E shows that forehead coupler 1100 preferably cannot be assembled with the coupler connection 1104 when oriented with the flange 1113 above the crossbar 1111 and the recess 1114 proximal to the return arm 1121. This is because the point of the free end 1125 engages with the recess 1114 such that the crossbar 1111 acts as a stop. The thickness of the flange 1113 being less than the radius of the crossbar 1111 means that the engagement of the free end 1125 with crossbar 1111 at the base of the recess 1114 does not result in the return arm 1121 flexing away from the shank 1119, and thus the crossbar 1111 preferably cannot pass through the throat opening 1126.

Figure 18F:
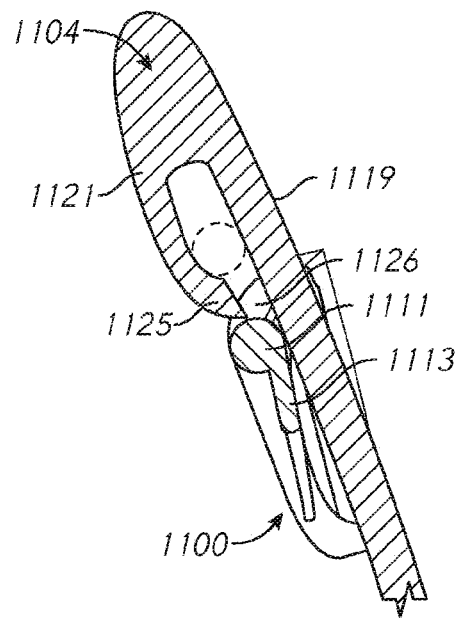
FIG. 18F is cross-sectional side view of the forehead coupler and coupler connection of FIGS. 18A to 18C, wherein the forehead coupler is in an orientation that does not allow assembly between the forehead coupler and the coupler connection.
Figure 18G:
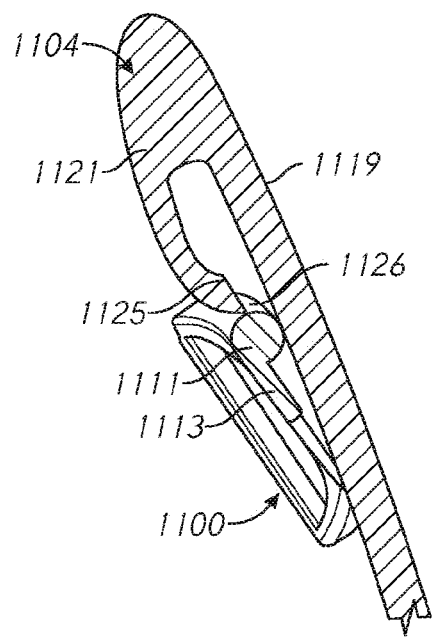
FIG. 18G is cross-sectional side view of the forehead coupler and coupler connection of FIGS. 18A to 18C, wherein the forehead coupler is in an orientation that does not allow assembly between the forehead coupler and the coupler connection.

FIGS. 18F and 18G show the forehead coupler 1100 in two more orientations that will not allow it to be assembled with the coupler connection 1104. The forehead coupler is oriented with the crossbar 1111 above the flange 1113 in both configurations. Since the throat opening 1126 is narrower than the radius of the crossbar 1111 the point of the free end 1125 engage with the crossbar 1111 in such a way that the crossbar 1111 cannot generate any leverage to flex the return arm 1121 away from the shank 1119. As the return arm 1121 is not flexed away from the shank 1119 the throat opening 1126 is not enlarged such that the crossbar 1111 cannot pass through. For forehead couplers 1000, 1100 that are substantially rigid, it is advantageous that they can only be assembled to the coupler connection 1004, 1104 in one orientation. This is because it reduces the likelihood of a user assembling the mask incorrectly, which may reduce the efficacy of therapy provided to the patient.

FIGS. 19A to 19E show a range of views of a further non-limiting exemplary embodiment of a forehead coupler 1200, which is similar in configuration to forehead couplers 1000 and 1100. The forehead coupler 1200 is configured to connect to a coupler connection 600, substantially as described in relation to FIGS. 13A and 13B. Forehead coupler 1200 comprises a pair of strap connectors 1201 that are connected together by a frame connector 1202. The strap connector comprises a strap aperture 1203 through which the forehead straps 163 of headgear 160 are configured to pass.

The frame connector 1202 is formed by a solid portion between the two strap apertures 1203. As shown in FIG. 19C, the frame connector 1202 is offset from the forehead strap connectors 1201, such that when assembled to the coupler connection 600 the strap connectors are substantially flush with the return arm 612. This configuration will preferably prevent the return arm 612 from contacting the patient's forehead during use, as the forehead straps 163 will form a cushioning layer between the strap connectors 1201 and the patient's forehead. As shown in FIG. 19D the frame connector has an elongate cross-sectional profile comprising a circular lower end 1204 and a wedge shaped upper end 1205. The wedge shaped upper end 1205 is configured to act as a lead in that passes through the throat opening 616 and flex the return arm 612 away from the shank 611 such that the throat opening 616 is enlarged and the lower end 1204 can pass through. The circular cross-section of the lower end 1204 has a diameter that is greater than the width of the throat opening 616. This configuration provides a snap fit connection that retains the frame connector 1202 within the coupler connection 600.

Figure 19A:
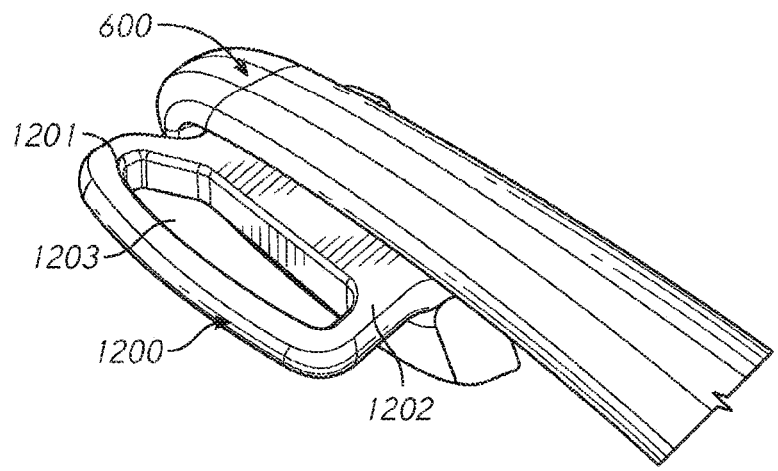
FIG. 19A is a perspective view of a forehead coupler assembled to the coupler connection of FIGS. 13A and 13B.
Figure 19B:
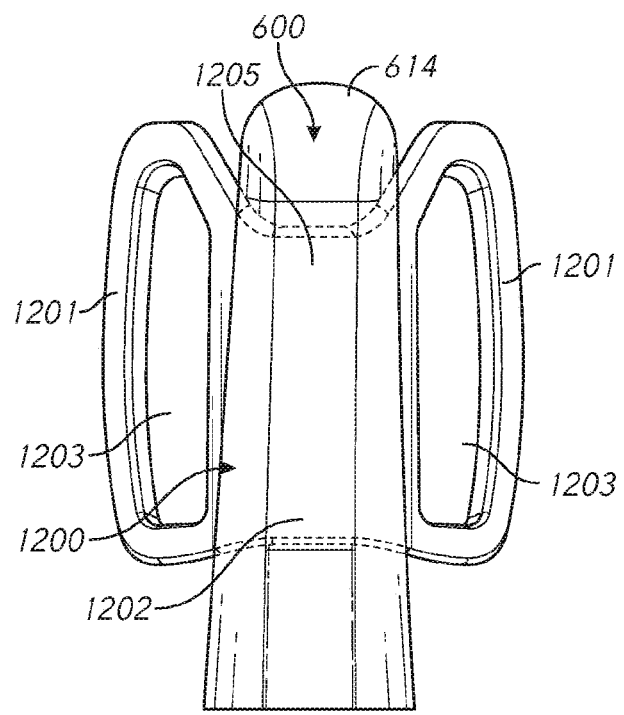
FIG. 19B is a front view of the forehead coupler and coupler connection of FIG. 19A.
Figure 19C:
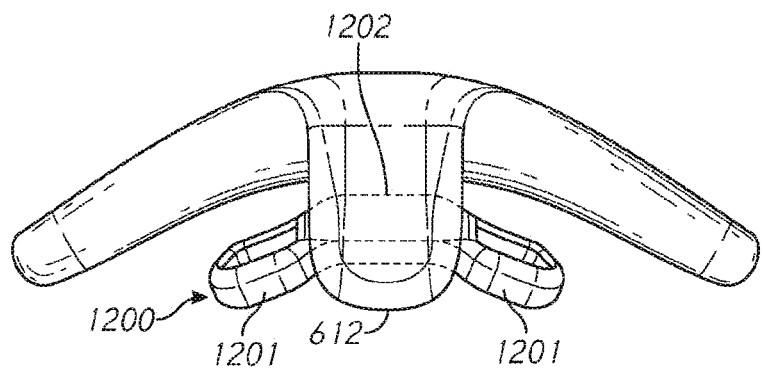
FIG. 19C is a top view of the forehead coupler and coupler connection of FIGS. 19A and 19B.
Figure 19D:
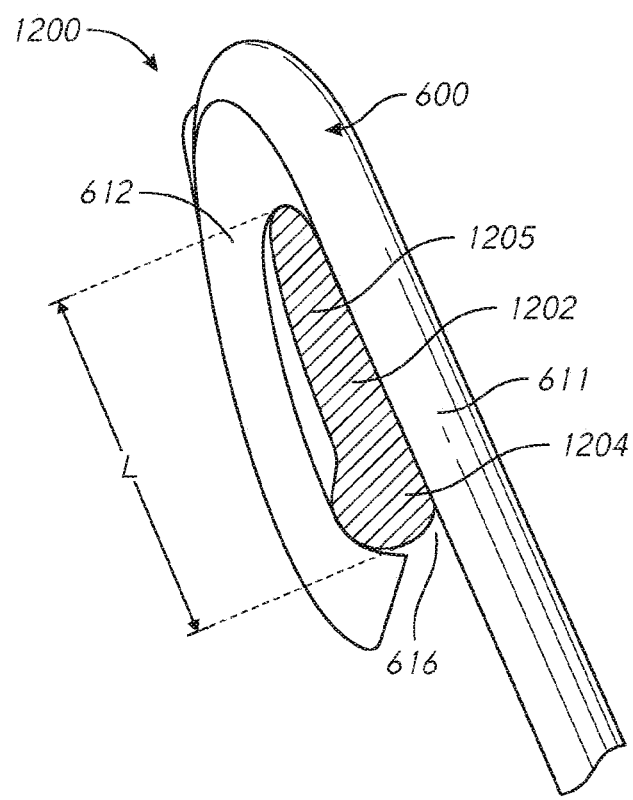
FIG. 19D is a cross-sectional side view of the forehead coupler and coupler connection of FIGS. 19A to 19C.

As shown in FIG. 19B, the strap connectors 1201 extend beyond the upper end 1205 of the frame connector 1202, which results in the bend 614 of the coupler connection 600 being substantially flush with the upper ends of the strap connectors, in use. This may improve the aesthetics of the mask. The length L (as shown in FIG. 19D) of the frame connector 1202 improves the rotational stability of the connection between the coupler connection 600 and the forehead coupler 1200.

Figure 20H:
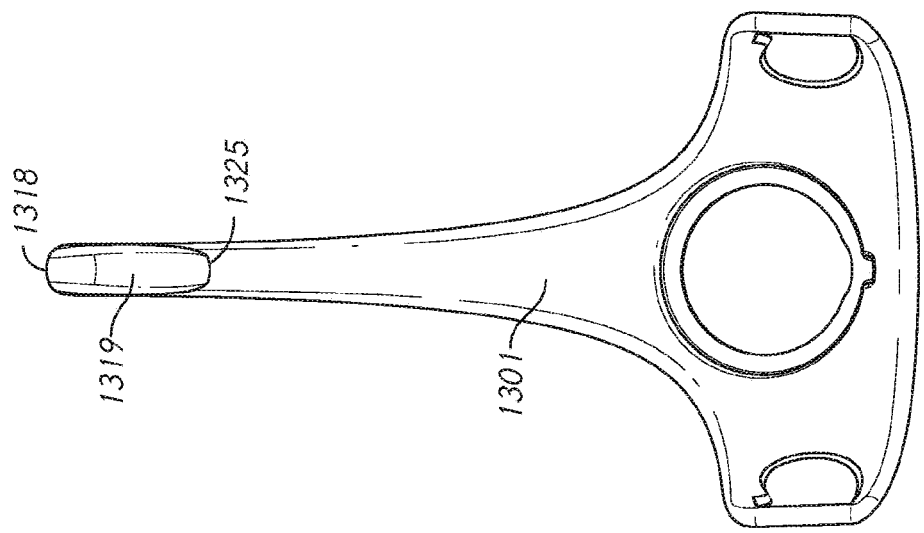
FIG. 20H is a rear view of the frame that connects with the forehead coupler of FIG. 20A.
Figure 20G:
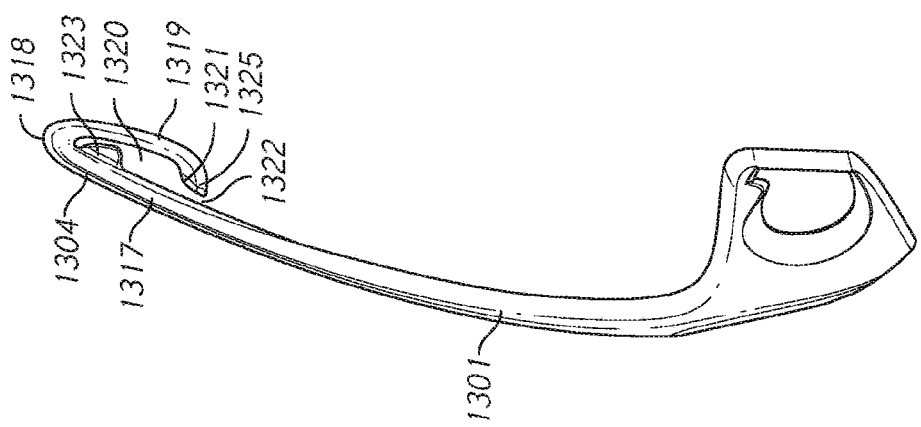
FIG. 20G is a side view of a frame that connects with the forehead coupler of FIG. 20A.

FIGS. 20A to 20I illustrate a range of views of an alternative frame connector and coupler connection arrangement for connecting a forehead coupler 1300 to a frame 1301. The forehead coupler 1300 is configured to connect the forehead straps 163 of the headgear 160 together in a closed loop and connect the headgear 160 to the frame 1301. As shown in FIGS. 20A and 20B, the forehead coupler 1300 comprises a substantially rigid buckle that has a butterfly-like shape, wherein the wings are formed by a pair of lateral strap connectors 1302 and the body is formed by a frame connector 1303 that is configured to link the strap connectors 1302 together. The frame connector 1303 is configured to connect to a coupler connection 1304 of the frame 1301 that is substantially similar to the coupler connection 600 of FIGS. 13A and 13B.

As shown in FIGS. 20A and 20B, the strap connectors 1302 are substantially similar to the strap connectors 1002, 1102 and comprise a strap aperture 1305 and a strap guide 1306. The forehead coupler 1300 has a front side 1308 and a back side 1309, wherein the front side 1308 is configured to face away from the patient's face, in use, and the back side 1309 is configured to face towards the patient's face. The frame connector 1303 is similar to frame connectors 1003, 1103 in that the frame connector 1303 comprises a crossbar 1311 similar to the crossbar 1011 and a rib slot 1312 similar to the rib slot 1112.

Similar to the crossbar 1011, the crossbar 1311 has a cross-sectional profile comprising a first end 1333 and a second end 1334 being connected by two flat sides 1335, wherein the first and second ends 1333, 1334 have semicircular profiles. The diameter of the first end 1333 is smaller than the diameter of the second end 1334 and thus an acute angle is formed between the two flat sides 1335. The smaller diameter of the first end 1333 and the angled flat sides 1335 reduces the force required to engage the frame connector 1303 with the coupler connection 1304. The length of the flat sides 1335 is greater than the diameter of the second end 1334, which reduces rotation (i.e., about the first end and second end) and provides stability in the connection between the frame connector 1303 and the coupler connection 1304. Similar to the frame connector 1003 in FIG. 17C, the frame connector 1303 is offset from the strap connectors 1302, as shown in FIG. 20F. This reduces or minimizes the chances of the frame 1301 coming into contact with a patient's forehead during use.

Similar to the rib slot 1112, the rib slot 1312 is formed within a thin flange 1313 that extends upwardly (as viewed in FIG. 20C) from the crossbar 1311 and extends between the two strap connectors 1302. As shown in FIG. 20E, the flange 1313 extends tangentially from the back side 1309 of the crossbar 1311 and has a thickness T that is less than the radius of the crossbar 1311, thus creating a recess 1314 on the front side 1308 of the frame connector 1303. The recess 1314 is similar to recess 1114 in FIGS. 18A to 18G. More specifically, the free end 1325 of the return arm 1319 engages the recess 1314 to prevent connection of the forehead coupler 1100 and the coupler connection 1104 in only one orientation. That is, similar to FIG. 18D, when the forehead coupler 1300 is inserted into the coupler connection 1304 with the recess 1314 facing away from the free end 1325 of the return arm 1319, the flange 1313 enters the throat opening 1322 first and forms a wedge that forces the return arm 1319 to flex away from the shank 1317 such that the crossbar 1311 can pass through the throat opening 1322. However, similar to FIG. 18E, when the forehead coupler 1300 is inserted into the coupler connection 1304 with the recess 1314 facing the free end 1325 of the return arm 1319, the free end 1325 engages with the recess 1314 such that the crossbar 1311 acts as a stop. The thickness of the flange 1313 being less than the radius of the crossbar 1311 means that the engagement of the free end 1325 with crossbar 1311 at the base of the recess 1314 does not result in the return arm 1319 flexing away from the shank 1317, and thus the crossbar 1311 preferably cannot pass through the throat opening 1322.

The rib slot 1312 comprises a cut out in the flange 1313 that is substantially the same shape as rib slot 1012, 1112. As based on the view of FIGS. 20B to 20D, the rib slot 1312 comprises two substantially vertical long edges 1315 separated by a horizontal short edge 1316. The short edge 1316 runs parallel with the crossbar 1311. The two long edges 1315 extend perpendicularly from the ends of the short edge 1316 and curve outwardly in an upwards direction. The outward curvature of the two long edges 1315 provides a wide and smooth opening to guide the rib 1323 into the rib slot 1312, which allows the forehead coupler 1300 to be more easily aligned and connected to the coupler connection 1304 of the frame 1301. The rib slot 1312 is configured to engage with a corresponding rib 1323 that forms a part of the coupler connection 1304.

As shown in FIGS. 20G to 20K, the coupler connection 1304 of the frame 1301 is similar in configuration to the coupler connections 1004 and 1104. That is, similar to the coupler connections 1004 and 1104, the coupler connection 1304 comprises a hook having a shank 1317 that extends approximately 180° around a bend 1318 and into a return arm 1319, wherein a throat 1320 is formed between the shank 1317 and the return arm 1319. Further, the hook comprises a rib 1323, which is an elongate substantially rectangular extrusion that extends away from the shank 1317 towards the return arm 1319. Similar to the coupler connections 1004 and 1104, in operation, the throat 1320 is configured to receive the crossbar 1311 of the frame connector 1303. The return arm 1319 is configured to flex away from the shank 1317, about the bend 1318, such that the crossbar 1011 may pass through the throat opening 1322, which is narrower than the diameter of both the first and second ends 1313 and 1314 of the crossbar 1311. When the crossbar 1311 is positioned within the throat 1320, the rib 1323 is positioned within the rib slot 1312, which improves the stability of the connection between the forehead coupler 1300 and the coupler connection 1304. In other words, the rib 1323 is seated in the rib slot 1312 such that the rib 1323 contacts the two long edges 1315 of the rib slot 1312 and prevents or inhibits rotation of the frame connector 1303 within the throat 1320. That is, the contact between the sides of the rib 1323 and the two long edges 1315 of the rib slot 1312 obstructs rotation of the frame connector 1303 relative to the frame 1301. The rib 1323 is configured to be substantially the same width as the portion of the rib slot 1312 that is perpendicular to the crossbar 1311 and have a substantially narrower width than the return arm 1319 and the bump 1321. This at least substantially inhibits or preferably prevents the crossbar 1311 from being inserted into the throat 1320 in the wrong orientation. Further, an interference fit between the crossbar 1311 of the forehead coupler 1300 and the frame 1301 (i.e., the shank 1317 and the return arm 1319) reduces slop or free-play in the joint to prevent the frame 1301 from moving or rotating relative to the crossbar 1311. Further, the interference fit also provides an audible 'click' noise when the forehead coupler 1300 and the frame 1301 are connected together. The audible 'click' noise provides positive feedback for the user so that they know the forehead coupler 1300 and the frame 1301 are properly connected.

Figure 20K:
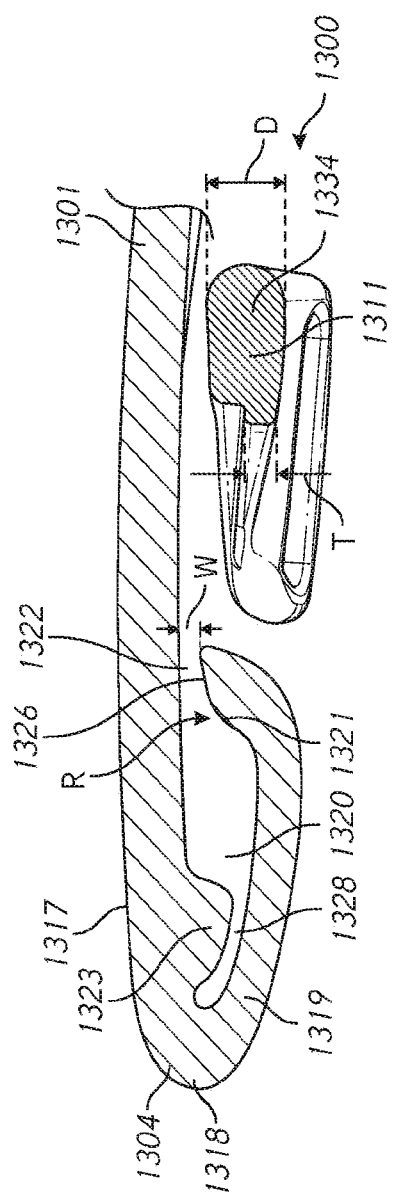
FIG. 20K is a cross-sectional side view of the frame and the forehead coupler of FIGS. 20A to 20H.

In contrast to the coupler connections 1004, 1104, the rib 1323 of the coupler connection 1304 is separated from the return arm 1319 by a gap 1328 (as shown in FIG. 20I) whereas the ribs 1023, 1117 extend all the way through the throat 1020, 1122 from the shank 1017, 1119 to the return arm 1019, 1121. Separating the rib 1323 from the return arm 1319 allows the entire length of the return arm 1319 to flex at the bend 1318. As such, the force required to widen the throat opening 1322 decreases, compared to the return arms 1019, 1121 having attached ribs 1023, 1117. As a result, the force required to insert the frame connector 1303 into the frame 1301 decreases (i.e., the effort required to connect and disconnect the forehead coupler 1300 to the frame 1301 decreases), which makes donning and removing the headgear easier. The bend 1318 may have a shape and/or thickness that reduces the stresses within the bend 1318 such that the return arm 1319 will not fracture or inelastically (plastically) deform. Further, the gap 1328 (i.e., the distance between the rib 1323 and the return arm 1319) may have a width that is substantially similar to the width of the throat opening 1322. Similarly, the gap 1328 and the throat opening 1322 is configured to be narrower than the thickness of the fabric of the forehead straps 163 of the headgear 160 such that the forehead straps 163 may not be mistakenly positioned within the gap 1328. That is, the gap 1328 is too narrow for the forehead straps 163 to be inserted within the gap 1328. As a result, by preventing the forehead straps 163 from being inserted within the gap 1328, the user may not mistakenly assume that the forehead straps 163 are properly attached to the frame 1301 (i.e., the forehead straps 163 being attached directly to the frame 1301 without using the frame connector 1303). In some configurations, the throat opening 1322 has a width W of 1.45 mm, as illustrated in FIG. 20K.

Similar to the return arms 1019, 1121, the return arm 1319 comprises a bump 1321 at the end opposing the bend 1318, wherein the apex of the bump 1321 forms a throat opening 1322 that is narrower than the throat 1320. The apex of the bump 1321 is offset from the end of the return arm 1319 such that the bump 1321 has a surface 1326 that is angled towards the shank 1317 such that the throat opening 1322 narrows in a direction toward the end of the return arm 1319. As illustrated in FIG. 20K, the bump 1321 may be rounded by a fillet having a radius R. Rounding the bump 1321 removes sharp edges that may prevent the throat opening 1322 from widening to allow the crossbar 1311 from passing through the throat opening 1322. Accordingly, the force required to remove the forehead coupler 1300 from the frame 1301 decreases which improves usability of the headgear. In some configurations, the bump 1321 may have a radius R of 2 mm Even further, in some configurations, the semicircular second end 1334 of the crossbar 1311 may have a diameter D of 5.35 mm. The second end 1334 of the crossbar 1311 with a diameter D may contact the bump 1321 with a radius R to provide smooth and gradual widening of the throat 1320 as the crossbar 1311 initially passes through the throat opening 1322.

Similar to the crossbar 1111 in FIGS. 18F and 18G, the diameter D of the semicircular second end 1334 of the crossbar 1311 may be greater than twice the width W of the throat opening 1322 such that the crossbar 1311 may not be inserted into the throat opening 1322 in any orientation leading with the second end 1334 (i.e., the second end 1334 inserted into the throat opening 1322 prior to the first end 1333). The throat opening 1322 is narrower than the radius of the crossbar 1311 and a free end 1325 of the return arm 1319 engages the second end 1334 of the crossbar 1311 in such a way that the crossbar 1311 cannot generate any leverage to flex the return arm 1319 away from the shank 1317. As the return arm 1319 is not flexed away from the shank 1317, the throat opening 1322 is not enlarged such that the crossbar 1311 cannot pass through and be inserted into the throat 1320.

As a result of the asymmetric shape and configuration of the forehead coupler 1300, the forehead coupler 1300 may be connected to the coupler connection 1304 of the frame 1301 in only one of four possible orientations. That is, the recess 1314 and the crossbar 1311 allow the forehead coupler 1300 to be inserted into the throat 1320 in only the orientation in which the flange 1313 is leading and the recess 1314 faces away from the free end 1325 of the return arm 1319. In other words, the forehead coupler 1300 cannot be inserted into the throat 1320 in an orientation in which the flange 1313 is leading and the recess 1314 faces the free end 1325 of the return arm 1319, an orientation in which the second end 1334 is leading and the recess 1314 faces away from the free end 1325, and an orientation in which the second end 1334 is leading and the recess 1314 faces the free end 1325. As such, the user is inhibited or prevented from inserting the forehead coupler 1300 into the coupler connection 1304 inside out, backwards, or backwards and inside out.

In some arrangements, a universal frame may be used with sealing cushions of different sizes. That is, the same frame may be fitted to smaller-sized sealing cushions and medium- to larger-sized sealing cushions. Accordingly, the frame must accommodate various sized sealing cushions which are centred on the gas inlet of the frame. Even further, the frame must provide a range of size adjustability to accommodate each sealing cushion size to ensure proper fitment (i.e., comfort and sealability) for users of different sizes. One particular type of size adjustment is the positioning of the forehead straps relative to the sealing cushion and the frame. For smaller users utilizing a smaller-sized sealing cushion, proper fitment may require the forehead straps to be positioned closer to the sealing cushion compared to a larger user utilizing a medium- to larger-sized sealing cushion. In other words, having the forehead straps in the same position on a universal frame for all sealing cushion sizes may be result in poor fitment for some users. Therefore, it may be necessary for the forehead straps to connect to the frame at a lower location for sealing cushions of smaller sizes (i.e., relative to medium/larger sizes), in order to ensure that the connection between the forehead straps and the frame is not positioned too high on the user's forehead.

Figure 21C:
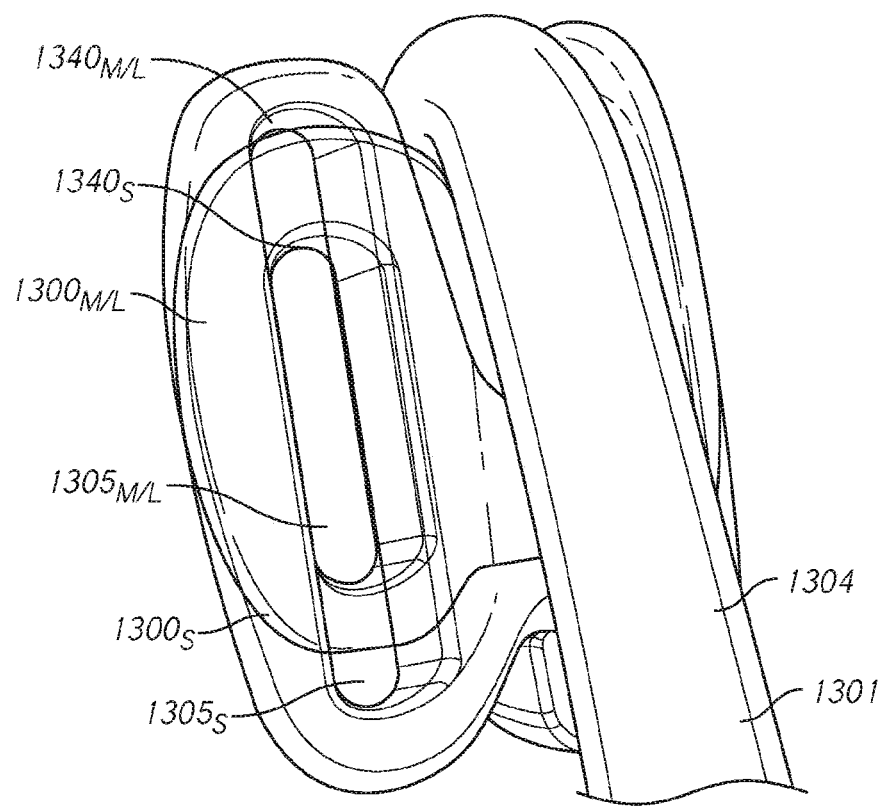
FIG. 21C is a front perspective view of the size small forehead coupler overlaid over the size medium/large forehead coupler when connected to the universal frame.
Figure 22A:
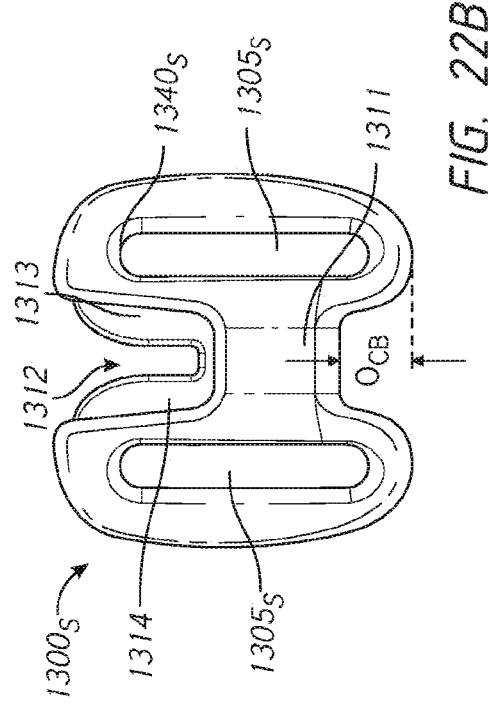
FIG. 22A is a front view of the size medium forehead coupler of FIG. 21B.
Figure 22B:
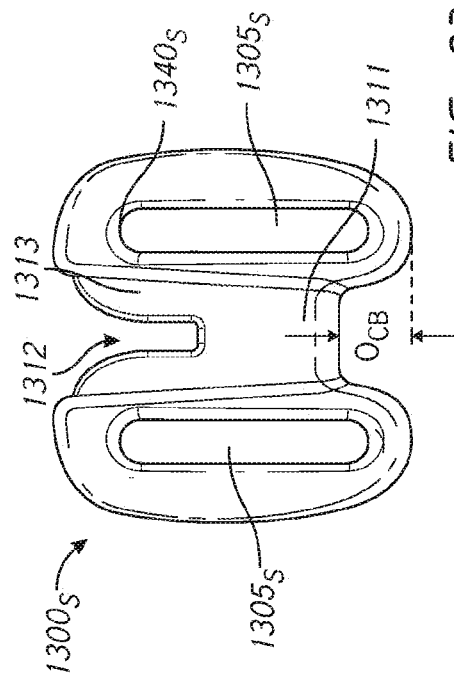
FIG. 22B is a front view of the size small forehead coupler of FIG. 21A.
Figure 23A:
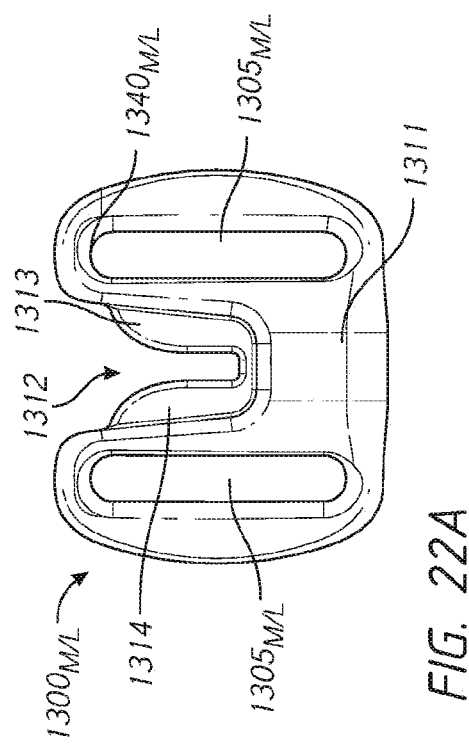
FIG. 23A is a rear view of the size medium forehead coupler of FIG. 21B.
Figure 23B:
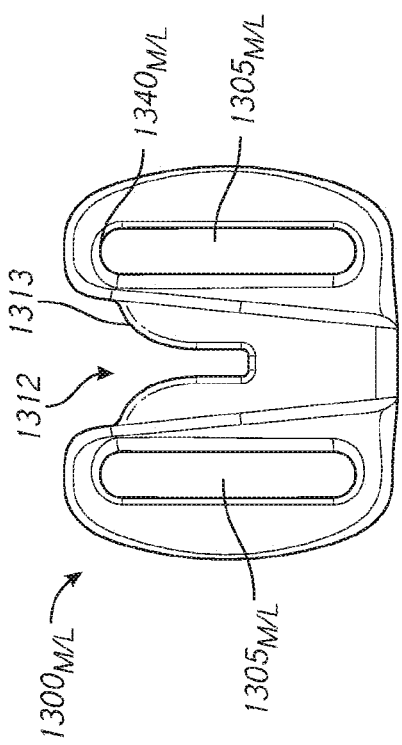
FIG. 23B is a rear view of the size small forehead coupler of FIG. 21A.

Accordingly, FIGS. 21A to 21C illustrate a universal frame 1301 connected to interchangeable forehead couplers $1300_S$, $1300_{M/L}$ to accommodate sealing cushions of various sizes. More specifically, the frame 1301 may be connected to the small forehead coupler $1300_S$ for use with smaller sealing cushion sizes and the medium/large forehead coupler $1300_{M/L}$, for medium to larger sealing cushion sizes. The small forehead coupler $1300_S$ is configured to position the forehead straps of a headgear at a lower position relative to the frame 1301 and the sealing cushion compared to the medium/large forehead coupler $1300_{M/L}$. As such, the small forehead coupler $1300_S$ and the medium/large forehead coupler $1300_{M/L}$, are substantially identical except that the strap apertures $1305_S$ are positioned lower on the small forehead coupler $1300_S$ than on the medium/large forehead coupler $1300_{M/L}$. In other words, as illustrated in FIGS. 22A to 25B, the size, shape, and geometries of the strap apertures $1305_S$, $1305_{M/L}$, the crossbar 1311, the rib slot 1312, the flange 1313, and the recess 1314 are identical between the forehead coupler $1300_S$, $1300_{M/L}$, such that both the forehead coupler $1300_S$, $1300_{M/L}$ may be used interchangeably with the frame 1301. In FIGS. 21A and 21B, both the strap apertures $1305_S$, $1305_{M/L}$ are illustrated as having an identical height H. However, the position of the strap apertures $1305_S$, $1305_{M/L}$ relative to the crossbar 1311, the rib slot 1312, the flange 1313, and the recess 1314 differs between the small forehead coupler $1300_S$ and the medium/large forehead coupler $1300_{M/L}$. More specifically, the strap apertures $1305_S$ of the small forehead coupler $1300_S$ are vertically offset by the offset distance $O_{CB}$ from the crossbar 1311, the rib slot 1312, the flange 1313, and the recess 1314 compared to their comparative positions on the medium/large forehead coupler $1300_{M/L}$. Put another way, the strap apertures $1305_S$ of the small forehead coupler $1300_S$ are positioned lower relative to the frame 1301 and the sealing cushion compared to the strap apertures $1305_{M/L}$ of the medium/large forehead coupler $1300_{M/L}$ by vertically offsetting the strap apertures $1305_S$ from the crossbar 1311 by the offset distance $O_{CB}$. Accordingly, when the frame 1301 is fitted with a smaller-sized sealing cushion, the small forehead coupler $1300_S$ positions the forehead straps of the headgear lower relative to the frame 1301 than the medium/large forehead coupler $1300_{M/L}$.

FIGS. 22A to 25B show various views of the small forehead coupler $1300_S$ and the medium/large forehead coupler $1300_{M/L}$ side-by-side for the sake of comparison. As illustrated, the crossbar 1311, the rib slots 1312, the flanges 1313, and the recesses 1314, are identical between the forehead coupler $1300_S$ and the forehead coupler $1300_{M/L}$ and only vary with respect to their positions relative to the strap apertures $1305_S$, $1305_{M/L}$. Providing identical crossbars 1311, rib slots 1312, flanges 1313, and recesses 1314 provides identical connection structure for connecting to the frame 1301 between the forehead couplers $1300_S$, $1300_{M/L}$ which allows interchangeability between the forehead couplers $1300_S$, $1300_{M/L}$.

As shown in FIGS. 25A and 25B, the crossbar 1311 and the flanges 1313 have a combined vertical length L on both the small forehead coupler $1300_S$ and the medium/large forehead coupler $1300_{M/L}$. The combined vertical length L is identical on both the small forehead coupler $1300_S$ and the medium/large forehead coupler $1300_{M/L}$. Further, in FIG. 25A, a distance X is measured from a lowermost edge of the crossbar 1311, which is also the lowermost edge of the medium/large forehead coupler $1300_{M/L}$, to the uppermost inner wall portion $1340_{M/L}$, of the strap apertures $1305_{M/L}$. Similarly, in FIG. 25B, the distance X is measured from the lowermost edge of the small forehead coupler $1300_S$ to the uppermost inner wall portion $1340_S$ of the strap apertures $1305_S$. The distance X is substantially identical on both the small forehead coupler $1300_S$ and the medium/large forehead coupler $1300_{M/L}$. However, the small forehead coupler $1300_S$ differs from the medium/large forehead coupler $1300_{M/L}$ in that the crossbar 1311 and the flanges 1313 on the small forehead coupler $1300_S$ are offset vertically upwards by the offset distance $O_{CB}$ compared to the medium/large forehead coupler $1300_{M/L}$. That is, the crossbar 1311 and the flanges 1313 are shifted vertically upwards by the offset distance $O_{CB}$ on the small forehead coupler $1300_S$. As a result, when the small forehead coupler $1300_S$ is attached to the frame 1301, the apertures $1305_S$ will be positioned lower on the frame 1301 than the apertures $1305_{M/L}$ when the medium/large forehead coupler $1300_{M/L}$ is attached to the frame 1301. Preferably, the offset distance $O_{CB}$ is approximately 5 mm That is, the apertures $1305_S$ are preferably positioned approximately 5 mm lower than the apertures $1305_{M/L}$. However, it should be understood to one of ordinary skill in the art that the offset distance may depend upon the variance in size between small and medium/large mask sizes. Further, it should be understood to one of ordinary skill in the art that the distance X is measured from the uppermost inner wall portion $1340_S$, $1340_{M/L}$ of the strap apertures $1305_S$, $1305_{M/L}$ because the frame 1301 and the forehead couplers $1300_S$, $1300_{M/L}$ are suspended and held by the forehead straps along the uppermost inner wall portion $1340_S$, $1340_{M/L}$, of the strap apertures $1305_S$, $1305_{M/L}$. In other words, the position of the uppermost inner wall portion $1340_S$, $1340_{M/L}$ of the strap apertures $1305_S$, $1305_{M/L}$ relative to the crossbar 1311 (i.e., or any other frame connector assembly) is generally determinative of the position of the forehead straps relative to the frame 1301 since the forehead couplers $1300_S$, $1300_{M/L}$, are suspended by the forehead straps by the uppermost inner wall portion $1340_S$, $1340_{M/L}$, of the strap apertures $1305_S$, $1305_{M/L}$. Even further, it should be understood to one of ordinary skill in the art that the combined vertical length L and the distance X are used to describe the comparative positions of the crossbar 1311 relative to the strap apertures $1305_S$, $1305_{M/L}$. Varying of the position of the crossbar 1311 relative to the strap apertures $1305_S$, $1305_{M/L}$ allows the position of the strap apertures $1305_S$, $1305_{M/L}$ to vary between the forehead couplers $1300_S$, $1300_{M/L}$, while still providing interchangeability of the forehead couplers $1300_S$, $1300_{M/L}$.

Figure 26:
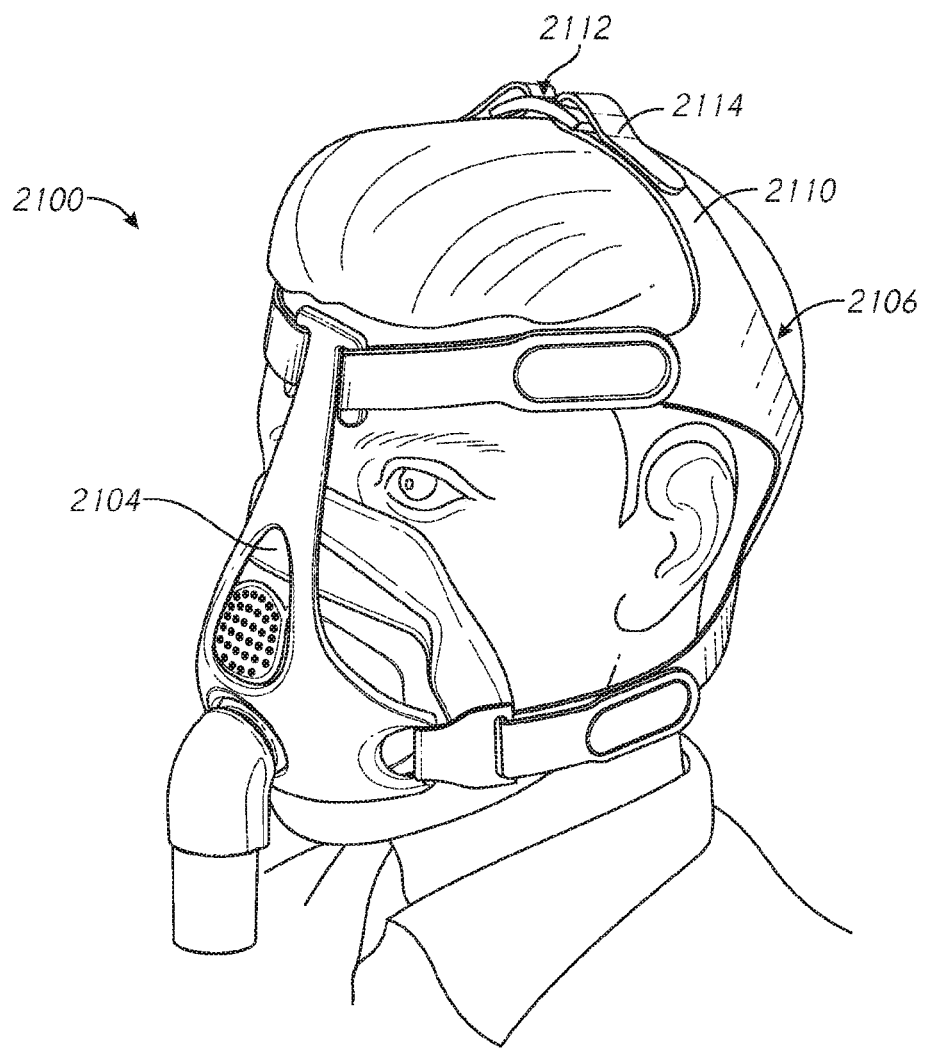
FIG. 26 shows a perspective view of a prior respiratory mask.

Some respiratory masks have headgear to secure them to a patient's face. The headgear often includes adjustable straps for adjusting the size of the headgear to match a range of patient head sizes. A crown strap can include two strap portions that are joined together by a buckle at a centrally located point on the top of a patients head. FIG. 26 shows a perspective view of a prior respiratory mask 2100 comprising a mask body 2104 and headgear 2106. While a nasal mask is shown, the presently disclosed subject matter is applicable to other mask types, such as nasal pillows, full face, and under nose. The headgear 2106 is configured to provide a means of easily connecting and disconnecting at least a portion of the headgear 2106 to the mask body 2104. The headgear 2106 includes a top strap or crown strap 2110 and a buckle member 2112. The buckle 2112 can be arranged to couple two portions of the crown strap 2110. Each of the portions of the crown strap 2110 preferably has an end portion 2114 and the end portion 2114 can have a coupling member such as a hook and loop fastener. The strap portions are threaded through at least one aperture in the buckle 2112 and folded back on themselves before being secured in place. The strap portions are usually secured in place by a hook and loop fastener (such as VELCRO®) at the end portions 2114. There is a tab portion at the end portions 2114 that comprises the hook component of the fastener that is configured to attach to the material of the strap portion, which forms the loop component of the fastener.

FIGS. 27-34 illustrate an embodiment of a headgear adjustment and connection system that includes a pair of straps that are configured to be linked together such that their combined length is incrementally adjustable. The disclosed embodiments can be used with a crown strap, other straps (such as upper and lower mask attachment straps), or any other headgear component. For example, the system can be utilized in the crown strap of a headgear for an interface. The portions of the headgear and/or interface can be the same as or similar to the headgear and interface assembly shown in FIG. 1, or can be of another suitable arrangement. The disclosed embodiments allow for coupling of the two strap portions without the use of a buckle or other additional component. Preferably, one of the two strap portions includes an aperture and the other strap portion includes one or more notches that are configured to engage the aperture as the strap portions are securely coupled together. In some embodiments, the ends of the strap portions each have a fastener, such as a hook and loop fastener, which are configured to fasten or couple the end to a surface of the other strap portion.

As illustrated in FIGS. 27-34, the headgear strap 2120 comprises a female strap portion 2122 and a male strap portion 2124. The female strap portion 2122 includes a free end 2126 and an attached end 2141. The male strap portion has a free end 2128 and an attached end 2140. Preferably, the attached ends 2140 and 2141 are configured to be permanently attached or integrally formed with other portions of the headgear. In other embodiments, the attached ends 2140 and 2141 can be removably attached or secured. The strap portions 2122 and 2124 can be made of a flexible material and can be elastic or inelastic. In some embodiments the material of the strap portions 2122 and 2124 comprises laminated layers of one or more polymers, foams or fabrics, such as Breath-o-prene. In some embodiments, the strap portions 2122 and 2124 can have inner and outer fabric layers and a central foam or polymer layer. Other flexible and durable materials may be suitable for the female and male straps 2122 and 2124. In other embodiments, the strap portions 2122 and 2124 can be formed from a central foam layer with non-stretch or low-stretch inner and outer fabric layers.

Each of the free ends 2126 and 2128 of the female and male strap portions 2122 and 2124 preferably defines a grip member or tab that is configured to be grasped by a user during connection and adjustment of the headgear. The free ends 2126 and 2128 can be sized and shaped to be engaged and pulled on by the fingers of a user to move the strap portions 2122 and 2124 relative to one another. The grip members or tabs defined by the free ends 2126 and 2128 can also be configured to be thin and substantially flat so that they lay flat against the opposite strap portion when the strap portions 2122 and 2124 are coupled.

Female strap portion 2122 has an inner surface 2136 and an outer surface 2152. Male strap portion 2124 has an inner surface 2134 and an outer surface 2150. The inner surface 2136 of the female strap portion 2122 supports a fastener 2142 and the inner surface 2134 of the male strap portion 2124 supports a fastener 2144. Preferably, fasteners 2142 and 2144 are configured to couple or hold the free ends 2126 and 2128 of the female and male strap portions 2122 and 2124 to the outer surface of the opposite strap portion. In some embodiments, fasteners 2142 and 2144 comprise hook and loop fastening systems (such as VELCRO®). Preferably, the outer surfaces 2150 and 2152 comprise a soft and/or textured fabric material that forms the loop component of the hook and loop fastener. Fasteners 2142 and 2144 can include a plastic hook component that is preferably fixed or permanently attached to the inner surface 2134, 2136 of the female and male straps 2122 and 2124 at or adjacent the free ends 2126 and 2128. The free ends 2126 and 2128 can be repeatedly coupled and decoupled from the outer surfaces 2150 and 2152 of the strap portions.

Fasteners 2142 and 2144 are preferably located entirely within the outer perimeter of free ends 2126 and 2128 of the female and male strap portions 2122 and 2124, such that there are no sharp edges exposed beyond the strap material. In the illustrated embodiment, the fastener 2142 comprises a hook component having a width A of between approximately 6 and 18 millimeters. In other embodiments, the width A is between approximately 10 and 14 millimeters. In another preferred embodiment, the width A is approximately 12 millimeters. The width B of the female and/or male strap portions 2122 and 2124 is preferably between approximately 10 and 24 millimeters and in some embodiments is between 16 and 20 millimeters. In another preferred embodiment, the width B is approximately 18 millimeters. Preferably, the difference in widths A and B, in combination with the hook component being slightly offset from the tip of each free end 2126 and 2128, provides that the edges of the free ends 2126 and 2128 are not coupled or attached to the opposing strap portion. This allows the patient/user to be able to lift the edges of the free ends 2126 and 2128 more easily for adjustment of the straps. The hook component can be the same for both the male and female strap portions.

Fasteners 2142 and 2144 can be secured in place on the straps by a welding process (ultrasonic or RF), adhesives, or any other form of attachment. The straps can also include 3D features at or adjacent to the free ends 2126 and 2128 of the strap portions 2122 and 2124. In some embodiments, by only welding the fasteners 2142 and 2144 and their hook component portions in certain areas, protruding or dimpled surfaces 2148 and 2149 can be formed in both the fasteners 2142 and 2144 and on the outer surfaces 2150 and 2152 of the strap portions. The dimpled surfaces 2148 and 2149 are formed where the fastener's hook component and the strap material have not been compressed by the welding process. The regions of the fasteners 2142 and 2144 that are compressed during the welding process may have the hooks crushed or deformed such that they cannot grip onto the loop component on the strap surfaces.

Fasteners 2142 and 2144 and their hook component portions are preferably the same size and shape for both the female and male strap portions 2122 and 2124, and they can be attached to the straps in the same manner. This is advantageous because the two strap portions 2122 and 2124 can be manufactured using a single process and tool. This minimizes manufacturing times and costs. Also, the 3D features forming dimpled surfaces 2148 and 2149 can provide improved tactile performance and usability of the free ends 2126 and 2128 of the female and male strap portions 2122 and 2124, such that it is easier to grip and couple/decouple the free ends 2126 and 2128.

Male strap portion 2124 preferably comprises a plurality of notches 2132 cut into one or more edges of the strap. In some embodiments, the notches 2132 are arranged in pairs, such that a notch 2132 on one edge of the strap portion 2124 is aligned with a corresponding notch 2132 on the opposite edge of the strap portion 2124. Preferably, a plurality of notch pairs 2132 are spaced evenly along part of the length of the male strap portion 2124, starting adjacent the free end 2128 and extending toward the attached end 2140. The notches 2132 are configured to provide incremental length adjustment of the headgear strap 2120. In the illustrated embodiment, there are two pairs of notches 2132 and each notch has a triangular or angled shape. The first pair of notches 2132 is offset or distanced from the tip of the free end 2128 so that the free end 2128 can define a tab or grasping portion between the notches 2132 and the tip of the free end 2128. In other embodiments there may be as few as one pair of notches, and in others there can be three or more notch pairs 2132 that provide more adjustment options for the strap connection. Some embodiments can also have notches with different sizes and shapes. For example, some notches could be rectangular or circular in shape and could extend more or less into the edge of the strap. In other embodiments, the strap 2124 can have a plurality of individual notches along one edge of the strap 2124 without any notches along the opposite edge of the strap 2124. In such embodiments, the notch depth can allow the strap portion 2124 to fit flat within the aperture 2130. Only a single notch would be engaged with the aperture 2130 at each size setting. In yet other embodiments, the strap 2124 can include a plurality of notches that alternate between sides along the length of the male strap portion 2124. In such embodiments, the notch depth can allow the strap 2124 to fit flat within the aperture 2130 and a single notch would be engaged with the aperture at each size setting.

The incremental adjustment provided by the notches 2132 allows for controlled adjustment of the headgear size, in comparison to the continuous adjustment provided by prior art systems. Controlled incremental adjustment can be beneficial as it provides precise sizing settings that can be repeatedly selected. If the headgear is removed from the mask for cleaning, the female and male strap portions 2122 and 2124 can be disconnected without the worry and inconvenience of losing the sizing of the headgear and having to refit it to the specific patient.

Female strap portion 2122 comprises an aperture 2130 that extends through a portion or length of the female strap portion 2122. Preferably, aperture 2130 extends through the free end 2126 and extends through the thickness of the strap portion 2122. The aperture 2130 can be a cut-out or hole that extends through both the inner surface 2136 and the outer surface 2152 of female strap portion 2122. Preferably, the aperture is offset or distanced from the tip of the free end 2126 such that the free end 2126 can be gripped between the aperture 2130 and the tip. The aperture 2130 is configured to receive the free end 2128 of the male strap portion 2124, thus linking the strap portions together. The notches 2132 of the male strap portion 2124 are configured to engage the aperture 2130 when the male strap portion 2124 passes through the aperture 2130. This arrangement of extending the male strap member 2124 through the aperture 2130 of the female strap portion 2122 with portions of the male strap member 2124 engaging the aperture 2130 can help to maintain the female and male strap portions 2122 and 2124 linearly aligned with each other, which provides consistent force vectors to support the mask on the patient's face. This arrangement can also help maintain a connection between the strap portions 2122 and 2124 during adjustment. This makes adjustment easier as the user does not have to hold the headgear in place on his head while adjusting the length.

Figure 27:
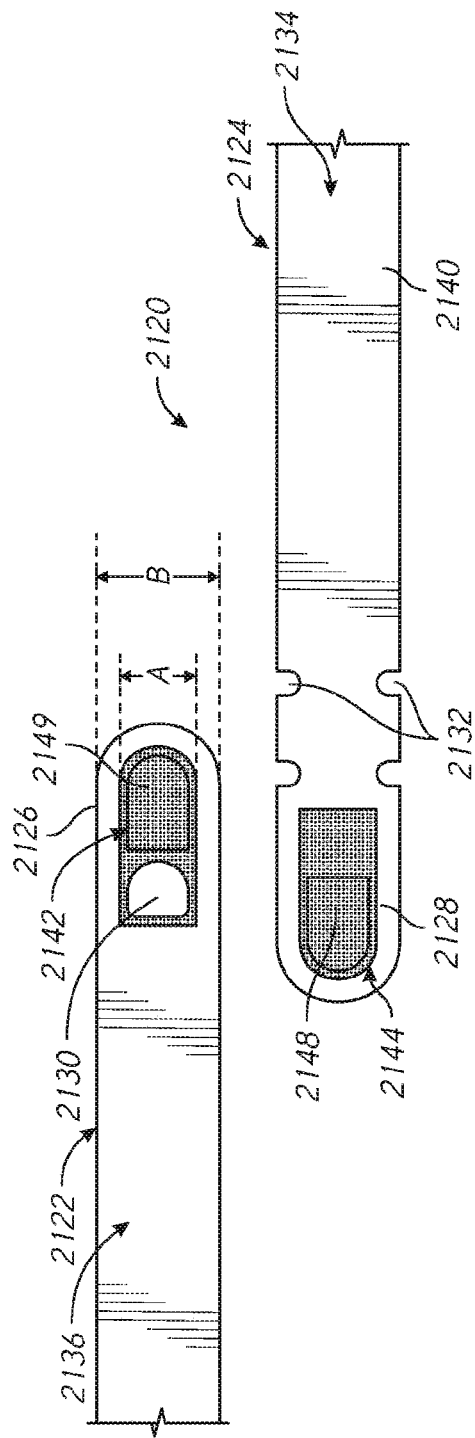
FIG. 27 shows a bottom view of an embodiment of the headgear strap of the present disclosure.
Figure 28:
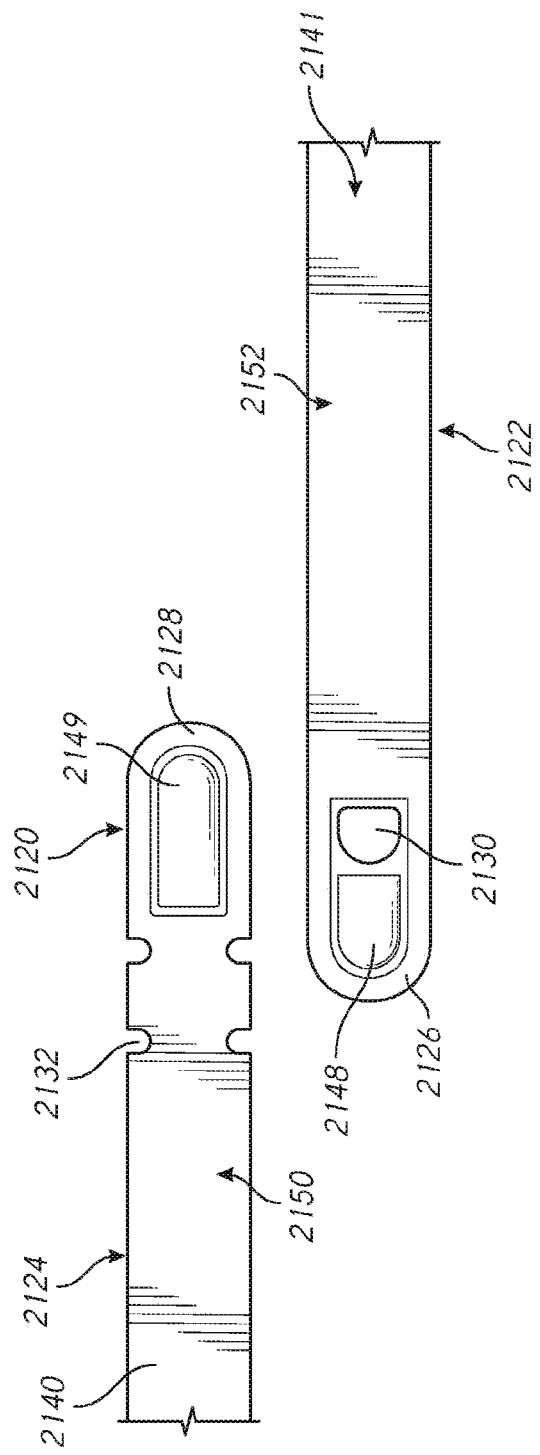
FIG. 28 shows a top view of the headgear strap of FIG. 27.

Preferably, the aperture 2130 is located within the perimeter of, and extends through a portion of the fastener 2142 on the female strap portion 2122, as shown in FIG. 27. The aperture 2130 can be punched out of the female strap portion 2122 as a secondary manufacturing step, after the fastener 2142 has been coupled to the strap portion 2122. Preferably, the aperture 2130 is positioned within a region of the fastener 2142 that is affixed or fused (by the welding process or adhesive) to the inner surface 2136, such that the hook component of the fastener 2142 is permanently joined around the entire perimeter of the aperture 2130. This reinforces the perimeter of the aperture 2130. In some embodiments, the hooks of the hook component of the fastener 2142 are crushed or deformed around the perimeter of the aperture 2130. The reinforced perimeter provides structure to the aperture 2130 that prevents it from deforming substantially as a result of forces applied to it by the male strap portion 2124 being drawn through the aperture 2130. This also makes it easier to draw the male strap portion 2124 smoothly through the aperture 2130. The reinforced perimeter also helps to engage the notches 2132 of the male strap portion 2124 during adjustment of the headgear size. It also provides a tactile response during adjustment so that the user can feel when each pair of notches 2132 is engaged and the size of the headgear has been adjusted by an increment. Having the hooks of the hook component of the fastener 2142 crushed or deformed adjacent to the perimeter of the aperture 2130 also minimizes the chances of the male strap portion 2124 catching on the hooks during coupling and assembly. This may also improve the ease with which the male strap portion 2124 can be drawn through the aperture 2130.

Preferably, aperture 2130 is sized and shaped so that the male strap portion 2124 is folded, bent or curved about its longitudinal axis in order to pass through the aperture 2130. Preferably, the male strap portion 2124 is configured to lay flat within the aperture 2130 when it is arranged in a position in which notches 2132 are engaging the aperture 2130. In some embodiments, the width D of the male strap portion 2124 and its free end 2128 is greater than the width C or height H of the aperture 2130. As illustrated, the aperture 2130 can be configured to have a straight side on its perimeter and also a curved portion along the perimeter. The straight side extends perpendicular to the longitudinal axis of the female strap portion 2122 and the curved portion can be a semi-circular arc. In other preferred embodiments, the aperture can have a different shape such as triangular or square-shaped, wherein the height and width dimensions of the aperture allow the male strap portion 2124 to pass through in a folded or bent position. Preferably, the width D of the male strap portion 2124 is between approximately 10 and 24 millimeters and the width C of the aperture 2130 is between approximately 5 and 14 millimeters. In other preferred embodiments, the width D is between approximately 16 and 20 millimeters and the width C is between approximately 8 and 10 millimeters. In one preferred embodiment the width D is approximately 18 millimeters and the width C is approximately 9 millimeters. Is some preferred embodiments, the width D is approximately 1.5-2.5 times greater than the width C, and in one preferred embodiment the width D is approximately 2 times greater than the width C. Preferably, height H of aperture 2130 is less than width C and is equal to or less than half the maximum width D of the male strap portion 2124.

Figure 33:
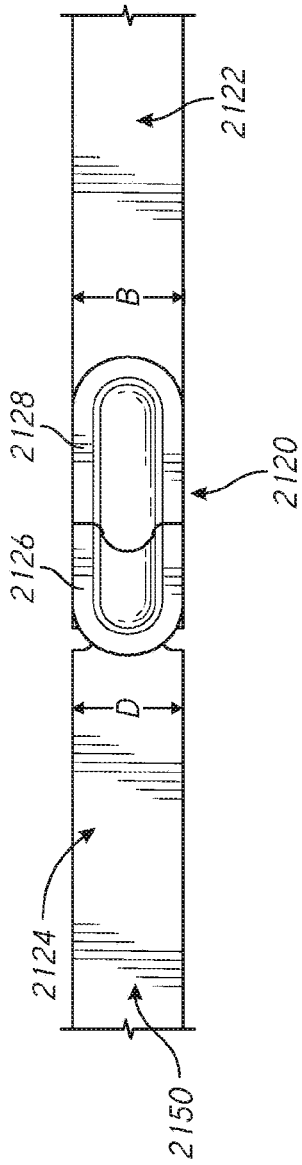
FIG. 33 shows a top view of the headgear strap of FIG. 27.

The width J of male strap portion 2124 between notches 2132 is approximately the same as width C of aperture 2130. This allows the male strap portion 2124 to extend in a flat manner within aperture 2130 when the notches 2132 are aligned with and engaging the aperture 2130. In other preferred embodiments, width J is less than width C. The curved portion of aperture 2130 has a perimeter or arc measurement P that defines the distance or length along the perimeter of the aperture 2130, excluding the straight side of aperture 2130. The measurement P is approximately the same as width D of the male strap portion 2124. In other preferred embodiments, measurement P is slightly less than width D and in other embodiments measurement P is greater than width D. Preferably, width B of female strap portion 2122 is approximately the same as measurement P and width D. The female and male strap portions 2122 and 2124 can have the same maximum widths B and D such that when the strap portions 2122 and 2124 are coupled, their edges do not protrude or extend beyond one another, which provides a smooth and consistent edge (as can be seen in FIG. 33). In one preferred embodiment, measurement P is approximately 18 millimeters.

Figure 32:
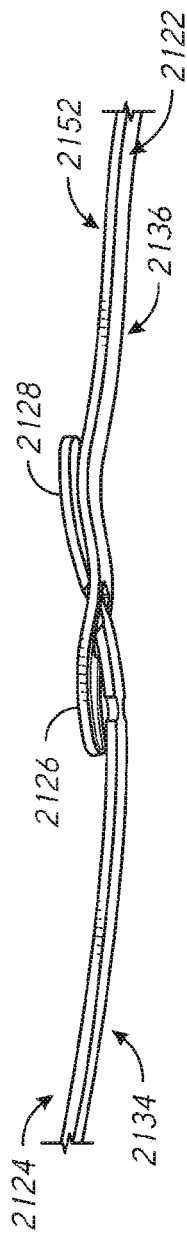
FIG. 32 shows a side view of the headgear strap of FIG. 27.

By matching the perimeter measurement P of the aperture 2130 to the maximum width D of the male strap portion 2124, the size of the aperture 2130 can be minimized, while still allowing passage of the strap portion 2124 through the aperture 2130. Minimizing the size of the aperture 2130 helps to maintain the structural integrity of the female strap portion 2122 and maintains a close-fitting coupling between the female and male strap portions 2122 and 2124. A close fit between the strap portions 2122 and 2124 prevents unintentional disconnection of the straps. Allowing the male strap portion 2124 to flatten out when a pair of notches 2132 is aligned with the aperture 2130 permits the straps 2122 and 2124 to maintain a low profile when coupled, as shown in FIG. 32. The notches 2132 can also function as an end stop feature, wherein the width of the male strap portion 2124 outside of the notches 2132 prevents it from unintentionally slipping through the aperture 2130.

Figure 29:
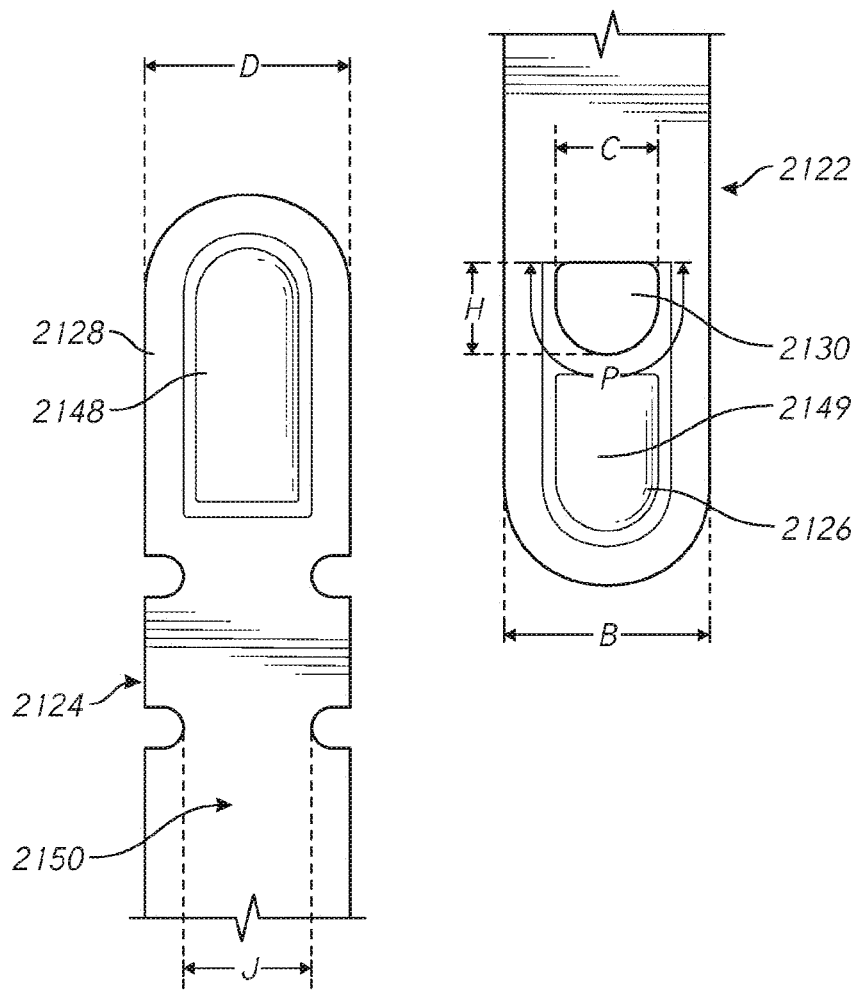
FIG. 29 shows a closer top view of the headgear strap of FIG. 27.
Figure 30:
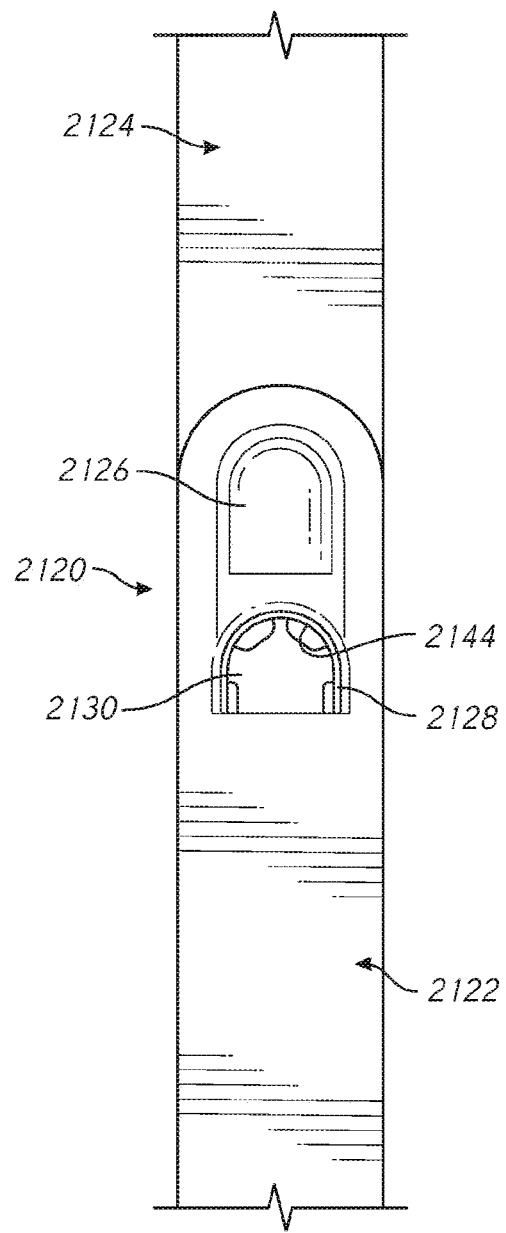
FIG. 30 shows top view of the headgear strap of FIG. 27 as the male portion is inserted into the aperture of the female portion.

As illustrated, aperture 2130 is sized and shaped to allow the free end 2128 of the male strap portion 2124 to pass through it, as shown in FIG. 29. Both strap portions 2122 and 2124 can have approximately equal maximum widths B and D. In order for a consistent maximum width to be maintained along the lengths of the strap portions 2122 and 2124, the aperture 2130 preferably has a narrower width C than the maximum widths B and D of the strap portions 2122 and 2124. For the male strap portion 2124 to fit through the narrower aperture 2130, the strap portion 2124 is folded or bent such that its width is reduced to match or be smaller than the width C of the aperture 2130. In bending or folding the male strap portion 2124, its depth is increased so the aperture 2130 preferably has corresponding depth or height H. The dimensions of aperture 2130 can be selected to allow for the increased depth of the strap portion 2124 to pass through. Preferably, the hook component of the hook and loop fastener 2144 limits the ability of the male strap portion 2124 to be folded or bent to fit through the aperture 2130. FIG. 30 shows the male strap portion 2124 being folded or bent as it passes through the aperture 2130. The hook component of the fastener 2144 buckles and bunches and can limit how narrow the strap portion 2124 can be bent, which in turn restricts how narrow the aperture width C can be.

Figure 31:
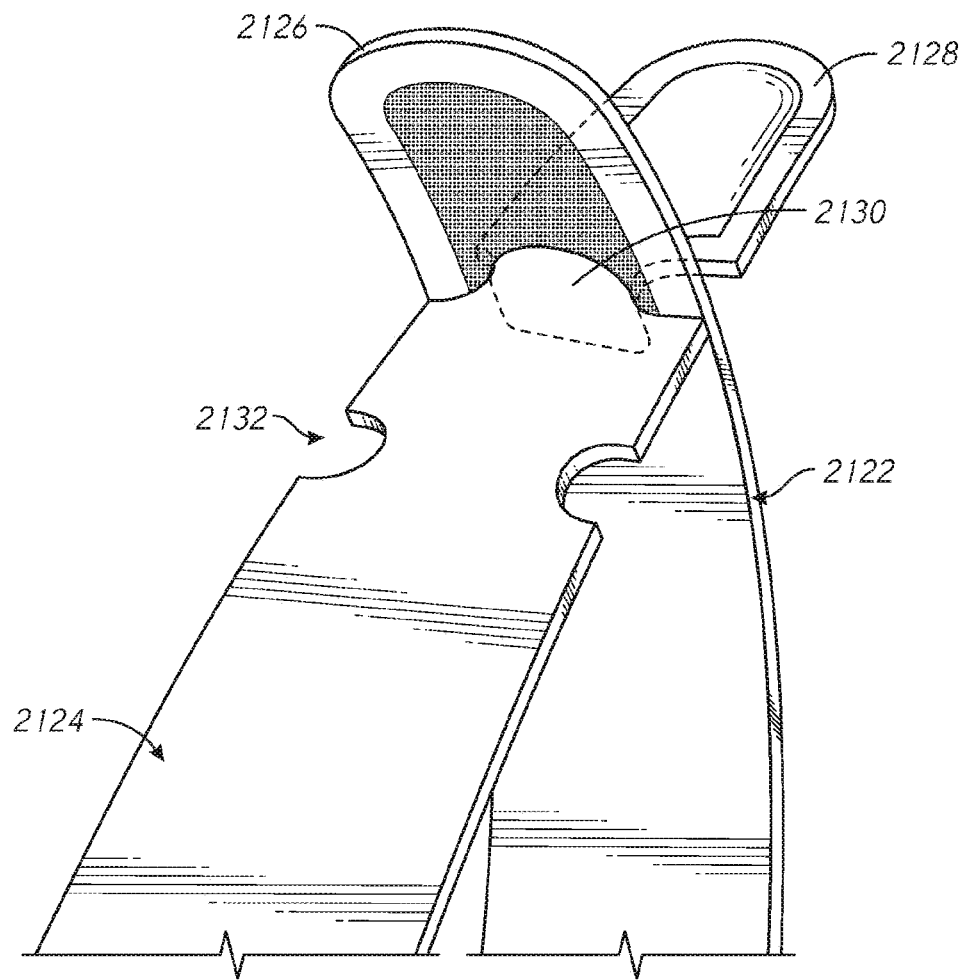
FIG. 31 shows perspective view of the headgear strap of FIG. 27 as the male portion is inserted into the aperture of the female portion.
Figure 34:
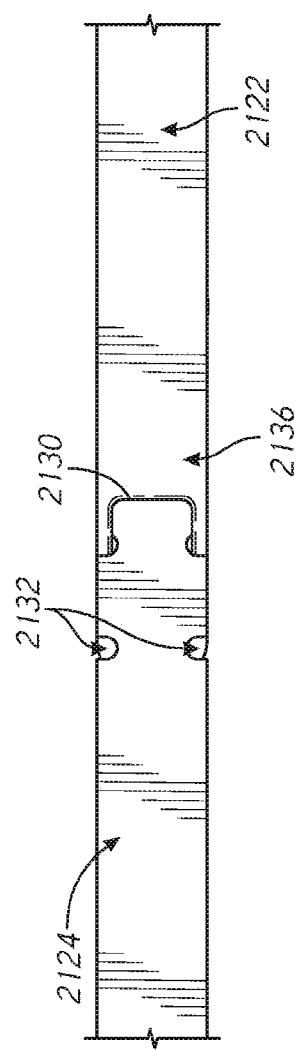
FIG. 34 shows a bottom view of the headgear strap of FIG. 27.

As illustrated in FIG. 31, in order to adjust the headgear assembly and couple the strap portions 2122 and 2124, free end 2128 of male strap portion 2124 extends through aperture 2130 and notches 2132 engage the aperture 2130. In this position, the male strap portion 2124 can lay flat against the straight side of the aperture 2130 and the two strap portions 2122 and 2124 can be pressed flat against one another, as shown in FIGS. 32-34. The notches 2132 engaging the aperture 2130 assists in maintaining the position of the male strap portion 2124 relative to the female strap portion 2122. Fastener 2142 on the female strap portion 2122 engages the outer surface 2150 of male strap portion 2124 and fastener 2144 engages the outer surface 2152 of female strap portion 2122. The fasteners 2142 and 2144 can hold the free ends 2126 and 2128 against straps portions 2122 and 2124. The coupled strap portions 2122 and 2124 are securely coupled and can have a low profile. In this manner, the size adjustment for a headgear strap is built into the strap portions 2122 and 2124. No secondary component, such as a buckle or clip, is required to couple the strap portions. The strap portions 2124 and 2122 are connected directly to each other and are adjustable relative to one another. The amount of overlap between the strap portions 2122 and 2124 can determine the adjusted size for the headgear. This arrangement is advantageous at least because it has a low profile and is less bulky than a buckle. The arrangement also improves comfort of the patient as only the straps 2122 and 2124 are contacting the user and there are no hard parts that would cause discomfort. There are also fewer components and therefore less assembly is required, and manufacturing costs are reduced. It is also beneficial because it requires only a single adjustment to change size (a buckle configuration requires that each of the strap portions has to be individually adjusted), which means quicker and easier fitting of a mask.

Figure 35:
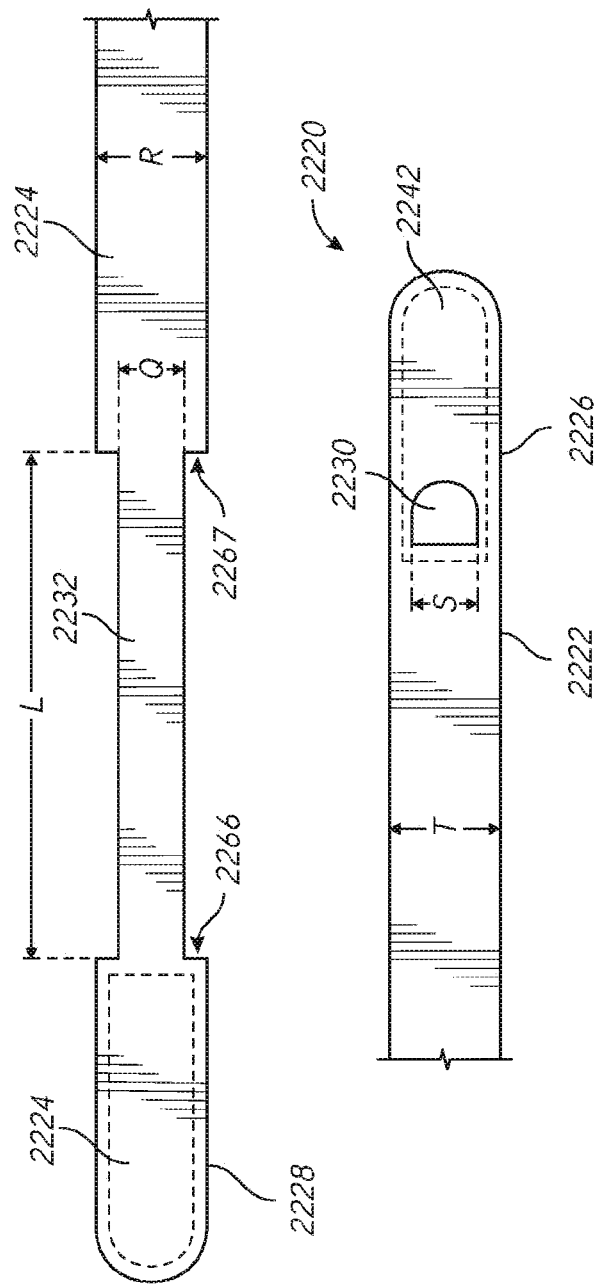
FIG. 35 shows a top view of an embodiment of a headgear strap.

FIG. 35 illustrates an embodiment of a headgear adjustment and connection system that includes a pair of straps that are configured to be linked together such that their combined length is continuously adjustable. The headgear strap assembly 2220 comprises a female strap portion 2222 and a male strap portion 2224. The female strap portion 2222 includes a free end 2226 and the male strap portion 2224 has a free end 2228. Preferably, the other ends of the strap portions are configured to be permanently attached or removably attached with other portions of the headgear. Similar to the embodiments described above, strap portions 2222 and 2224 can be made of a flexible material and can be elastic or inelastic. In some embodiments the material of the strap portions 2222 and 2224 comprises laminated layers of one or more polymers, foams or fabrics, such as Breath-o-prene. In some embodiments, the strap portions 2222 and 2224 can have inner and outer fabric layers and a central foam or polymer layer.

Each of the free ends 2226 and 2228 of the male and female strap portions 2222 and 2224 preferably defines a grip member or tab that is configured to be grasped by a user during connection and adjustment of the headgear. The grip members or tabs defined by the free ends 2226 and 2228 can also be configured to be thin and substantially flat so that they lay flat against the opposite strap portion when the strap portions 2222 and 2224 are coupled.

In the illustrated embodiment, the female strap portion 2222 comprises an aperture 2230. Preferably, the aperture 2230 extends through a portion or length of the female strap portion 2222. Preferably, aperture 2230 extends through the free end 2226 and extends through the thickness of the strap portion 2222. The aperture 2230 can be a cut-out or hole that extends through both the inner surface and the outer surface of female strap portion 2222. Preferably, the aperture 2230 is offset or distanced from the tip of the free end 2226 such that the free end 2226 can be gripped between the aperture 2230 and the tip. The aperture 2230 is configured to receive the free end 2228 of the male strap portion 2224, thus linking the strap portions together.

The male strap portion 2224 includes an adjustment portion 2232 that is preferably narrower than the surrounding portions of the male strap portion 2224. The adjustment portion 2232 is configured to enter and/or engage the aperture 2230 when the male strap portion 2224 passes through the aperture 2230. The adjustment portion 2232 has a length L and the male strap portion 2224 can be adjusted relative to the female strap portion 2222 at any position at which any portion of the adjustment portion 2232 along its length L is aligned with the aperture 2230. Preferably, the free end 2226 includes a fastener 2242 and the free end 2228 includes a fastener 2244. Each of the fasteners 2242 and 2244 is configured to engage and fasten to the outer surface of the opposite strap portion, as described in the previous embodiments. This arrangement of extending the male strap member 2224 through the aperture 2230 of the female strap portion 2222 with the adjustment portion 2232 within the aperture 2230 can help to maintain the male and female strap portions 2222 and 2224 linearly aligned with each other, which provides consistent force vectors to support the mask on the patient's face. This arrangement can also help maintain a connection between the strap portions 2222 and 2224 during adjustment. This arrangement further allows for continuous adjustment of the strap portions relative to one another throughout the length L so that the strap portions can be adjusted in very small increments to provide countless size options. This also makes adjustment easier as the user does not have to hold the headgear in place on his head while adjusting the length.

Preferably, the male strap portion 2224 includes a transition 2266 at the end of the adjustment portion 2232 that is configured to provide a stop or engagement surface that deters decoupling of the strap portions 2222 and 2224. The male strap portion 2224 can also include a transition 2267 at the opposite end of the adjustment portion 2232 that is configured to provide an engagement surface or stop that limits movement of the aperture 2230 past that point and deters overtightening of the strap portions.

As illustrated, the male strap portion 2224 has a width R and the adjustment portion 2232 has a width Q. The female strap portion 2222 has a width T and the aperture has a width S. Preferably, the widths T and R of the strap portions 2222 and 2224 are substantially the same. In one preferred embodiment, the width Q of the adjustment portion 2232 is approximately the same as the width S of the aperture 2230. In such an arrangement, there is little or no friction or engagement between the adjustment portion 2232 and the aperture 2230 as the adjustment portion 2232 passes through the aperture 2230. However, the fasteners 2242 and 2244 engage the surface of the opposite strap portion and retain the coupling of the strap portions.

In another preferred embodiment, the widths R and T of the strap portions 2222 and 2224 are greater than the width Q of the adjustment portion 2232. The width Q of the adjustment portion 2232 can also be greater than the width S of the aperture 2230. In such an embodiment, there is friction or engagement between the adjustment portion 2232 and the aperture 2230 as the adjustment portion 2232 passes through the aperture 2230 which assists in the retention of the coupling of the strap portions 2222 and 2224. The greater the width Q relative to the width S, the more friction there is and more force is required to decouple the strap portions 2222 and 2224 or adjust them relative to one another. In another embodiment, the width Q is substantially the same as the width R of the strap portion 2224. In such an embodiment there are little or no transitions at the end of the adjustment portion 2230 to limit overtightening or deter uncoupling of the strap portions 2222 and 2224.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the disclosure, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Language of degree used herein, such as the terms "approximately," "about," "generally," and "substantially," as used herein represent a value, amount or characteristic close to the stated value, amount or characteristic that still performs a desired function or achieves a desired result. The deviation from the stated value, amount or characteristic could, for example, reflect acceptable tolerances, conversion factors, rounding off, measurement error, or other factors known to those of skill in the art. For example, the terms "generally parallel" and "substantially parallel" refer to a value, amount or characteristic that can depart from exactly parallel by less than or equal to 15 degrees, 10 degrees, 5 degrees, 3 degrees, 1 degree, 0.1 degree, or otherwise.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:

1. A connector system for connecting a headgear to a respiratory mask, the connector system comprising:
   a frame connected to the respiratory mask;
   a hook connector portion disposed on the frame, the hook connector portion comprising a rib; and
   first and second forehead straps attached to the headgear, wherein the first and second forehead straps are attached to the frame with a forehead coupler to connect the headgear to the respiratory mask, the forehead coupler comprising:
   a pair of lateral strap connectors; and a frame connector configured to link the strap connectors together;
wherein the frame connector comprises a crossbar and a rib slot, the rib slot is formed within a thin flange that extends upwardly from the crossbar and extends between the two strap connectors, the thin flange creating a recess on a front side of the frame connector,
wherein the forehead coupler is configured to removably attach to the hook connector portion,
wherein the rib of the hook connector portion is positioned within the rib slot of the forehead coupler.

2. The connector system of claim 1,
wherein the hook connector portion further comprises:
a shank connected to the frame,
a bend connected to the shank,
a return arm connected to the bend, and
a throat portion positioned between the shank and the return arm,
wherein the frame connector of the forehead coupler is sandwiched between the shank and the return arm such that the forehead coupler is removably attached to the hook connector portion and the first and second forehead straps are removably attached to the frame,
wherein the hook connector portion further comprises:
a rib extending into the throat portion from the shank toward the return arm,
wherein the rib is positioned within the rib slot of the forehead coupler when the forehead coupler is attached to the hook connector portion and contact between the rib and the rib slot obstructs rotation of the forehead coupler relative to the frame.

3. The connector system of claim 2, wherein the rib is separated from the bend and the return arm.

4. The connector system of claim 2, wherein the recess of the frame connector contacts the return arm and obstructs the forehead coupler from being inserted into the throat portion when the recess faces the return arm.

5. The connector system of claim 2, wherein an end portion of the return arm extends towards the shank to define a throat opening between the return arm and the shank, wherein a width of the throat opening between the return arm and the shank is narrower than a width of the throat portion between the return arm and the shank, wherein the width of the throat opening between the return arm and the shank is narrower than a thickness of the forehead straps, wherein a thickness of an end of the frame connector of the forehead coupler is greater than double the width of the throat opening.

6. The connector system of claim 2, wherein the frame is a universal frame configured to fit a plurality of respiratory mask sizes, wherein a position of the frame connector of the forehead coupler with respect to the strap connectors varies between a smaller-sized respiratory mask and a larger-sized respiratory mask, wherein, comparatively, the position of the frame connector of the forehead coupler with respect to the strap connectors for the smaller-sized respiratory mask is positioned vertically higher than the frame connector of the forehead coupler with respect to the strap connectors for the larger sized respiratory mask such that the strap connectors for the smaller-sized respiratory mask are positioned lower with respect to the universal frame than the strap connectors for the larger sized respiratory mask.

7. The connector system of claim 1, wherein the pair of lateral strap connectors each comprise a strap aperture and a strap guide.

8. The connector system of claim 1, wherein the crossbar has a cross-sectional profile comprising a first end and a second end connected by two flat sides.

9. The connector system of claim 8, wherein the first and second ends have semicircular profiles, wherein a diameter of the first end is smaller than a diameter of the second end, wherein a length of the two flat sides is greater than the diameter of the second end.

10. The connector system of claim 8, wherein an acute angle is formed between the two flat sides.

11. The connector system of claim 1, wherein the frame connector is offset from the pair of lateral strap connectors.

12. The connector system of claim 1, wherein the thin flange extends tangentially from a back side of the crossbar, thereby creating the recess on the front side of the frame connector.

13. The connector system of claim 1, wherein the rib slot comprises two substantially vertical long edges separated by a horizontal short edge parallel with the crossbar.

14. The connector system of claim 13, wherein the two long edges extend perpendicularly from ends of the short edge and curve outwardly in an upwards direction.

15. The connector system of claim 2, wherein an end portion of the return arm comprises a bump configured to extend toward the shank.

16. The connector system of claim 15, wherein the bump comprises an angled surface, the angled surface configured towards the shank.

17. The connector system of claim 15, wherein the bump is rounded by a fillet.

18. The connector system of claim 15, wherein an apex of the bump is offset from an end of the return arm.

19. A connector system for connecting a headgear to a respiratory mask, the connector system comprising:
a frame connected to the respiratory mask; and
first and second forehead straps attached to the headgear,
wherein the first and second forehead straps are attached to the frame with a forehead coupler to connect the headgear to the respiratory mask, the forehead coupler comprising:
a pair of lateral strap connectors; and
a frame connector configured to link the strap connectors together;
wherein the frame connector comprises a crossbar and a rib slot, the rib slot is formed within a thin flange that extends upwardly from the crossbar and extends between the two strap connectors, the thin flange creating a recess on a front side of the frame connector,
wherein a portion of the frame is configured to removably attach to the forehead coupler by engaging the rib slot.

20. The connector system of claim 19, further comprising:
a hook connector portion disposed on the frame, the hook connector portion further comprising:
a shank connected to the frame,
a bend connected to the shank,
a return arm connected to the bend, and
a throat portion positioned between the shank and the return arm,
wherein the frame connector of the forehead coupler is sandwiched between the shank and the return arm such that the forehead coupler is removably attached to the hook connector portion and the first and second forehead straps are removably attached to the frame,
the hook connector portion further comprising:

a rib extending into the throat portion from the shank toward the return arm, wherein the rib is positioned within the rib slot of the forehead coupler when the forehead coupler is attached to the hook connector portion and contact between the rib and the rib slot obstructs rotation of the forehead coupler relative to the frame.

21. The connector system of claim 20, wherein the rib is separated from the bend and the return arm.

22. The connector system of claim 20, wherein the recess of the frame connector contacts the return arm and obstructs the forehead coupler from being inserted into the throat portion when the recess faces the return arm.

23. The connector system of claim 20, wherein an end portion of the return arm extends towards the shank to define a throat opening between the return arm and the shank, wherein a width of the throat opening between the return arm and the shank is narrower than a width of the throat portion between the return arm and the shank, wherein the width of the throat opening between the return arm and the shank is narrower than a thickness of the forehead straps, wherein a thickness of an end of the frame connector of the forehead coupler is greater than double the width of the throat opening.

24. The connector system of claim 20, wherein the frame is a universal frame configured to fit a plurality of respiratory mask sizes, wherein a position of the frame connector of the forehead coupler with respect to the strap connectors varies between a smaller-sized respiratory mask and a larger-sized respiratory mask, wherein, comparatively, the position of the frame connector of the forehead coupler with respect to the strap connectors for the smaller-sized respiratory mask is positioned vertically higher than the frame connector of the forehead coupler with respect to the strap connectors for the larger sized respiratory mask such that the strap connectors for the smaller-sized respiratory mask are positioned lower with respect to the universal frame than the strap connectors for the larger sized respiratory mask.

25. The connector system of claim 19, wherein the pair of lateral strap connectors each comprise a strap aperture and a strap guide.

26. The connector system of claim 19, wherein the crossbar has a cross-sectional profile comprising a first end and a second end connected by two flat sides.

27. The connector system of claim 26, wherein the first and second ends have semicircular profiles, wherein a diameter of the first end is smaller than a diameter of the second end, wherein a length of the two flat sides is greater than the diameter of the second end.

28. The connector system of claim 26, wherein an acute angle is formed between the two flat sides.

29. The connector system of claim 19, wherein the frame connector is offset from the pair of lateral strap connectors.

30. The connector system of claim 19, wherein the thin flange extends tangentially from a back side of the crossbar, thereby creating the recess on the front side of the frame connector.

31. The connector system of claim 19, wherein the rib slot comprises two substantially vertical long edges separated by a horizontal short edge parallel with the crossbar.

32. The connector system of claim 31, wherein the two long edges extend perpendicularly from ends of the short edge and curve outwardly in an upwards direction.

33. The connector system of claim 20, wherein an end portion of the return arm comprises a bump configured to extend toward the shank.

34. The connector system of claim 33, wherein the bump comprises an angled surface, the angled surface configured towards the shank.

35. The connector system of claim 33, wherein the bump is rounded by a fillet.

36. The connector system of claim 33, wherein an apex of the bump is offset from an end of the return arm.

37. A connector system for connecting a headgear to a respiratory mask, the connector system comprising:
  a frame connected to the respiratory mask; and
  a hook connector portion disposed on the frame;
  first and second forehead straps attached to the headgear,
  wherein the first and second forehead straps are attached to the frame with a forehead coupler to connect the headgear to the respiratory mask, the forehead coupler comprising:
    a pair of lateral strap connectors; and
    a frame connector configured to link the strap connectors together;
    wherein the frame connector comprises a crossbar and a rib slot, the rib slot is formed within a thin flange that extends upwardly from the crossbar and extends between the two strap connectors, the thin flange creating a recess on a front side of the frame connector,
  wherein the forehead coupler is removably attached to the hook connector portion,
  wherein the recess of the forehead coupler is configured to receive a portion of the hook connector portion such that the forehead coupler is configured to be removed from the hook connector portion in a downward direction.

38. The connector system of claim 37,
  wherein the hook connector portion further comprises:
    a shank connected to the frame,
    a bend connected to the shank,
    a return arm connected to the bend, and
    a throat portion positioned between the shank and the return arm,
    wherein the frame connector of the forehead coupler is sandwiched between the shank and the return arm such that the forehead coupler is removably attached to the hook connector portion and the first and second forehead straps are removably attached to the frame,
  wherein the hook connector portion further comprises:
    a rib extending into the throat portion from the shank toward the return arm,
    wherein the rib is positioned within the rib slot of the forehead coupler when the forehead coupler is attached to the hook connector portion and contact between the rib and the rib slot obstructs rotation of the forehead coupler relative to the frame.

39. The connector system of claim 38, wherein the rib is separated from the bend and the return arm.

40. The connector system of claim 38, wherein the frame connector of the forehead coupler includes a recess positioned on one side of the frame connector, wherein the recess contacts the return arm and obstructs the forehead coupler from being inserted into the throat portion when the recess faces the return arm.

41. The connector system of claim 38, wherein an end portion of the return arm extends towards the shank to define a throat opening between the return arm and the shank, wherein a width of the throat opening between the return arm and the shank is narrower than a width of the throat portion between the return arm and the shank, wherein the width of the throat opening between the return arm and the shank is narrower than a thickness of the forehead straps, wherein a thickness of an end of the frame connector of the forehead coupler is greater than double the width of the throat opening.

42. The connector system of claim 38, wherein the frame is a universal frame configured to fit a plurality of respiratory mask sizes, wherein a position of the frame connector of the forehead coupler with respect to the strap connectors varies between a smaller-sized respiratory mask and a larger-sized respiratory mask, wherein, comparatively, the position of the frame connector of the forehead coupler with respect to the strap connectors for the smaller-sized respiratory mask is positioned vertically higher than the frame connector of the forehead coupler with respect to the strap connectors for the larger sized respiratory mask such that the strap connectors for the smaller-sized respiratory mask are positioned lower with respect to the universal frame than the strap connectors for the larger sized respiratory mask.

43. The connector system of claim 38, wherein the pair of lateral strap connectors each comprise a strap aperture and a strap guide.

44. The connector system of claim 37, wherein the crossbar has a cross-sectional profile comprising a first end and a second end connected by two flat sides.

45. The connector system of claim 44, wherein the first and second ends have semicircular profiles, wherein a diameter of the first end is smaller than a diameter of the second end, wherein a length of the two flat sides is greater than the diameter of the second end.

46. The connector system of claim 44, wherein an acute angle is formed between the two flat sides.

47. The connector system of claim 37, wherein the frame connector is offset from the pair of lateral strap connectors.

48. The connector system of claim 37, wherein the thin flange extends tangentially from a back side of the crossbar, thereby creating the recess on the front side of the frame connector.

49. The connector system of claim 37, wherein the rib slot comprises two substantially vertical long edges separated by a horizontal short edge parallel with the crossbar.

50. The connector system of claim 49, wherein the two long edges extend perpendicularly from ends of the short edge and curve outwardly in an upwards direction.

51. The connector system of claim 38, wherein an end portion of the return arm comprises a bump configured to extend toward the shank.

52. The connector system of claim 51, wherein the bump comprises an angled surface, the angled surface configured towards the shank.

53. The connector system of claim 51, wherein the bump is rounded by a fillet.

54. The connector system of claim 51, wherein an apex of the bump is offset from an end of the return arm.

* * * * *